(12) United States Patent
Chamberlain et al.

(10) Patent No.: US 7,087,618 B2
(45) Date of Patent: Aug. 8, 2006

(54) PYRAZOLOPYRIDINYL PYRIMIDINE THERAPEUTIC COMPOUNDS

(75) Inventors: Stanley D. Chamberlain, Durham, NC (US); Kristjan Gudmundsson, Durham, NC (US); Brian A. Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 11 days.

(21) Appl. No.: 11/082,466

(22) Filed: Mar. 17, 2005

(65) Prior Publication Data

US 2005/0182080 A1 Aug. 18, 2005

Related U.S. Application Data

(62) Division of application No. 10/433,884, filed as application No. PCT/US01/44210 on Nov. 26, 2001.

(60) Provisional application No. 60/255,763, filed on Dec. 15, 2000, provisional application No. 60/274,284, filed on Mar. 8, 2001, provisional application No. 60/315,089, filed on Aug. 27, 2001.

(51) Int. Cl.
C07D 403/04 (2006.01)
A61K 31/506 (2006.01)

(52) U.S. Cl. ...................... 514/275; 544/331

(58) Field of Classification Search ............... 544/331; 514/275
See application file for complete search history.

(56) References Cited

U.S. PATENT DOCUMENTS

| | | | |
|---|---|---|---|
| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,773,530 A | 6/1998 | Akahane et al. |
| 5,990,148 A | 11/1999 | Isakson et al. |
| 6,136,839 A | 10/2000 | Isakson et al. |
| 6,207,675 B1 | 3/2001 | Carry et al. |
| 6,919,352 B1 | 7/2005 | Chamberlain et al. |
| 2004/0053942 A1 | 3/2004 | Alberti et al. |

FOREIGN PATENT DOCUMENTS

| | | |
|---|---|---|
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | 0 364 204 A1 | 10/1989 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98/56377 | 12/1998 |
| WO | WO 99 12930 | 3/1999 |
| WO | WO 99/58523 | 11/1999 |
| WO | WO 99/59585 | 11/1999 |
| WO | WO 99/64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |

(Continued)

OTHER PUBLICATIONS

Vane, J. et al. "Towards a Better Aspirin," Nature, vol. 367, Jan. 20, 1994, pp. 215-216.

(Continued)

*Primary Examiner*—Deepak Rao
(74) *Attorney, Agent, or Firm*—Lovie Ann Morgan

(57) ABSTRACT

The present invention provides compounds of formula (I): wherein all variables are as defined herein, pharmaceutical compositions containing the same, processes for preparing the same and their use as pharmaceutical agents

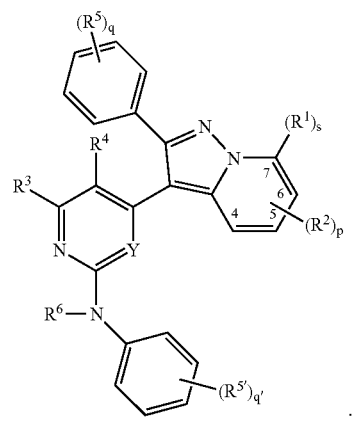

27 Claims, No Drawings

FOREIGN PATENT DOCUMENTS

| WO | WO 02 18382 | 3/2002 |
|---|---|---|
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Carter, J. et al. "Recently Reported Inhibitors of Cyclooxygenase-2." Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p. 38 kinase." Expert Opinion Ther. Patents, 1997, 7(7):729-733.

Roizman, B., et al. "The Family Herpesviridae: A Brief Introduction." Fields Virology, vol. 2, 4th Edition, pp. 2381-2397, 2001.

Douglas, R.G., Jr. "Introduction to Viral Diseases." Cecil Textbook of Medicine, 20th Edition, vol. 2, pp. 1739-1747, 1996.

Bosseray, A., et al. "What's New in Vaccines Against Herpes Simplex Infections." PubMed Abstract. Pathol. Biol. 50(8): 483-92, Oct. 2002.

Razonable, R., et al. "Herpesvirus Infections in Transplant Recipients: Current Challenges in the Clinical Management of Cytomegalovirus and Epstein-Barr Virus Infection." PubMed Abstract. Herpes 10(3):60-5, Dec. 2003.

PYRAZOLOPYRIDINYL PYRIMIDINE THERAPEUTIC COMPOUNDS

CROSS REFERENCES TO RELATED APPLICATIONS

This application is divisional of U.S. patent Application Ser. No. 10/433,884, filed 5 Jun. 2003, now U.S. Pat. No. 6,919,352, which is a 371 Application of PCT/US01/44210, filed 26 Nov. 2001, which claims priority to U.S. application Ser. No. 60/255,763, filed 15 Dec. 2000; U.S. Application Ser. No. 60/274,284, filed 8 Mar. 2001; and Ser. No. 60/315,089, filed 27 Aug. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataract's hereby endangering the host's sight Infection in the new-born, in immunocompromised patients or penetration of the infection into the central nervous system can prove fatal. In the US alone, 40 million individuals are infested with HSV-2, a number that is expected to increase to 60 million by 2007. Over 80% of individuals infected with HSV-2 are unaware they carry and spread the virus, and of those diagnosed less than 20% received oral therapies. The net result is that less than 50% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

VZV is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome and,multiple sclerosis.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

PCT Publication No. WO 01/14375 to AstraZeneca AB relates to imidazo[1,2-a]pyridine and pyrazolo[2,3-a]pyridine derivatives of formula (I)

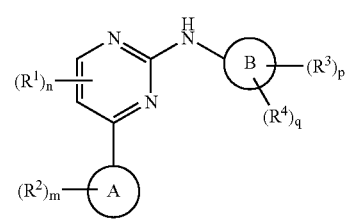

wherein Ring A is a imidazo[1,2-a]pyridine or pyrazolo[2,3-a]pyrid-3-yl; $R^2$ is as defined therein, m is 0–5; wherein the values of $R^2$ may be the same or different; $R^1$ is as defined therein; n is 0 to 2, wherein the values of $R^1$ may be the same or different; Ring B is phenyl or phenyl fused to a $C_{5-7}$cycloalkyl ring; $R^3$ is as defined therein; p is 0–4; wherein the values of $R^3$ may be the same or different; $R^4$ is as defined therein; q is 0–2; wherin the values of $R^4$ may be the same or different; and whrein p+q≦5; or a pharmaceutically aceptable salt or an in vivo hydrolysable ester thereof. The use of the compounds of formula (I) in the inhibition of cell cycle kinases CDK2, CDK4 and CDK6 are also described.

U.S. Pat. No. 5,498,774 and European Patent No. 0 404 190 to Mitsudera et al., relates to condensed heterocyclic compounds of the general formula (I):

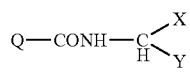

wherein Q is a condensed heterocyclic group having:-a nitrogen atom in the bridgehead which is unsubstituted or substituted, X is a hydrogen atom or a group attached through C, O, S or N, and Y is an electron attractive group; or its salt which is useful as an agricultural chemical.

BRIEF SUMMARY OF THE INVENTION

According to a first aspect of the invention there is provided a compound of formula (I):

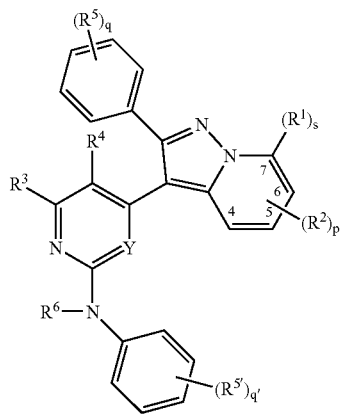

wherein:
s is 0 or 1;
p is 0, 1, 2 or 3;
$R^1$ and $R^2$ are the same or different and are each independently selected from the group consisting of halo, alkyl, alkenyl, alkynyl, cycloalkyl, cycloalkenyl, $-R^{10}$cycloalkyl, $-NR^7R^8$, Ay, $-NHR^{10}$Ay, $-NR^7$Ay, Het, $-$NHHet, $-$NHR$^{10}$Het, $-R^{10}$Ay, $-R^{10}$Het, $-OR^7$, $-$OAy, $-$OHet, $-OR^{10}$Ay, $-OR^{10}$Het, $-R^{10}OR^9$, $-R^{10}NR^7R^8$, $-R^{10}NR^7$Ay, $-R^{10}C(O)R^9$, $-C(O)R^9$, $-C(O)$Ay, $-C(O)$Het, $-CO_2R^9$, $-R^{10}C_2R^9$, $-C(O)NR^7R^8$, $-C(O)NR^7$Ay, $-C(O)NHR^{10}$Het, $-R^{10}C(O)NR^9R^{11}$, $-C(S)NR^9R^{11}$, $-R^{10}C(S)NR^9R^{11}$, $-R^{10}NHC(NH)NR^9R^{11}$, $-C(NH)NR^7R^8$, $-C(NH)NR^7$Ay, $-R^{10}C(NH)NR^9R^{11}$, $-S(O)_2NR^7R^8$, $-S(O)_2NR^7$Ay, $-R^{10}SO_2NHCOR^9_{1}$, $-R^{10}SO_2NR^9R^{11}_{1}$, $-R^{10}SO_2R^9$, $-S(O)_nR^9$, cyano, azido and nitro; or two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

wherein when s is 0, p is 1, 2 or 3 and at least one $R^2$ is selected from the group consisting of $-NR^7R^8$, $-$NHR$^{10}$Ay, $-NR^7$Ay, $-$NH Het, and $-$NHR$^{10}$Het;

each $R^7$ and $R^1$ are the same or different and are each independently selected from the group consisting of H, alkyl, cycloalkyl, alkenyl, cycloalkenyl, $-R^{10}$cycloalkyl, $-OR^9$, $-R^{10}OR^9$, $-NR^9R^{11}$, $-R^{10}NR^9R^{11}$, $-R^{10}C(O)R^9$, $-C(O)R^9$, $-CO_2R^9$, $-R^{10}CO_2R^9$, $-C(O)NR^9R^{11}$, $-R^{10}C(O)NR^9R^{11}$, $-C(S)NR^9R^{11}$, $-R^{10}C(S)NR^9R^{11}$, $-R^{10}NHC(NH)NR^9R^{11}_{1}-R^{10}C(NH)NR^9R^{11}$, $-C(NH)NR^9R^{11}$, $-SO_2NR^9R^{11}$, $-R^{10}SO_2NR^9R^{11}$, $-R^{10}NHSO_2R^9$, $-SO_2R^{10}$, $-R^{10}SO_2R^{10}$, $-R^{10}NHCOR^9$, and $-R^{11}SO_2NHCOR^9$;

each $R^9$ and $R^{11}$ are the same or different and are each independently selected from the group consisting of H, alkyl, cycloalkyl, $-R^{10}$cycloalkyl, $-R^{10}OH$, $-R^{101}OR^{10}$, and $-R^{10}NR^{10}R^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

$R^3$ and $R^4$ are the same or different and are each independently selected from the group consisting of H, halo, alkyl, cycloalkyl, alkenyl, $-OR^7$, $-R^{10}OR^7$, $-R^{10}$OAy, $-NR^7R^8$, $-R^{10}NR^7R^8$, $-C(O)R^7$, C(O)Ay, $-CO_2R^7$, $-CO_2$Ay, $-SO_2NHR^9$, Ay, $-$OAy, $-NR^7$Ay, $-R^{11}NR^7$Ay, Het, $-$NHHet, and $-$NHR$^{10}$Het;

$R^6$ is selected from the group consisting of H, alkyl, cycloalkyl, alkenyl, cycloalkenyl, $-R^{10}$cycloalkyl, $-R^{10}OR^9$, $-R^{10}NR^9R^{11}$, $-R^{10}C(O)R^9$, $-C(O)R^9$, $-CO_2R^9$, $-R^{10}CO_2R^9$, $-C(O)NR^9R^{11}$, $-R^{10}C(O)NR^9R^{11}$, $-C(S)NR^9R^{11}$, $-R^{10}C(S)NR^9R^{11}$, $-R^{10}NHC(NH)NR^9R^{11}$, $-R^{10}C(NH)NR^9R^{R11}$, $-C(NH)NR^9R^{11}$, $-SO_2NR^9R^{11}$, $-R^{10}SO_2NR^9R^{11}$, $-R^{10}NHSO_2R^9$, $-SO_2R^{10}$, $-R^{10}SO_2R^{10}$, $-R^{10}NHCOR^9$, and $-R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, $-R^{10}$cycloalkyl, $-NR^7R^8$, Ay, $-$NHR$^{10}$Ay, $-NR^7$Ay, Het, $-$NHHet, $-$NHR$^{10}$Het, $-OR^7$, $-$OAy, $-$OHet, $-R^{10}OR^9$, $-R^{10}NR^7R^8$, $-R^{10}NR^7$Ay, $-R^{10}C(O)R^9$, $-C(O)$Ay, $-C(O)$Het, $-CO_2R^9$, $-R^{10}CO_2R^9$, $-C(O)NR^7R^8$, $-C(O)NR^7$Ay, $-C(O)$NHR$^{10}$Het, $-R^{10}C(O)NR^9R^{11}$, $-C(S)NR^9R^{11}$, $-R^{10}C(S)NR^9R^{11}$, $-R^{10}NHC(NH)NR^9R^{11}$, $-C(NH)NR^7R^8$, $-C(NH)NR^7$Ay, $-R^{10}C(NH)NR^9R^{11}$, $-S(O)_2NR^7R^8$, $-S(O)_2NR^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$ cyano, azido and nitro; or two adjacent R$^5$ or R$^{5'}$ groups together with the atoms to which they are bonded form a 5- or 6-membered cycloalkyl, aryl, heterocyclic group containing 1 or 2 heteroatoms, or heteroaryl group containing 1 or 2 heteroatoms; and pharmaceutically acceptable salts, solvates and physiologically functional derivatives thereof.

According to a second aspect, the present invention provides a pharmaceutical composition comprising a compound of formula (I). The pharmaceutical composition may further comprise a pharmaceutically acceptable carrier or diluent.

According to a third aspect, the present invention provides a method for the prophylaxis or treatment of herpes viral infections in an animal. The, method comprises administering to the animal a therapeutically effective amount of a compound of formula (I) wherein:

s is 0 or 1;

p is 0,1, 2 or 3;

R$^1$ and R$^2$ are the same or different and are each independently selected from the group consisting of halo, alkyl, alkenyl, alkynyl, cycloalkyl, cycloalkenyl, —R$^{10}$cycloalkyl, —NR$^7$R$^8$, Ay, —NHR$^{10}$Ay, —NR$^7$Ay, Het, —NHHet, —NHR$^{10}$Het, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{11}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^2$ groups together with the atoms to which they are bonded form a 5- or 6-membered cycloalkyl or heterocyclic group containing 1 or 2 heteroatoms; or R$^2$ is in the C-6 position and R$^1$ and R$^2$ together with the atoms to which they are bonded form a 5- or 6-membered cycloalkyl or heterocyclic group containing 1 or 2 heteroatoms;

each R$^7$ and R$^8$ are the same or different and are each independently selected from the group consisting of H, alkyl, cycloalkyl, alkenyl, cycloalkenyl, —R$^{10}$cycloalkyl, —OR$^9$, —R$^{10}$OR$^9$, —NR$^9$R$^{11}$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{101}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

each R$^9$ and R$^{11}$ are the same or different and are each independently selected from the group consisting of H, alkyl, cycloalkyl, —R$^{10}$cycloalkyl, —R$^{10}$OH, —R$^{10}$OR$^{10}$, and —R$^{10}$NR$^{10}$R$^{10}$;

each R$^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

R$^3$ and R$^4$ are the same or different and are each independently-selected from the group consisting of H, halo, alkyl, cycloalkyl, alkenyl, —OR$^7$, —R$^{10}$OR$^7$, —R$^{10}$OAy, —NR$^7$R$^8$, —R$^{10}$NR$^7$R$^8$, —C(O)R$^7$, C(O)Ay, —CO$_2$R$^7$, —CO$_2$Ay, —SO$_2$NHR$^9$, Ay, —OAy, —NR$^7$Ay, —R$^{10}$NR$^7$Ay, Het, —NHHet, and —NHR$^{10}$Het;

R$^6$ is selected from the group consisting of H, alkyl, cycloalkyl, alkenyl, cycloalkenyl, —R$^{10}$cycloalkyl, —R$^{10}$OR$^9$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

q and q' are the same or different and are each independently selected from the group consisting of 0, 1, 2, 3, 4 and 5;

each R$^5$ and R$^{5'}$ are the same or different and are each independently selected from the group consisting of halo, alkyl, alkenyl, alkynyl, cycloalkyl, cycloalkenyl, —R$^{10}$cycloalkyl, —NR$^7$R$^8$, Ay, —NHR$^{10}$Ay, —NR$^7$Ay, Het, —NHHet, —NHR$^{10}$Het, —OR$^7$, —OAy, —OHet, —R$^{10}$OR$^9$, —R$^{10}$NR$^7$R$^8$, —R$^{10}$NR$^7$Ay, —R$^{10}$C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ or R$^{5'}$ groups together with the atoms to which they are bonded form a 5- or 6-membered cycloalkyl, aryl, heterocyclic group containing 1 or 2 heteroatoms, or heteroaryl group containing 1 or 2 heteroatoms;

or a pharmaceutically acceptable salt, solvate or physiologically functional derivative thereof. The herpes viral infection may be herpes simplex virus 1, herpes simplex virus 2, cytomegalovirus, Epstein Barr Virus, herpes zoster virus, human herpes virus 6, human herpes virus 7 and human herpes virus 8.

According to a fourth aspect, the present invention provides a method for the prophylaxis or treatment of conditions or diseases associated with herpes viral infection in an animal, comprising administering to the animal a therapeutically effective amount of a compound of formula (I).

According to a fifth aspect, the present invention provides a process for preparing compounds of formula (I) wherein Y is N. R$^3$ is H and R$^4$ is H. The process comprises reacting the compound of formula (IX):

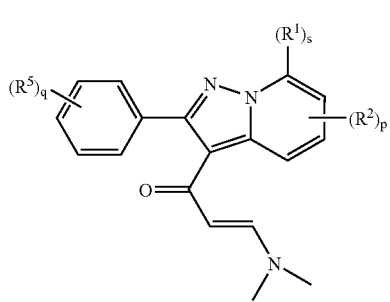

IX with a compound of formula (X):

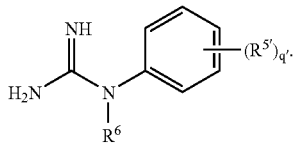

According to another aspect, the present invention provides a process for preparing compounds of formula (I) wherein Y is N; R³ is selected from the group consisting of H, alkyl, cycloalkyl, alkenyl, —R¹⁰OR⁷, —NR⁷R⁸ where R⁷ and R⁸ are not H, —R¹⁰NR⁷R⁸, —C(O)R⁷, —CO₂R⁷, —SO₂NHR⁹, Ay, and Het and R⁴ is H. The process comprises reacting a compound of formula (XV):

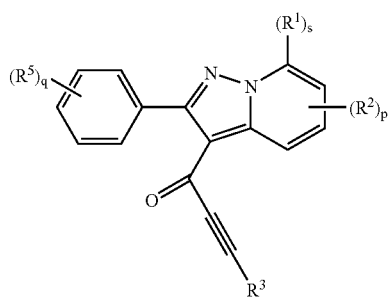

with a compound of formula (X):

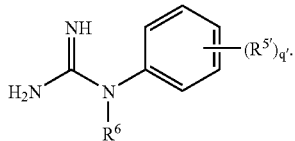

According to another aspect, the present invention provides a process for preparing compounds of formula (I) wherein Y is N. The process comprises reacting a compound of formula (XVIII):

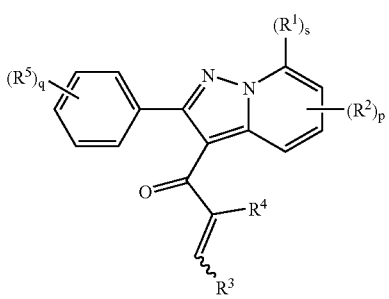

with a compound of formula (X):

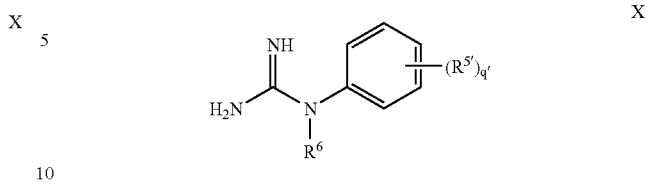

followed by oxidative aromatization.

In another aspect, the present invention provides a radiolabeled compound of formula (I) or a salt, solvate or physiologically functional derivative thereof. In one embodiment, the present invention provides a tritiated compound of formula (I) or a salt, solvate or physiologically functional derivative thereof.

In another aspect, the present invention provides a compound of formula (I) for use in therapy.

In yet another aspect, the present invention provides a compound of formula (I) for use in the prophylaxis or treatment of herpes viral infections.

In another aspect, the present invention provides a pharmaceutical composition for use in the prophylaxis or treatment of herpes viral infections, comprising a compound of formula (I).

In yet another aspect, the present invention provides a compound of formula (I) for use in the prophylaxis or treatment of conditions or diseases associated with herpes viral infections in an animal.

In yet another aspect, the present invention provides a pharmacuetical composition for use in the prophylaxis or treatment of conditions or diseases associated with herpes viral infections in an animal, comprising a compound of formula (I).

In yet another aspect, the present invention provides the use of a compound of formula (I) for the preparation of a medicament for the prophylaxis or treatment of herpes viral infections in animals.

In yet another aspect, the present invention provides the use of a compound of formula (I) for the preparation of a medicament for the treatment or prophylaxis of conditions or diseases associated with herpes viral infections in animals, preferably humans.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as compounds of formula (IX) (XV) and (XVIII), the phrase "a compound of formula (number)" means a compound having that formula and pharmaceutically acceptable salts, solvates and physiologically functional derivatives thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted with mercapto, nitro, cyano, and halo. Trihalomethyl, such as trifluoromethyl is one particularly preferred alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted with substituents selected from the group consisting of mercapto, nitro, cyano, halo, and alkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may be optionally substituted with mercapto, nitro, cyano, halo, and alkyl.

As used herein, the term "cycloalkenyl" refers to a non-aromatic carbocyclic ring having from 3 to 8 carbon atoms and up to 3 carbon-carbon double bonds. "Cycloalkenyl" includes by way of example cyclobutenyl, cyclopentenyl and cyclohexenyl. "Cycloalkenyl" also includes substituted cycloalkenyl. The ring may be optionally substituted with substituents selected from the group consisting of mercapto, nitro, cyano, halo, and alkyl.

As used herein, the term "alkynyl" refers to straight or branched, hydrocarbon chains containing from 2 to 8 carbon atoms and at least one and up to three carbon-carbon triple bonds. Examples of "alkynyl" as used herein include, but are not limited to ethynyl and propynyl. The alkynyl groups may be optionally substituted on an available carbon with mercapto, nitro, cyano, and halo.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl rings may be optionally substituted with substituents selected from the group consisting of halo, alkyl, alkenyl, cycloalkyl, cycloalkenyl, perfluoroalkyl, alkoxy, amino, hydroxy, alkylhydroxy, alkylamine, alkylether carboxy, carboxamide, sulfonamide, Het, amidine, cyano, nitro and azido. Preferred aryl groups according to the invention include but are not limited to phenyl and substituted phenyl.

The term "heterocyclic" refers to monocyclic saturated or unsaturated non-aromatic carbocyclic groups and fused bicyclic non-aromatic carbocyclic groups, having the specified number of members in a single ring and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic group may be optionally substituted with substituents selected from the group consisting of halo, alkyl, alkenyl, cycloalkyl, cycloalkenyl, perfluoroalkyl, alkoxy, amino, hydroxy, alkylhydroxy, alkylamine alkylether, carboxy, carboxamide, sulfonamide, Het, amidine, cyano, nitro and azido. Preferred heterocyclic groups according to the invention include but are not limited to substituted and unsubstituted pyrrolidine, piperidine, morpholine, thiomorpholine and piperazine.

The term "heteroaryl" refers to aromatic monocyclic heterocyclic groups and aromatic fused bicyclic groups having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may be optionally substituted with substituents selected from the group consisting of halo, alkyl, alkenyl, cycloalkyl, cycloalkenyl, perfluoroalkyl, alkoxy, amino, hydroxy, alkylhydroxy, alkylamine, alkylether, carboxy, carboxamide, sulfonamide, Het, amidine, cyano, nitro and azido. Preferred heteroaryl groups according to the invention include but are not limited to substituted and unsubstituted pyridine, furan, thiophene, pyrrole, imidazole, pyrazole, and pyrimidine.

As used herein, the term "optionally" means that the subsequently described event(s) may or may not occur, and includes both event(s) that occur and events that do not occur.

The present invention provides compounds of formula (I):

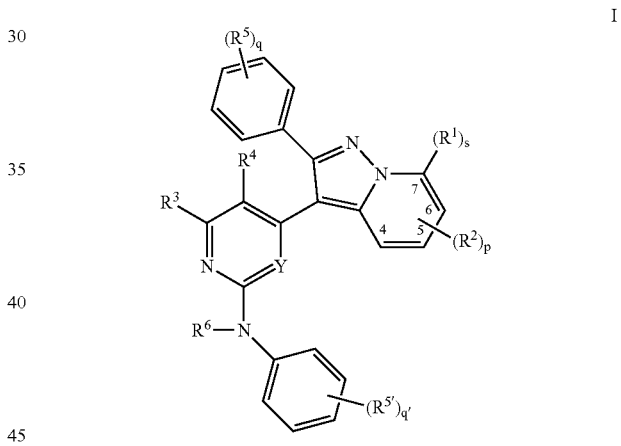

I wherein:

s is 0 or 1;

p is 0, 1, 2 or 3;

$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —$NHR^{10}$Het, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)$ $R^9$, —$C(O)R^9$, —C(O)Ay, —C(O)Het, —$CO_2R^9$, —$R^{10}CO_2R^9$, —$C(O)NR^7R^8$, —$C(O)NR^7$Ay, —C(O) NHR$^{10}$Het, —$R^{10}C(O)NR^9R^{11}$, —$C(S)NR^9R^{11}$, —$R^{10}C$ $(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, cyano, azido and nitro; or two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

each $R^7$ and $R^8$ are the same or different and are each independently selected from the group consisting of H, alkyl, cycloalkyl, alkenyl, cycloalkenyl, —$R^{10}$cycloalkyl, —$OR^9$, —$R^{10}OR^9$, —$NR^9R^{11}$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{101}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

each $R^9$ and $R^{11}$ are the same or different and are each independently selected from the group consisting of H, alkyl, cycloalkyl, —$R^{10}$cycloalkyl, —$R^{10}OH$, —$R^{10}OR^{10}$, and —$R^{10}NR^{10}R^{10}$;

each $R^{10}$ is the same or different and is independently selected from the group consisting of alkyl, cycloalkyl, alkenyl, cycloalkenyl, and alkynyl;

Ay is aryl;

Het is a 5- or 6membered heterocyclic or heteroaryl group;

n is 0, 1 or 2;

Y is N or CH;

$R^3$ and $R^4$ are the same or different and are each independently-selected from the group consisting of H, halo, alkyl, cycloalkyl, alkenyl, —$OR^7$, —$R^{10}OR^7$, —$R^{10}OAy$, —$NR^7R^8$, —$R^{10}NR^7R^8$, —$C(O)R^7$, $C(O)Ay$, —$CO_2R^7$, —$CO_2Ay$, —$SO_2NHR^9$, Ay, —$OAy$, —$NR^7Ay$, —$R^{10}NR^7Ay$, Het, —NHHet, and —$NHR^{10}$Het;

$R^6$ is selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}Ay$, —$NR^7Ay$, Het, —NHHet, —$NHR^{10}$Het, —$OR^7$, —$OAy$, —OHet, —$R^{10}OR^9$, —$R^{10}NR^7R^8$, —$R^{10}NR^7Ay$, —$R^{10}C(O)R^9$, —$C(O)Ay$, —$C(O)$Het, —$CO_2R^9$, —$R^{10}CO_2R^9$, —$C(O)NR^7R^8$, —$C(O)NR^7Ay$, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms, or heteroaryl group containing 1 or 2 heteroatoms;

pharmaceutically acceptable salts, solvates and physiologically functional derivatives thereof.

In one preferred embodiment of the compounds of formula (I), s is 1.

In one preferred embodiment of the compounds of formula (I), p is 0. In another preferred embodiment p is 1.

$R^2$ can be at the C-4, C-5 and/or C-6 position of the pyrazolopyridine ring.

In one embodiment, compounds of formula (I) are defined where one or both of $R^1$ and $R^2$ contains an aryl, heterocyclic or heteroaryl moiety (e.g., $R^1$ or $R^2$ is selected from the group consisting of Ay, —$NHR^{10}Ay$, —$NR^7Ay$, Het, —NH-Het, —$NHR^{10}$Het, —$R^{10}Ay$, —$R^{10}$Het, —OAy, —OHet, —$OR^{10}Ay$, —$OR^{10}$Het, —$R^{10}NR^7Ay$, —$C(O)Ay$, —$C(O)$Het, —$C(O)NR^7Ay$, —$C(O)NHR^{10}$Het, —$C(NH)NR^7Ay$ and $S(O)_2NR^7Ay$, or any subset thereof). In another embodiment, compounds of formula (I) are defined where one or both of $R^1$ and $R^2$ contains a heterocyclic or heteroaryl moiety (e.g., $R^1$ or $R^2$ is selected from the group consisting of Het, —NHHet, —$NHR^{10}$Het, —$R^{10}$Het, —OHet, —$OR^{10}$Het, —$C(O)$Het and —$C(O)NHR^{10}$Het, or any subset thereof). In yet another embodiment, the compounds of formula (I) are defined where neither $R^1$ nor $R^2$ contains an aryl, heterocyclic or heteroaryl moiety (e.g., $R^1$ and $R^2$ are each the same or different and are each independently selected from the group consisting of halo, alkyl, alkenyl, alkynyl, cycloalkyl, cycloalkenyl, —$R^{10}$cycloalkyl, —$NR^7R^8$, —$OR^7$, $R^{10}OR^9$, $R^{10}NR^7R^8$, —$R^{10}C(O)R^9$, —$C(O)R^9$, —$CO_2R^9$, —$R^{10}CO_2R^9$, —$C(O)NR^7R^8$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$R^{10}C(NH)NR^9R^{11}$, —$S(O)_2NR^7R^8$, —$R^{10}SO_2NHCOR^9$, —$R^{10}SO_2NR^9R^{11}$, —$R^{10}SO_2R^9$, —$S(O)_nR^9$, cyano, azido and nitro, or any subset thereof). In another embodiment, neither $R^1$ nor $R^2$ contains a heteroaryl or heterocyclic moiety but may contain an aryl moeity (e.g., $R^1$ or $R^2$ is selected from the group consisting of halo, alkyl, alkenyl, alkynyl, cycloalkyl, cycloalkenyl, —$R^{10}$cycloalkyl, —$NR^7R^8$, Ay, —$NHR^{10}Ay$, —$NR^7Ay$, —$OR^7$, —$R^{10}Ay$, —OAy, —$OR^{10}Ay$, —$R^{10}OR^9$, —$R^{10}NR^7Ay$, —$R^{10}C(O)R^9$, —$C(O)R^9$, —$C(O)Ay$, —$CO_2R^9$, —$R^{10}CO_2R^9$, —$C(O)NR^7R^8$, —$C(O)NR^7Ay$, —$R^{10}C(O)NR^9R^{11}$, —$C(S)NR^9R^{11}$, —$R^{10}C(S)NR^9R^{111}$, —$R^{10}NHC(NH)NR^9R^9$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{11}$, —$R^{10}SO_2R^9$, —$S(O)_nR^9$, cyano, azido and nitro, or any subset thereof).

One class of compounds of formula (I) includes those compounds defined wherein two adjacent $R^2$ groups together with the carbon atoms to which they are bonded form a 5- or 6-membered cycloalkyl or a 5- or 6-membered heterocyclic group containing 1 or 2 heteroatoms; or p is 1 or more, $R^2$ is in the C-6 position and $R^1$ and $R^2$ together with the carbon atoms to which they are bonded form a 5- or 6-membered cycloalkyl or a 5- or 6-membered heterocyclic group containing 1 or 2 heteroatoms. By "two adjacent groups" is meant that two $R^2$ groups are bonded to adjacent carbon atoms. When two adjacent $R^2$ groups together with the carbon atoms to which they are bonded form a 5- or 6-membered cycloalkyl or a 5- or 6-membered heterocyclic group having 1 or 2 heteroatoms or $R^1$ and C-6 $R^2$ together with the carbon atoms to which they are bonded form a 5- or 6-membered cycloalkyl or a 5- or 6-membered heterocyclic group having 1 or 2 heteroatoms, each $R^2$ group or each $R^1$ and $R^2$ group may be the same or different and is preferably selected from the group consisting of alkyl, —$OR^7$, —$NR^7R^8{}_1$ and —$S(O)_nR^9$. For example, in one embodiment two adjacent $R^2$ groups (or $R^1$ and C-6 $R^2$) are —OR$^7$ and together with the carbon atoms to which they are bonded, they form a heterocyclic group such as:

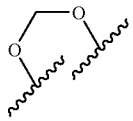

In another embodiment, two adjacent R$^2$ groups (or R$^1$ and C-6 R$^2$) are alkyl and together with the carbon atoms to which they are bonded, they form a cycloalkyl group such as:

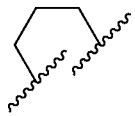

In another embodiment two adjacent R$^2$ groups (or R$^1$ and C-6 R$^2$) are defined as —OR$^7$ and —NR$^7$R$^8$ respectively and together with the carbon atoms to which they are bonded, they form a heterocyclic group such as:

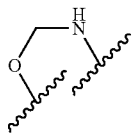

In another embodiment two adjacent R$^2$ groups (or R$^1$ and C-6 R$^2$) are defined as —S(O)$_n$R$^9$ and —NR$^7$R$^8$ respectively and together with the carbon atoms to which they are bonded, they form a heterocyclic group such as:

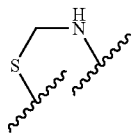

From these examples, additional embodiments can be readily ascertained by those skilled in the art.

Preferably, two adjacent R$^2$ groups together with the carbon atoms to which they are bonded do not form a 5- or 6-membered cycloalkyl or a 5- or 6-membered heterocyclic group containing 1 or 2 heteroatoms. In another preferred embodiment, R$^1$ and R$^2$ together with the carbon atoms to which they are bonded do not form a 5- or 6-membered cycloalkyl or a 5- or 6-membered heterocyclic group containing 1 or 2 heteroatoms.

Preferably, R$^1$ is selected from the group consisting of halo, alkyl, cycloalkyl, —R$^{10}$cycloalkyl, —NR$^7$R$^8$, Ay, —NHR$^{10}$Ay, —NR$^7$Ay, Het, —NHHet, —NHR$^{10}$Het, —OR$^7$, —OAy, —OHet, —R$^{10}$OR$^9$, —R$^{10}$NR$^7$R$^8$, —C(O)R$^9$, —CO$_2$R$^9$, —C(O)NR$^7$R$^8$, —S(O)$_n$R$^9$, cyano, azido and nitro, or any subset thereof. More preferably, R$^1$ is selected from the group consisting of halo, alkyl, —NR$^7$R$^8$, —NR$^7$Ay, Het, —NHHet, —NHR$^{10}$Het, —OR$^7$, —C(O)NR$^7$R$^8$ and S(O)$_n$R$^9$, or any subset thereof. The variable n is preferably 0.

In one preferred embodiment, R$^1$ is selected from the group consisting of halo, alkyl, —NH$_2$, —NH-alkyl, —NH-cycloalkyl, —N(alkyl)(alkyl), Het, —O-alkyl, —N(alkyl)-O-alkyl, —NHAy, —C(O)NH$_2$, —C(O)NH(alkyl), —C(O)N(alkyl)(alkyl) and —S-alkyl, or any subset thereof. More preferably, R$^1$ is selected from the group consisting of —NH-alkyl, —NH-cycloalkyl and pyrrolidone or any subset thereof.

Specific examples of some preferred R$^1$ groups are selected from the group consisting of Cl, methyl, ethyl, propyl, isopropyl, butyl, isobutyl, —NH$_2$, —NH-methyl, —N(CH$_3$)$_2$, —NH-cyclopentyl, —NH-cyclopropyl, —NH-isopropyl, —NH-butyl, —NH-phenyl, —N(CH$_2$)$_2$OCH$_3$, pyrrolidine, methoxy, ethoxy, propoxy, isopropoxy, butoxy, thiomethoxy, thioethoxy, thioisopropoxy, and pyrrolidine, or any subset thereof.

When p is 1 or more, preferably each R$^2$ is the same or different and is independently selected from the group consisting of halo, alkyl, —OR$^7$, —R$^{10}$OR$^9$, —NR$^7$R$^8$, C(O)Het, —CO$_2$R$^9$, —C(O)NR$^7$R$^8$, Ay, —OAy, —NR$^7$Ay, —NHR$^{10}$Ay, —C(O)NR$^7$Ay, Het, —C(O)NHR$^{10}$Het, —NHHet, —NHR$^{10}$Het, —S(O)$_n$R$^9$, cyano, azido and nitro. More preferably, each R$^2$ is the same or different and is independently selected from the group consisting of halo, alkyl, —NR$^7$R$^8$, —NR$^7$Ay, —NHHet and —C(O)NR$^7$R$^8$. In one embodiment, R$^2$ is halo.

According to one particularly preferred embodiment, when s is 0, p is 1, 2 or 3 and at least one R$^2$ is selected from the group consisting of —NR$^7$R$^8$, —NHR$^{10}$Ay, —NR$^7$Ay, —NHHet, and —NHR$^{10}$Het.

Specific examples of some preferred R$^2$ groups are selected from the group consisting of F, Cl, Br, methyl, ethyl, propyl, isopropyl, butyl, isobutyl, —NH$_2$, —NH-methyl, —N(CH$_3$)$_2$, —NHCH(CH$_3$)$_2$, —NH-cyclopentyl, —NH-cyclopropyl, —NH-isopropyl, —NH-phenyl, —NH(CH$_2$)$_2$OCH$_3$, —NH—SO$_2$CH$_3$, pyrrolidine, methoxy, ethoxy, propoxy, isopropoxy, butoxy, thiomethoxy, thioethoxy, —CF$_3$, azido and nitro, or any subset thereof.

In one class of compounds of formula (I), Y is CH. In another preferred class of compounds of formula (I), Y is N.

Preferably, R$^7$ and R$^9$ are each the same or different and are each independently selected from the group consisting of H, alkyl, cycloalkyl, —R$^{10}$-cycloalkyl, —R$^{10}$OR$^9$, —R$^{10}$NR$^9$R$^{11}$, —C(O)R$^9$, and —R$^{10}$CO$_2$R$^9$, or any subset thereof. More preferably, R$^7$ and R$^8$ are each the same or different and are each independently selected from the group consisting of H, alkyl, cycloalkyl, and —R$^{10}$-cycloalkyl, or any subset thereof. In one embodiment, R$^7$ and R$^8$ are each the same or different and are each independently selected from the group consisting of H, alkyl and cycloalkyl.

Preferably R$^9$ and R$^{11}$ are each the same or different and are each independently selected from the group consisting of H, alkyl, cycloalkyl, and —R$^{10}$-cycloalkyl, or any subset thereof. More preferably, R$^9$ and R$^{11}$ are each the same or different and are each independently selected from the group consisting of H and alkyl.

Preferably R$^{10}$ is alkyl or cycloalkyl; more preferably alkyl.

In another embodiment, the compounds of formula (I) include those compounds defined where at least one of R$^3$ and R$^4$ contains an aryl, heterocyclic or heteroaryl moiety (or more preferably a heterocyclic or heteroaryl moiety but exclude aryl moeities). A preferred embodiment includes those compounds of formula (I) where neither R$^3$ nor R$^4$ contain an aryl, heterocyclic or heteroaryl moiety (or more preferably, neither contains a heterocyclic or heteroaryl moeity but may contain an aryl moiety). Based on the guidance given above for $R^1$ and $R^2$, one skilled in the art can readily determine the list of appropriate groups defining $R^3$ and $R^4$ which contain or exclude aryl, heterocyclic or heteroaryl moeities.

$R^3$ is preferably selected from the group consisting of H, halo, alkyl, —$OR^7$, —$R^{10}OR^7$, —$NR^7R^8$, —$R^{10}NR^7R^8$, —$CO_2R^7$ and Ay, or any subset thereof. More preferably, $R^3$ is selected from the group consisting of H, halo, alkyl, —$OR^7$, and —$NR^7R_8$, or any subset thereof. Most preferably $R^3$ is H or alkyl. In one embodiment $R^3$ is H.

$R^4$ is preferably selected from the group consisting of H, halo, alkyl, —$OR^7$, —$R^{10}OR^7$, —$NR^7R^8$, $R^{10}NR^7R$, —$CO_2R^7$ and Ay, or any subset thereof. More preferably, $R^4$ is selected from the group consisting of H, halo, alkyl, —$OR^7$, and —$NR^7R^8$, or any subset thereof. Most preferably $R^4$ is H or alkyl. In one embodiment $R^4$ is H.

Preferably, q is selected from the group consisting of 0, 1 and 2. In one embodiment, q is 0. More preferably, q is 1.

Preferably, q' is selected from the group consisting of 0, 1, 2 and 3. More preferably, q' is 0, 1 or 2. In one embodiment, q' is 1.

Each of $R^5$ and $R^{5'}$ may be independently in the ortho, meta or para position.

One class of compounds of formula (I) includes those compounds defined wherein at least one of $R^5$ and $R^{5'}$ contains an aryl, heterocyclic or heteroaryl moiety (preferably a heterocyclic or heteroaryl moiety). Another class of compounds of formula (I) includes those compounds defined wherein no $R^5$ or $R^{5'}$ contains an aryl, heterocyclic or heteroaryl moiety (preferably a heterocyclic or heteroaryl moiety). Based on the guidance given above for $R^1$ and $R^2$, one skilled in the art can readily determine the list of appropriate groups defining $R^5$ and $R^{5'}$ which contain or exclude aryl, heterocyclic or heteroaryl moeities.

Either two adjacent $R^5$ or $R^{5'}$ groups together with the carbon atoms to which they are bonded may be linked to form a 5- or 6-membered carbocyclic, a 5- or 6-membered aryl, a 5- or 6-membered heterocyclic group containing 1 or 2 heteroatoms, or a 5- or 6-membered heteroaryl group containing 1 or 2 heteroatoms. When two adjacent $R^5$ or $R^{5'}$ groups together with the carbon atoms to which they are bonded form a 5- or 6-membered cycloalkyl, aryl, heterocyclic group containing 1 or 2 heteroatoms or a heteroaryl group containing 1 or 2 heteroatoms, each $R^5$ and $R^{5'}$ is preferably selected from the group consisting of alkyl, alkenyl, —$OR^7$, —$NR^7R^8$ and —$S(O)_nR^9$. Embodiments where two adjacent $R^5$ or $R^{5'}$ groups together with the carbon atoms to which they are bonded form a 5- or 6-membered cycloalkyl or a 5- or 6-membered heterocyclic group having 1 or 2 heteroatoms (i.e., a cycloalkyl or heterocyclic ring), are analogous to those described above for the compounds wherein two $R^2$ groups or $R^1$ and C-6 $R^2$ together with the atoms to which they are bonded form a 5- or 6-membered cycloalkyl or a 5- or 6-membered heterocyclic group having 1 or 2 heteroatoms. Based on this guidance, one skilled in the art can readily ascertain embodiments wherein two adjacent $R^5$ or $R^{5'}$ groups together with the carbon atoms to which they are bonded form a a 5- or 6-membered aryl or a 5- or 6-membered heteroaryl ring containing 1 or 2 heteroatoms.

In one preferred embodiment, two adjacent $R^5$ groups together with the carbon atoms to which they are bonded do not form a 5- or 6-membered cycloalkyl, a 5- or 6-membered aryl, a 5- or 6-membered heterocyclic group containing 1 or 2 heteroatoms or a 5- or 6-membered heteroaryl group containing 1 or 2 heteroatoms. In another preferred embodiment, two adjacent $R^{5'}$ groups together with the carbon atoms to which they are bonded do not form a 5- or 6-membered cycloalkyl, a 5- or 6-membered aryl, a 5- or 6-membered heterocyclic group containing 1 or 2 heteroatoms or a 5- or 6-membered heteroaryl group containing 1 or 2 heteroatoms.

Preferably, each $R^1$ and $R^1$ are the same or different and are each independently selected from the group consisting of halo, alkyl, alkenyl, —$OR^7$, —$CO_2R^9$, —$NR^7R^8$, —$C(O)NR^7R^8$, Ay, —OAy, —$NR^7$Ay, —$NHR^{10}$Ay, —$C(O)NR^7$Ay, Het, —$S(O)_2NR^7R^8$, cyano, nitro and azido, or any subset thereof. More preferably, each $R^5$ group is the same or different and is independently selected from the group consisting of halo, alkyl, —$OR^7_1$, —$NR^7R^8$, —$C(O)NR^7R^8$, Het, —$S(O)_2NR^7R^8$, cyano, nitro, and azido, or any subset thereof. Most preferably, each $R^5$ group is the same or different and is independently selected from the group consisting of halo, alkyl, —$OR^7$, —$NR^7R^8$, cyano, nitro, and azido, or any subset thereof. In particular, preferred embodiments of the compounds of formula (I) are defined where $R^5$ is selected from the group consisting of halo (e.g., fluoro or chloro), alkyl (e.g., methyl), O-alkyl (e.g., O-methyl, O-isobutyl, and

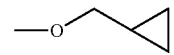

), O-allyl, cyano, —NH—$CH_3$, —$N(CH_3)_2$, nitro and azido or any subset thereof.

More preferably, each $R^{5'}$ group is the same or different and is independently selected from the group consisting of halo, alkyl, —$OR^7$, —$NR^7R^8$, —$C(O)NR^7R^8$, Het, —$S(O)_2NR^7R^8$, cyano, nitro and azido, or any subset thereof. Most preferably, each $R^{5'}$ group is the same or different and is independently selected from the group consisting of halo, alkyl, —$OR^7$, —$NR^7R^8$, cyano, nitro, and azido, or any subset thereof. In particular, preferred embodiments of the compounds of formula (I) are defined where $R^{5'}$ is selected from the group consisting of halo (e.g., fluoro or chloro), alkyl (e.g., methyl), O-alkyl (e.g., O-methyl, O-isobutyl, and

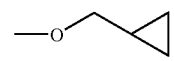

), O-allyl, cyano, —NH—$CH_3$, —$N(CH_3)_2$, nitro and azido, or any subset thereof.

Preferably, $R^6$ is selected from the group consisting of H, alkyl, cycloalkyl, —$R^{10}$cycloalkyl, —$C(O)R^9$, —$CO_2R^9$, —$C(O)NR^9R^{11}$, —$C(NH)NR^9R^{11}$, —$SO_2NR^9R^{11}$, —$R^{10}SO_2NR^9R^{11}$, —$SO_2R^{10}$ and —$R^{10}SO_2NHCOR^9$. More preferably, $R^6$ is selected from the group consisting of H, alkyl, cycloalkyl, —$R^{10}$cycloalkyl and —$C(O)R^9$. In one preferred embodiment, $R^6$ is selected from the group consisting of H, alkyl and cycloalkyl. Specific examples of preferred $R^6$ groups are selected from the group consisting of H and —$CH_3$. In one preferred embodiment, $R^6$ is H.

It is to be understood that the present invention includes all combinations and subsets of tile particular and preferred groups defined hereinabove.

Preferred compounds of formula (I) include but are not limited to:

3-(2-Anilino-4-pyrimidinyl)-N-cyclopentyl-2-(4-fluorophenyl)-pyrazolo[1,5-α]pyridin-7-amine;

N-Cyclopentyl-2-(4-fluorophenyl)-3-[2-(3,4,5-trimethoxyanilino)-4-pyrimidinyl]pyrazolo[1,5-α]pyridin-7-amine;
N-Cyclopentyl-2-(4-fluorophenyl)-3-[2-(4-methoxyanilino)-4-pyrimidinyl]pyrazolo[1,5-α]pyridin-7-amine;
N-Cyclopentyl-3-[2-(4-fluoroanilino)-4-pyrimidinyl]-2-(4-fluorophenyl)pyrazolo[1,5-α]pyridin-7-amine;
[3-({4-[7-(Cyclopentylamino)-2-(4methoxyphenyl)pyrazolo[1,5-α]pyridin-3-yl]-2-pyrimidinyl}amino)phenyl](phenyl)methanone;
N-[3-(2-Anilino-4-pyrimidinyl)-2-(4-fluorophenyl)pyrazolo[1,5-α]pyridin -5-yl]-N-cyclopentylamine;
3-(2-Anilino-4-pyrimidinyl)-5-chloro-N-cyclopentyl-2-(4-fluorophenyl)pyrazolo[1,5-α]pyridin-7-amine;
N-{4-[5—Chloro-7-(ethylsulfanyl)-2-(4-fluorophenyl)pyrazolo[1,5-α]pyridin-3-yl]-2-pyrimidinyl}-N-phenylamine;
N-Cyclopentyl-2-(4-methoxyphenyl)-3-[2-(3-nitroanilino)-4-pyrimidinyl]pyrazolo[1,5-α]pyridin-7-amine;
[3-({4-[7-(Cyclopentylamino)-2-(4-methoxyphenyl)pyrazolo[1,5-α]pyridin-3-yl]-2-pyrimidinyl}amino)phenyl]methanol;
$N^1$-{4-[7-(Cyclopentylamino)-2-(4-methoxyphenyl)pyrazolo[1,5-α]pyridin-3-yl]-2-pyrimidinyl}-1,3-benzenediamine; and
3-[2-(3-Azidoanilino)-4-pyrimidinyl]-N-cyclopentyl-2-(4-methoxyphenyl)pyrazolo[1,5-α]pyridin-7-amine; and pharmaceutically acceptable salts, solvates and physiologically functional derivatives thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV)) (including CMV in organ transplant patients being treated with immunosupressants), Epstein Barr virus (EBV), herpes zoster virus (HZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; multiple sclerosis which has been associated with herpes viral infections such as EBV and HHV-6, which have been associated with HSV-1 infection. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty, viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B and hepatitis C viruses, human papilloma virus (HPV) and HIV.

The present invention provides a method for the treatment or prophylaxis of a viral infection in an animal such as a mammal (e.g., a human), particularly a herpes viral infection, which comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of conditions or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention maybe therapeutically administered as the raw chemical, it is preferable to present the active ingredient as a pharmaceutical formulation. The pharmaceutical formulation may include one or more pharmaceutically acceptable carriers or diluents together with the compound of formula (I). The carrier(s) must be "acceptable" in the sense of being compatible with the other ingredients of the formulation and not deleterious to the recipient thereof.

Accordingly, the present invention further provides for a pharmaceutical composition or formulation comprising a compound of formula (I). In one embodiment, the pharmaceutical formulation further comprises one or more pharmaceutically acceptable carriers or dilents and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents, such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include, suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleoside reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, ganciclovir, docosanol, miribavir, amprenavir, lamivudine, zidovudine, and abacavir. Preferred antiviral agents for combining with the compounds of the present invention include aciclovir, famcyclovir and valaciclovir. Thus the present invention provides in a further aspect, a combination comprising a compound of formula (I) and an antiviral agen selected from the group consisting of aciclovir or valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art Compounds of formula (I) wherein Y is N and $R^3$ and $R^4$ are both H, may be conveniently prepared by a general process outlined in Scheme 1 below.

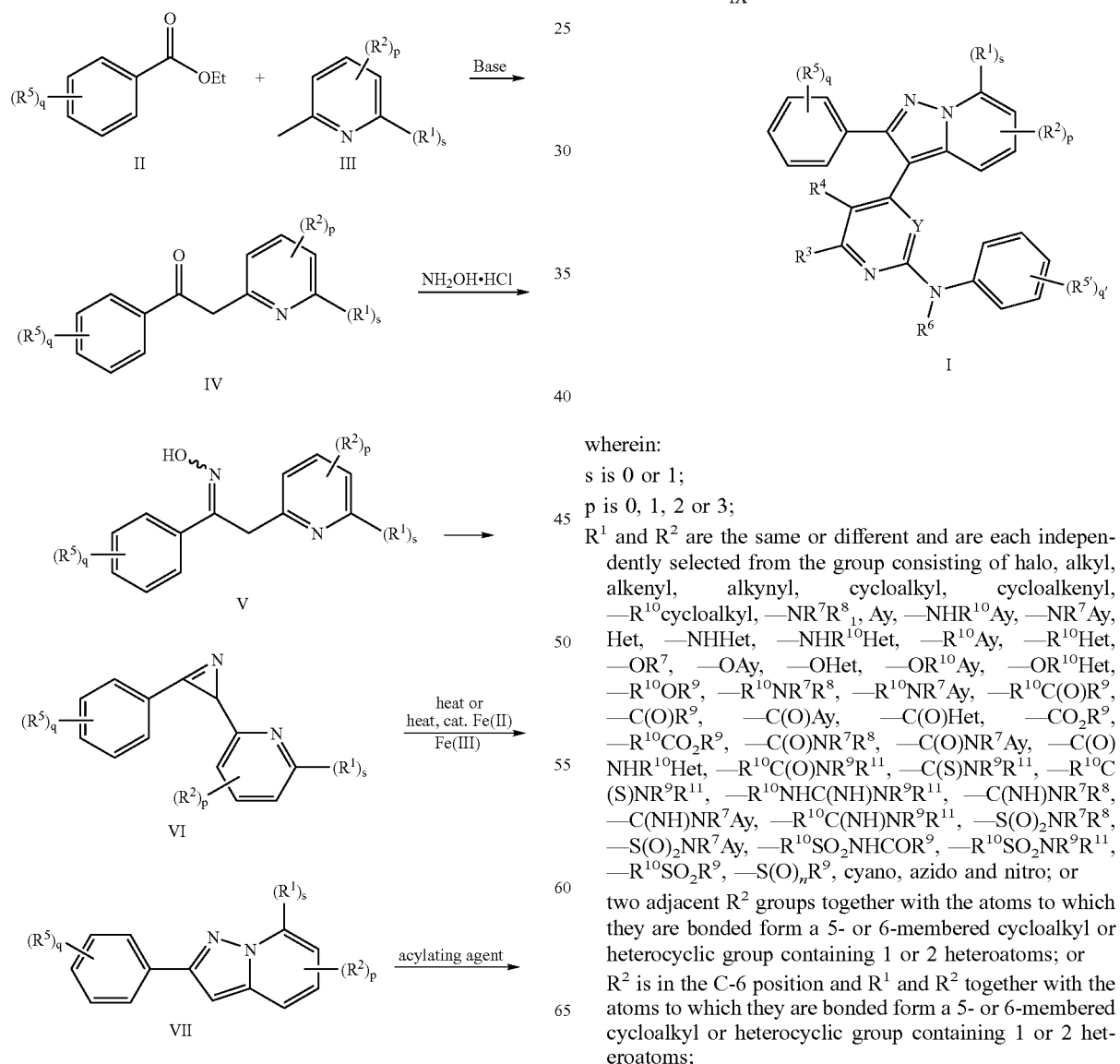

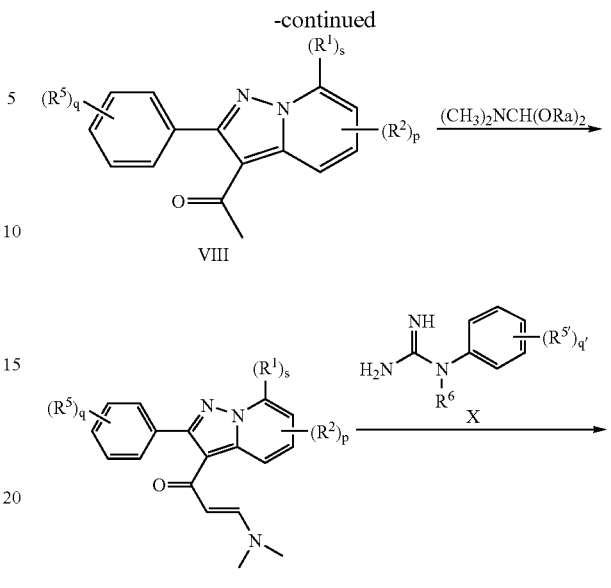

wherein:

s is 0 or 1;

p is 0, 1, 2 or 3;

$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8{}_1$, Ay, —$NHR^{10}$Ay, —$NR^7$Ay, Het, —NHHet, —$NHR^{10}$Het, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —$C(O)NR^7R^8$, —$C(O)NR^7$Ay, —C(O)NHR$^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

each $R^7$ and $R^8$ are the same or different and are each independently selected from the group consisting of H, alkyl, cycloalkyl, alkenyl, cycloalkenyl, —$R^{10}$cycloalkyl, —$OR^9$, —$R^{10}OR^9$, —$NR^9R^{11}$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

each $R^9$ and $R^{11}$ are the same or different and are each independently selected from the group consisting of H, alkyl, cycloalkyl, —$R^{10}$cycloalkyl, —$R^{10}OH$, —$R^{10}OR^{10}$, and —$R^{10}NR^{10}R^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

$R^6$ is selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}Ay$, —$NR^7Ay$, Het, —NHHet, —$NHR^{10}$Het, —$OR^7$, —OAy, —OHet, —$R^{10}OR^9$, —$R^{10}NR^7R^8$, —$R^{10}NR^7Ay$, —$R^{10}C(O)R^9$, —$C(O)R^9$, —C(O)Ay, —C(O)Het, —$CO_2R^9$, —$R^{10}CO_2R^9$, —$C(O)NR^7R^8$, —$C(O)NR^7Ay$, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms, or heteroaryl group containing 1 or 2 heteroatoms; and Ra is alkyl or cycloalkyl.

Generally, the process for preparing the compounds of formula (I) wherein Y is N and $R^3$ and $R^4$ are both H, (all formulas and all other variables having been defined above in connection with Scheme 1) comprises the steps of:

(a) reacting a picoline compound of formula (III) with a benzoylating agent of formula (II) to prepare the compound of formula (IV);

(b) reacting the compound of formula (IV) with a hydroxylamine source to prepare a compound of formula (V);

(c) reacting the compound of formula (V) with an acylating or sulfonylating agent to prepare a compound of formula (VI);

(d) rearranging the compound of formula (VI) to prepare a compound of formula (VII);

(e) acylating the compound of formula (VII) to prepare a compound of formula (VIII);

(f) reacting the compound of formula (VIII) with a dimethylformamide dialkyl acetal of formula $(CH_3)_2NCH(ORa)_2$ to prepare a compound of formula (IX); and (g) reacting the compound of formula (IX) with a compound of formula (X) to prepare the compounds of formula (I) or a pharmaceutically acceptable salt, solvate or physiologically functional derivative thereof.

More specifically, compounds of formula (I) wherein Y is N and $R^3$ and $R^4$ are both H, can be prepared by reacting a compound of formula (IX) with a compound of formula (X) to prepare a compound of formula (I) or a pharmaceutically acceptable salt, solvate or physiologically functional derivative thereof.

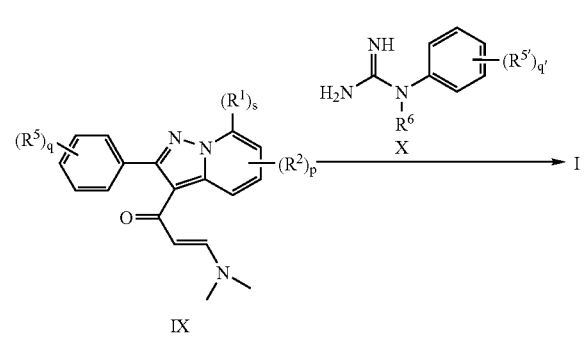

wherein all variables are as defined above in connection with Scheme 1.

This general method can be readily carried out by mixing a compound of formula (IX) with a compound of formula (X) in a suitable solvent, optionally in the presence of a base (preferably when the amidine is in a salt form), and heating the reaction to 50–150° C. Typical solvents include lower alcohols such as methanol, ethanol, isopropanol and the like and dimethylformamide, 1-methyl-2-pyrrolidinone and the like. The base is typically a sodium alkoxide, potassium carbonate, or an amine base such as triethylamine. In one embodiment, the solvent is dimethylformamide or 1-methyl-2-pyrrolidinone and the base is potassium carbonate, or an amine base such as triethylamine.

The compounds of formula (X) can be prepared according to conventional methods. One preferred method for preparing the compounds of formula (X) (adapted from WO 00/78731) involves heating an appropriately substituted aniline of the formula (XI) with cyanamide in the presence of a protic acid in an alcohol solvent.

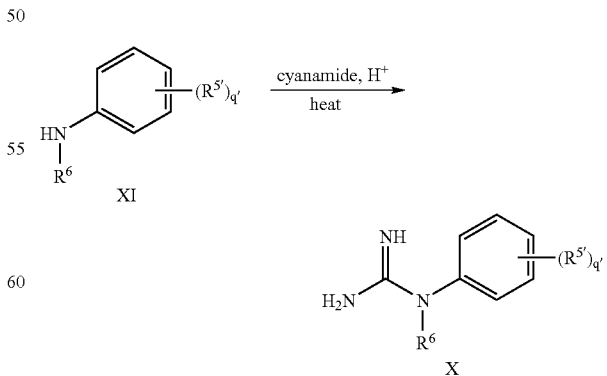

wherein all variables are as defined above in connection with Scheme 1.

This method is adapted from the procedures described in WO 00/78731 published 28 Dec. 2000, the subject matter of which is incorporated herein by reference in its entirety. Preferred acids include but are not limited to hydrochloric acid, nitric acid, and sulfuric acid. Suitable solvents will be readily apparent to those skilled in the art and include, for example, ethanol.

Compounds of the formula (IX) may be conveniently prepared by reacting a compound of formula (VIII) with a dimethylformamide dialkyl acetal, wherein $R_a$ is alkyl or cycloalkyl.

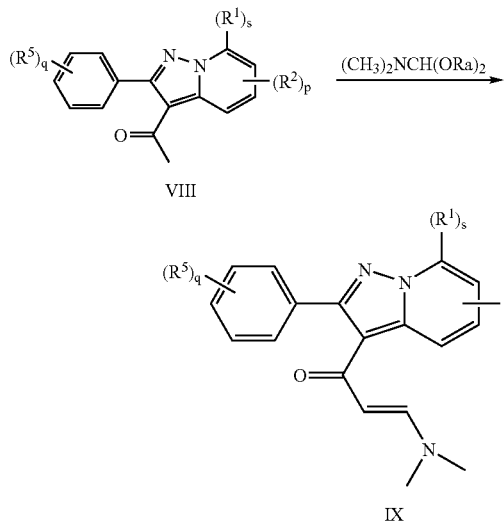

wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VIII) with the dimethylformamide dialkyl acetal, optionally with heating.

Compounds of the formula (VIII) may be conveniently prepared from compounds of the formula (VII) using an acylation procedure.

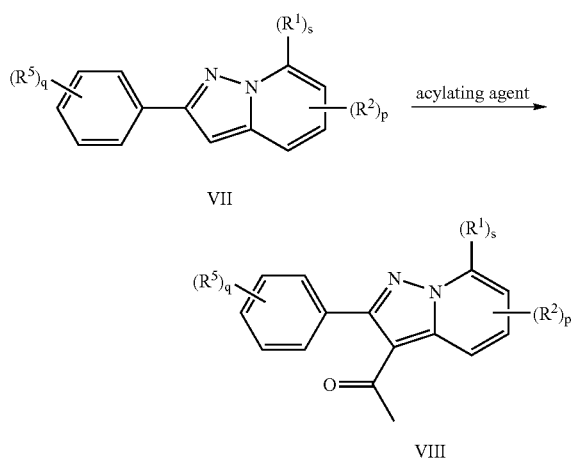

wherein all variables are as defined above in connection with Scheme 1.

Typically the acylation is carried out by treating the compounds of formula (VII) with an acylating agent, optionally in the presence of an acid or Lewis acid catalyst in an inert solvent with optional heating. Typical acylating agents will be readily determined by those skilled in the art. One preferred acylating agent is acetic anhydride. Lewis acid catalysts are also known to those skilled in the art. One preferred Lewis acid catalyst for use in this reaction is boron trifluoride diethyl etherate. A suitable solvent is toluene.

In certain embodiments of compounds of formula (I) wherein $R^1$ is selected from the group consisting of —$NR^7R^8$, —$NHR^{10}Ay$, —$NR^7Ay$, —NHHet, —$NHR^{10}$Het and Het are desired, it may be advantageous to convert a compound of formula (VIII) wherein $R^1$ is halo (i.e., compounds of formula (VIII-A)) to another compound of formula (VIII) wherein $R^1$ is an amine-linked substituent (i.e., compounds of formula (VIII-B)) before proceeding with the reaction of the compound of formula (VIII) with the dimethylformamide dialkylacetal compounds to prepare the compounds of formula (IX). A particularly useful method of converting a compound of formula (VIII-A) to a compound of formula (VIII-B) involves replacing a 7-halo with an amine.

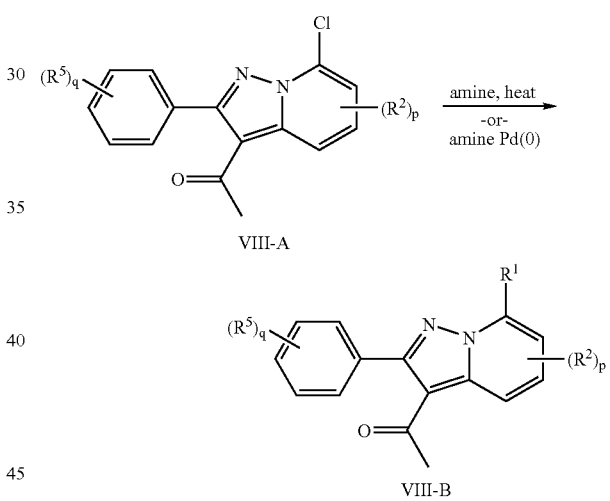

wherein $R^1$ is defined above and all other variables are as defined in connection with Scheme 1.

Typically the replacement is carried out by mixing the compound of formula (VIII-A) with an amine nucleophile of formula $R^1$ where $R^1$ is selected from the group consisting of —$NR^7R^8$, —$NHR^{10}Ay$, —$NR^7Ay$, —NHHet, —$NHR^{10}$Het and Het; and optionally heating the reaction.

The reaction can also be carried out via an adaptation of procedures found in the literature (Wolfe, J. P.; Buchwald, S. L. *J. Org. Chem.* 2000, 65, 1144) wherein a compound of the general formula (VIII-A) is treated with an amine, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

Compounds of formula (II) are conveniently prepared by rearranging an azirine compound of formula (VI).

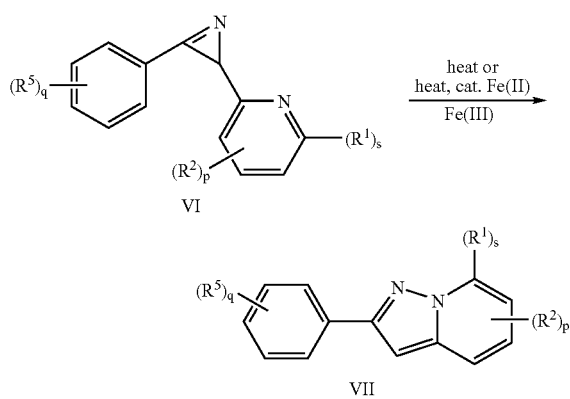

VI

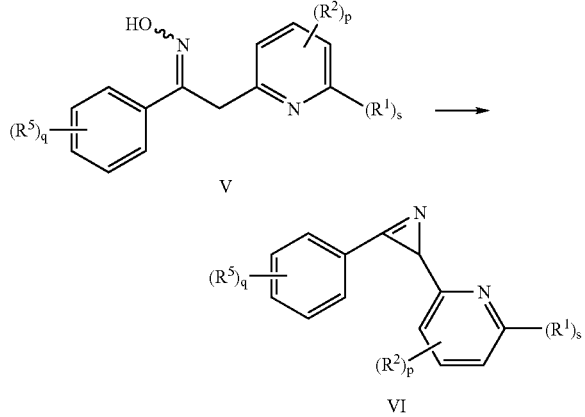

VII wherein all variables are as defined above in connection with Scheme 1.

The rearrangement of the azirines of formula (VI) can be accomplished by heating a solution of the azirine of formula (VI) in a suitable solvent at a temperature of about 160–200° C. Suitable inert solvents include, but are not limited to, 1-methyl-2-pyrrolidinone, and 1,2,4trichlorobenzene. A more preferred method for rearrangement of the azirine of formula (VI) to compounds of formula (VII) involves reacting the compound of formula (VI) with ferrous chloride ($FeCl_2$) or ferric chloride ($FeCl_3$). This reaction is typically done in an inert solvent with heating. A preferred solvent for this reaction is 1,2-dimethoxyethane and the like.

Typically the azirines of formula (VI) are prepared from oxime compounds of formula (V) by treatment with acylating or sulfonylating agents in the presence of a base.

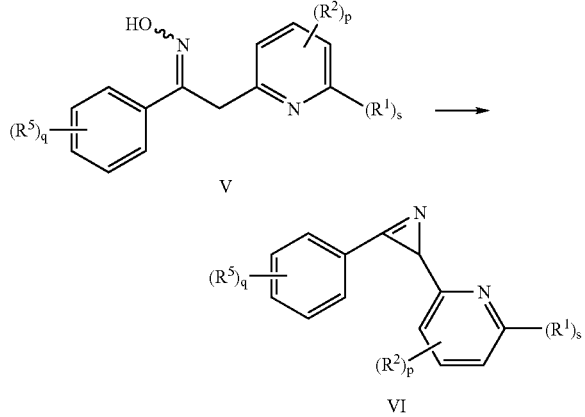

V

VI wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (V) are readily prepared by treating ketone compounds of formula (IV) with a hydroxylamine source, in a suitable solvent, and optionally with a base.

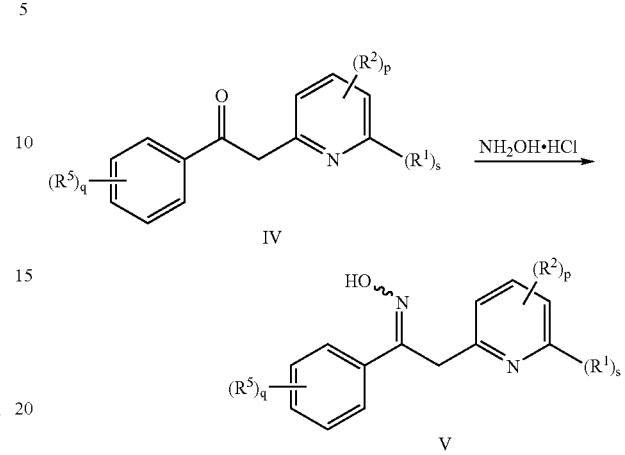

IV

V wherein all variables are as defined above in connection with Scheme 1.

Preferably the hydroxylamine is hydroxylamine hydrochloride and the base is an aqueous solution of sodium hydroxide. Suitable solvents include lower alcohols such as methanol, ethanol, or isopropanol.

The ketone compounds of formula (IV) can be prepared by treatment of a picoline compound of formula (III) with a benzoylating agent of formula (II) in the presence of a base.

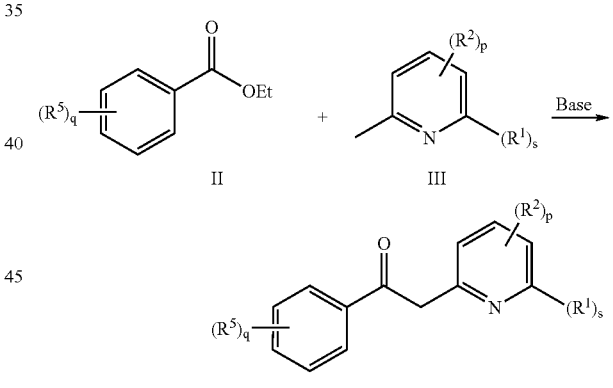

II  III

IV wherein all variables are as defined above in connection with Scheme 1.

The benzoylating agents of formula (II) and the picoline compounds of formula (III) are commercially available or may be prepared using conventional methods known to those skilled in the art. Preferred benzoylating agents of formula (II) include, but are not limited to, benzoyl esters. An example of a suitable base is lithium bis(trimethylsilyl)amide in an inert solvent such as tetrahydrofuran.

In a further embodiment of the present invention, compounds of formula (I) wherein Y is N; $R^3$ is selected from the group consisting of H, alkyl, cycloalkyl, alkenyl, —$R^{10}OR^7$, —$NR^7R^8$ (where $R^7$ and $R^8$ are not H), —$R^{10}NR^7R^8$, —$C(O)R^7$, —$CO_2R^7$, —$SO_2NHR^9$, Ay, and Het; and $R^4$ is H, and pharmacuetically acceptable salts, solvates and physiologically functional derivatives thereof, may be conveniently prepared by the process outlined in Scheme 2 below.

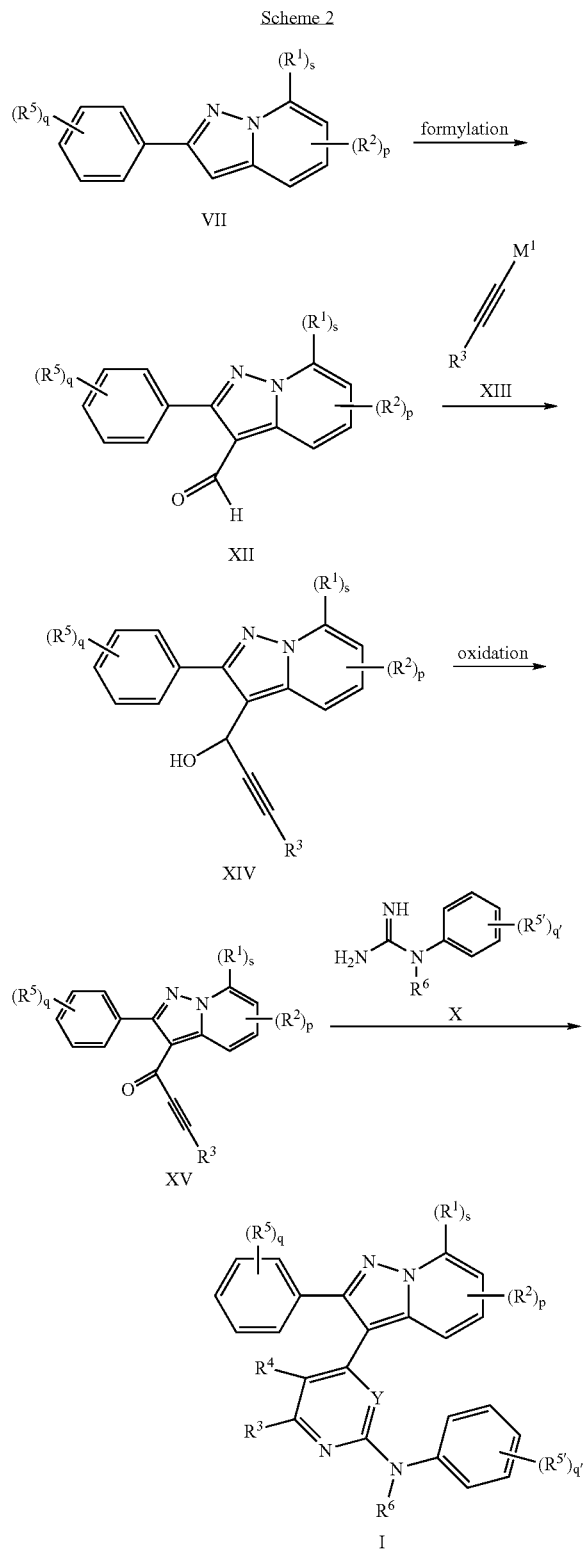

wherein:
s is 0 or 1;

p is 0, 1, 2 or 3;
$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —$NHR^{10}$Het, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —$C(O)NR^7R^8$, —$C(O)NR^7$Ay, —C(O)NHR$^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

each $R^7$ and $R^8$ are the same or different and are each independently selected from the group consisting of H, alkyl, cycloalkyl, alkenyl, cycloalkenyl, —$R^{10}$cycloalkyl, —$OR^9$, —$R^{10}OR^9$, —$NR^9R^{11}$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$SO_2R^{10}$, —$R^{10}NHCOR^9$, and —$R^{10}SO_2NHCOR^9$;

each $R^9$ and $R^{11}$ are the same or different and are each independently selected from the group consisting of H, alkyl, cycloalkyl, —$R^{10}$cycloalkyl, —$R^{10}OH$, —$R^{10}OR^{10}$, and —$R^{10}NR^{10}R^{10}$;

each $R^{10}$ is the same or different and is independently selected from the group consisting of alkyl, cycloalkyl, alkenyl, cycloalkenyl, and alkynyl;

Ay is aryl;
Het is a 5- or 6-membered heterocyclic or heteroaryl group;
n is 0, 1 or 2;
$R^6$ is selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —$NHR^{10}$Het, —$OR^7$, —OAy, —OHet, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —$C(O)NR^7R^8$, —$C(O)NR^7$Ay, —C(O)NHR$^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms, or heteroaryl group containing 1 or 2 heteroatoms; and $M^1$ is Li, Mg-halide or cerium-halide, wherein halide is halo.

Generally, the process for preparing compounds of formula (I) wherein Y is N; $R^3$ is selected from the group consisting of H, alkyl, cycloalkyl, alkenyl, —$R^{10}OR^7$, —$NR^7R^8$ (where $R^7$ and $R^8$ are not H), —$R^{10}NR^7R^8$, —$C(O)R^7$, —$CO_2R^7$, —$SO_2NHR^9$, Ay, and Het; and $R^4$ is H, (all other variables having been defined above in connection with Scheme 2), and pharmacuetically acceptable salts, solvates and physiologically functional derivatives thereof, comprises the following steps:

(a) formylating the compound of formula (VII) to prepare a compound of formula (XII);
(b) reacting the compound of formula (XII) with a compound of formula (XIII) to prepare a compound of formula (XIV);
(c) oxidizing the compound of formula (XIV) to prepare a compound of formula (XV); and
(d) reacting a compound of formula (XV) with a compound of formula (X) to prepare the compounds of formula (I) or a pharmacuetically acceptable salt, solvate and physiologically functional derivative thereof;

More specifically, compounds of formula (I) wherein Y is N; $R^3$ is selected from the group consisting of H, alkyl, cycloalkyl, alkenyl, —$R^{10}OR^7$, —$NR^7R^8$ (where $R^7$ and $R^8$ are not H), —$R^{10}NR^7R^8$, —$C(O)R^7$, —$CO_2R^7$, —$SO_2NHR^9$, Ay, and Het; and $R^4$ is H, and pharmacuetically acceptable salts, solvates and physiologically functional derivatives thereof, may be prepared by reacting a compound of formula (XV) with a compound of formula (X) to prepare a compound of formula (I) or a pharmaceutically acceptable salt, solvate or physiologically functional derivative thereof.

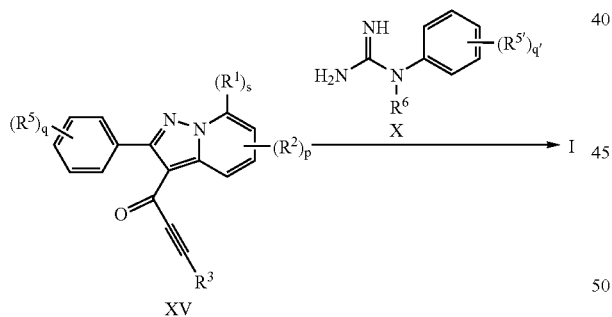

wherein all variables are as defined above in connection with Scheme 2.

This method can be readily carried out by mixing a compound of formula (XV) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, a typical solvent is N,N-dimethylformamide, 1-methyl-2-pyrrolidinone and the like and the base is potassium carbonate, or an amine base such as triethylamine.

Compounds of formula (XV) may be conveniently prepared by oxidation of a compound of formula (XIV).

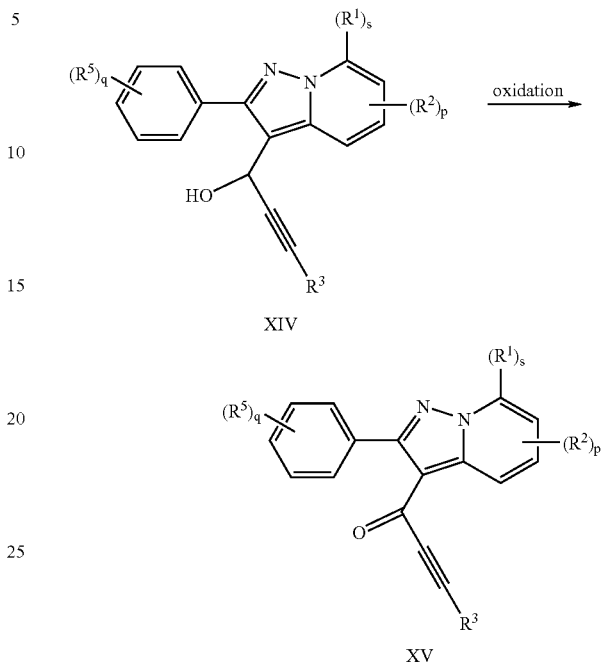

wherein all variables are as defined above in connection with Scheme 2.

Preferred oxidizing agents include but are not limited to, manganese dioxide, and the like, in an inert solvent Suitable inert solvents include but are not limited to, dichloromethane, chloroform, N,N-dimethylformamide, ether, and the like.

Compounds of formula (XIV) may be conveniently prepared by reacting a compound of formula (XII) with a compound of formula (XIII).

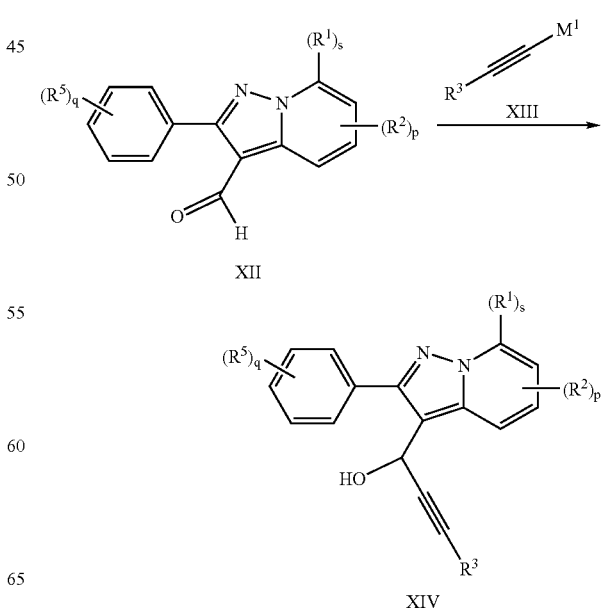

wherein all variables are as defined above in connection with Scheme 2.

Preferred metals (M') in the compounds of formula (XIII) include but are not limited to, lithium, magnesium(II) halides, cerium(III) halides, and the like. Compounds of general formula (XIII) may be purchased from commercial sources or prepared by methods known to one skilled in the art. Typically a compound of formula (XII) is treated with an excess of a compound of formula (XIII) at subzero temperatures in an inert solvent The reaction is typically started at −78° C. and allowed to warm to ambient temperature over several hours. A typical solvent is tetrahydrofuran and the like.

Compounds of formula (XII) may be conveniently prepared from compounds of formula (VII) by a formylation procedure.

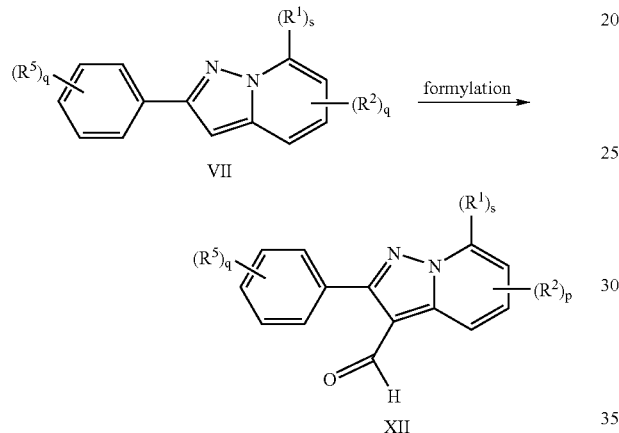

wherein all variables are as defined above in connection with Scheme 2.

Typically the formylation is carried out via the Vilsmeier-Haack reaction. The Vilsmeier-Haack reagents can be purchased from commercial sources or prepared in situ. Preferable conditions include, but are not limited to treating compounds of formula (VI) with a premixed solution of phosphorous oxychloride in N,N-dimethylformamide optionally with heating the reaction to 50–150° C.

The compounds of formula (VII) are prepared according to the process described above in connection with Scheme 1.

Further compounds of formula (I) wherein Y is N, and pharmacuetically acceptable salts, solvates and physiologically functional derivatives thereof, may be conveniently prepared by a general process outlined in Scheme 3 below.

Scheme 3

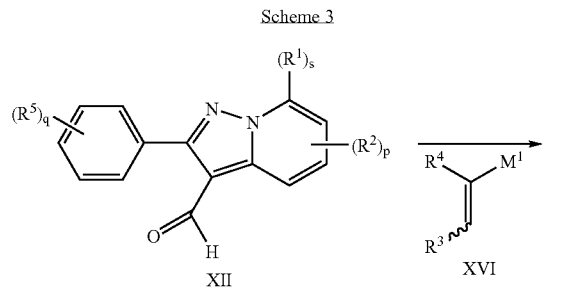

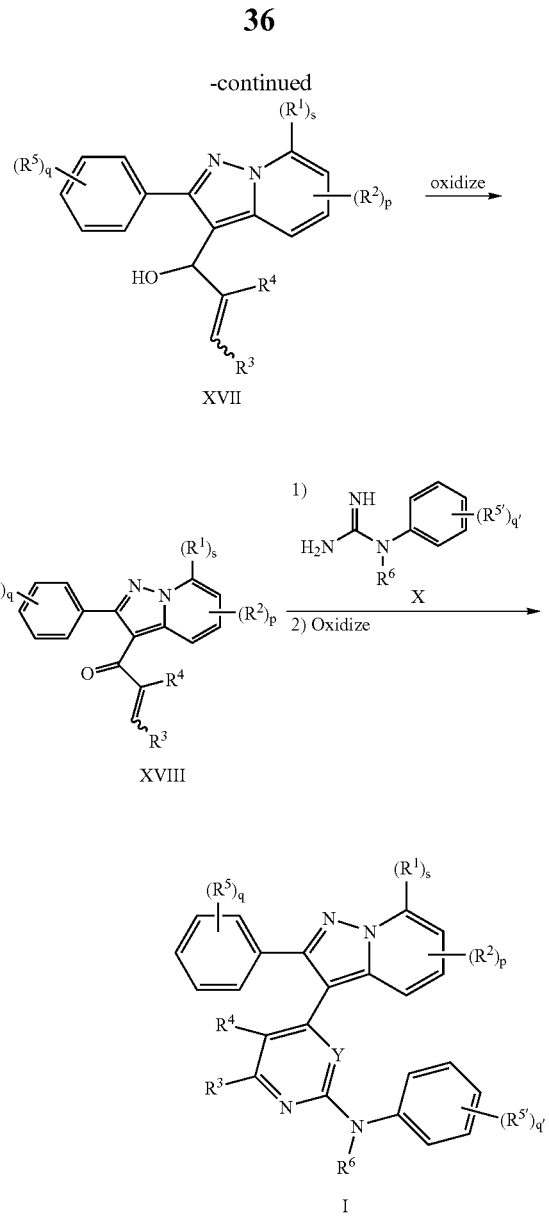

wherein:
s is 0 or 1;
p is 0, 1, 2 or 3;
$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —$NHR^{10}$Het, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —$C(O)NR^7R^8$, —$C(O)NR^7$Ay, —C(O)NHR$^{10}$Het, —$R^{10}C(O)NR^9R^{11}$, —C(S)N R$^9R^{11}$, —$R^{10}$C(S)NR$^9R^{11}$, —$R^{10}$NHC(NH)NR$^9R^{11}$, —C(NH)NR$^7R^8$, —C(NH)NR$^7$Ay, —$R^{10}$C(NH)NR$^9R^{11}$, —$S(O)_2NR^7R^8$, —$S(O)_2NR^7$Ay, —$R^{10}SO_2$NHCOR$^9$, —$R^{10}SO_2$NR$^9R^{11}$, —$R^{10}SO_2R^9$, —$S(O)_nR^9$, cyano, azido and nitro; or
two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

each $R^7$ and $R^8$ are the same or different and are each independently selected from the group consisting of H, alkyl, cycloalkyl, alkenyl, cycloalkenyl, —$R^{10}$cycloalkyl, —$OR^9$, —$R^{10}OR^9$, —$NR^9R^{11}$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

each $R^9$ and $R^{11}$ are the same or different and are each independently selected from the group consisting of H, alkyl, cycloalkyl, —$R^{10}$cycloalkyl, —$R^{10}OH$, —$R^{10}OR^{10}$, and —$R^{10}NR^{10}R^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

$R^3$ and $R^4$ are the same or different and are each independently selected from the group consisting of H, halo, alkyl, cycloalkyl, alkenyl, —$OR^7$, —$R^{10}OR^7$, —$R^{10}OAy$, —$NR^7R^8$, —$R^{10}NR^7R^8$, —$C(O)R^7$, $C(O)Ay$, —$CO_2R^7$, —$CO_2Ay$, —$SO_2NHR^9$, Ay, —$OAy$, —$NR^7Ay$, —$R^{10}NR^7Ay$, Het, —NHHet, and —$NHR^{10}$Het;

$R^6$ is selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}Ay$, —$NR^7Ay$, Het, —NHHet, —$NHR^{10}$Het, —$OR^7$, —$OAy$, —OHet, —$R^{10}OR^9$, —$R^{10}NR^7R^8$, —$R^{10}NR^7Ay$, —$R^{10}C(O)R^9$, —$C(O)R^9$, —C(O)Ay, —C(O) Het, —$CO_2R^9$, —$R^{10}CO_2R^9$, —$C(O)NR^7R^8$, —$C(O)NR^7Ay$, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —C(N H)$NR^7Ay$, —$R^{10}C(NH)NR^9R^{11}$, —$S(O)_2NR^7R^8$, —$S(O)2NR^7Ay$, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms or heteroaryl group containing 1 or 2 heteroatoms; and $M^1$ is Li, Mg-halide or cerium-halide, wherein halide is halo.

Generally, the process for preparing compounds of formula (I) wherein Y is N, and pharmacuetically acceptable salts, solvates and physiologically functional derivatives thereof, (all formulas and all other variables having been defined above in connection with Scheme 3), comprises the following steps:

(a) reacting a compound of formula (XII) with a compound of formula (XVI) to prepare a compound of formula (XVII);

(b) oxidizing the compound of formula (XVII) to prepare a compound of formula (XVIII); and (c) reacting a compound of formula (XVIII) with a compound of formula (X) followed by oxidative aromatization to prepare the compound of formula (I) or a pharmacuetically acceptable salt, solvate or physiologically functional derivative thereof.

More specifically, compounds of formula (I) wherein Y is N, and pharmacuetically acceptable salts, solvates and physiologically functional derivatives thereof, can be prepared by reacting a compound of formula (XVIII) with a compound of formula (X) followed by oxidative aromatization to prepare a compound of formula (I) or a pharmaceutically acceptable salt, solvate or physiologically functional derivative thereof.

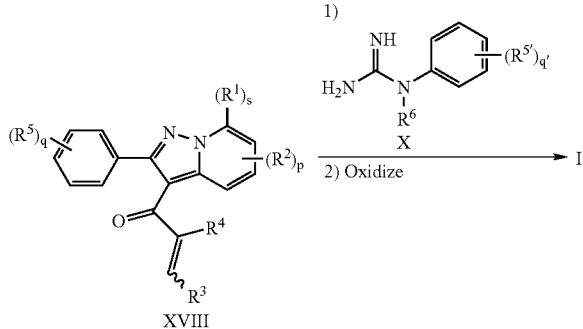

wherein all variables are as defined above in connection with Scheme 3.

The condensation is conveniently carried out by treating the compound of formula (XVIII) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide, 1-methyl-2-pyrrolidinone and the like and the base is potassium carbonate, or an amine base such as triethylamine. The reaction produces a dihydropyrimidine intermediate.

Preferably in the same reaction vessel, the dihydropyrimidine intermediate may be oxidized to a compound of formula (I) by the addition of an oxidizing agent. The reaction may be heated to 50–150° C. or performed at ambient temperature. Preferrably, the oxidizing agent is oxygen ($O_2$), palladium on carbon, 2,3-dichloro-5,6-dicyano-1,4-benzoquinone, or the like.

Compounds of formula (XVIII) may be conveniently prepared by oxidation of compounds of formula (XVII).

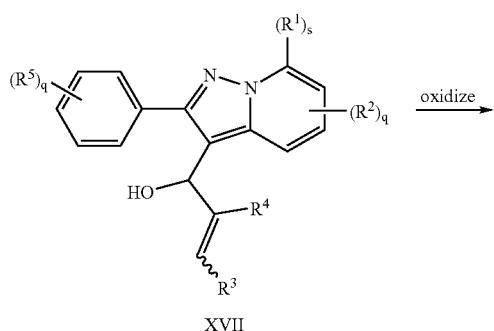

XVII

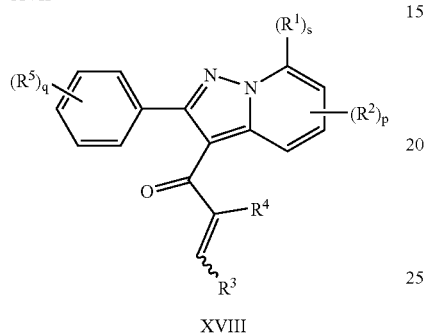

XVIII wherein all variables are as defined above in connection with Scheme 3.

Preferred oxidizing agents for the oxidation of compounds of formula (XVII) include but are not limited to manganese dioxide, and the like. The oxidation is typically carried out in an inert solvent such as for example, dichloromethane, chloroform, N,N-dimethylformamide, ether, and the like.

Compounds of the general formula (XVII) may be conveniently prepared by reacting a compound of general formula (XII) with a compound of formula (XVI).

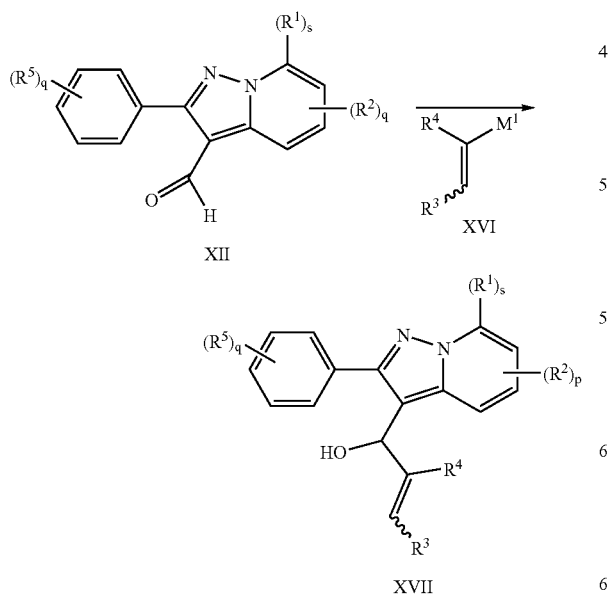

wherein $M^1$ is a metal such as for example, lithium, magnesium(II) halides, Cerium(III) halides, and the like and all other variables are as defined above in connection with Scheme 3.

Compounds of formula (XVI) may be purchased from commercial sources or prepared by methods known to one skilled in the art.

The compounds of formula (XII) may be prepared using the methods described above in connection with Scheme 2.

Compounds of formula (I) wherein Y is CH or N, and pharmacuetically acceptable salts, solvates and physiologically functional derivatives thereof, may be conveniently prepared by a general process outlined in Scheme 4 below.

Scheme 4

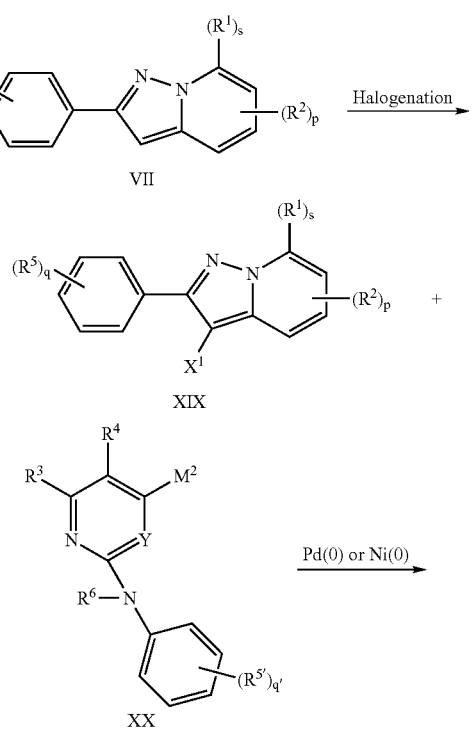

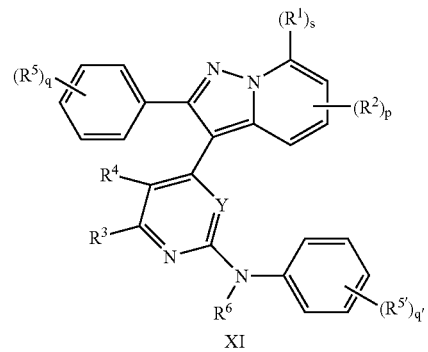

XI wherein:
$X^1$ is halo, preferably bromo or iodo;
s is 0 or 1;
p is 0, 1, 2 or 3;
$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —NHR$^{10}$Het, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^2$ groups together with the atoms to which they are bonded form a 5- or 6-membered cycloalkyl or heterocyclic group containing 1 or 2 heteroatoms; or R$^2$ is in the C-6 position and R$^1$ and R$^2$ together with the atoms to which they are bonded form a 5- or 6-membered cycloalkyl or heterocyclic group containing 1 or 2 heteroatoms;

each R$^7$ and R$^8$ are the same or different and are each independently selected from the group consisting of H, alkyl, cycloalkyl, alkenyl, cycloalkenyl, —R$^{10}$cycloalkyl, —OR$^9$, —R$^{10}$OR$^9$, —NR$^9$R$^{11}$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NH$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

each R$^9$ and R$^{11}$ are the same or different and are each independently selected from the group consisting of H, alkyl, cycloalkyl, —R$^{10}$cycloalkyl, —R$^{10}$OH, —R$^{10}$OR$^{10}$, and —R$^{10}$NR$^{10}$R$^{10}$;

each R$^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

R$^3$ and R$^4$ are the same or different and are each independently selected from the group consisting of H, halo, alkyl, cycloalkyl, alkenyl, —OR$^7$, —R$^{10}$OR$^7$, —R$^{10}$OAy, —NR$^7$R$^8$, —R$^{10}$NR$^7$R$^8$, —C(O)R$^7$, C(O)Ay, —CO$_2$R$^7$, —CO$_2$Ay, —SO$_2$NHR$^9$, Ay, —OAy, —NR$^7$Ay, —R$^{10}$NR$^7$Ay, Het, —NHHet, and —NHR$^{10}$Het;

R$^6$ is selected from the group consisting of H, alkyl, cycloalkyl, alkenyl, cycloalkenyl, —R$^{10}$cycloalkyl, —R$^{10}$OR$^9$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

q and q' are the same or different and are each independently selected from the group consisting of 0, 1, 2, 3, 4 and 5;

each R$^5$ and R$^{5'}$ are the same or different and are each independently selected from the group consisting of halo, alkyl, alkenyl, alkynyl, cycloalkyl, cycloalkenyl, —R$^{10}$cycloalkyl, —NR$^7$R$^8$, Ay, —NHR$^{10}$Ay, —NR$^7$Ay, Het, —NHHet, —NHR$^{10}$Het, —OR$^7$, —OAy, —OHet, —R$^{10}$OR$^9$, —R$^{10}$NR$^7$R$^8$, —R$^{10}$NR$^7$Ay, —R$^{10}$C(O)R$^9$, —C(O)Ay —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ or R$^{5'}$ groups together with the atoms to which they are bonded form a 5- or 6-membered cycloalkyl, aryl, heterocyclic group containing 1 or 2 heteroatoms or heteroaryl group containing 1 or 2 heteroatoms; and M$^2$ is —B(OH)$_2$, —B(ORa)$_2$, —B(Ra)$_2$, —Sn(Ra)$_3$, Zn-halide, ZnRa, Mg-halide where Ra is alkyl or cycloalkyl and halide is halo.

Generally, the process for preparing compounds of formula (I), and pharmacuetically acceptable salts, solvates and physiologically functional derivatives thereof (all formulas and variables having been defined above in connection with Scheme 4), comprises the following steps:

(a) halogenating a compound of formula (VII) to prepare a compound of formula (XIX); and (b) reacting a compound of formula (XIX) with a compound of formula (XX) to prepare a compound of formula (I) or a pharmaceutically acceptable salt, solvate or physiologically functional derivative thereof.

More specifically, compounds of formula (I), and pharmacuetically acceptable salts, solvates and physiologically functional derivatives thereof can be prepared by reacting a compound of formula (XIX) with a compound of formula (XX).

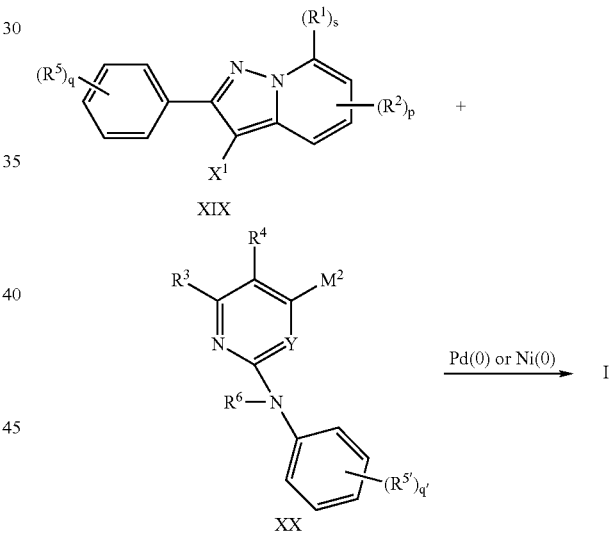

wherein all variables are as defined above in connection with Scheme 4.

The reaction may be carried out in an inert solvent, in the presence of a palladium (O) or nickel (O) catalyst. The reaction may optionally be heated to about 50–150° C. Preferably the reaction is performed by reacting equimolar amounts of a compound of formula (XIX) with a Het-metal compound of formula (XX), but the reaction may also be performed in the presence of an excess of compound of the formula (XX). The palladium or nickel catalyst is preferably present in 1–10 mol % compared to the compound of formula (XIX). Examples of suitable palladium catalysts include but are not limited to, tetrakis(triphenylphosphine) palladium (O), dichlorobis(triphenyl-phosphine)palladium (II), tris(dibenzylideneacetone)dipalladium (O), and bis (diphenylphosphinoferrocene)palladium (II) dichloride.

Suitable solvents include but are not limited to, N,N-dimethylformamide, toluene, tetrahydrofuran, dioxane, and 1-methyl-2-pyrrolidinone. When the Het-metal compound of formula (XX) is a boronic acid or ester or a borinate the reaction is more conveniently carried out by adding a base in a proportion equivalent to, or greater than, that of the compound of formula (XX). Het-metal compounds of formula (XX) may be obtained from commercial sources or prepared either as discreet isolated compounds or generated in situ using methods known to one skilled in the art (Suzuki, A. J. Organomet Chem. 1999, 576,147; Stille, J. Angew. Chem. Int Ed. Engl. 1986, 25, 508; Snieckus, V. J. Org. Chem. 1995, 60, 292.)

Compounds of formula (XIX) can be prepared from compounds of formula (VII) by a halogenation procedure.

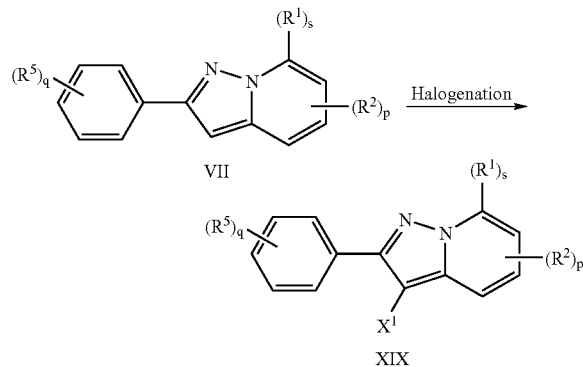

wherein all variables are as defined above in connection with Scheme 4.

Typically, the halogenation reaction is carried out by subjecting the compounds of formula (VII) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (VII) can be prepared using methods described above in connection with Scheme 1.

As will be apparent to those skilled in the art, the compounds of formula (I) may be converted to other compounds of formula (I) using techniques well known in the art As an example, compounds of formula (I-A) may be converted to compounds of formula (I-B) using either of two methods.

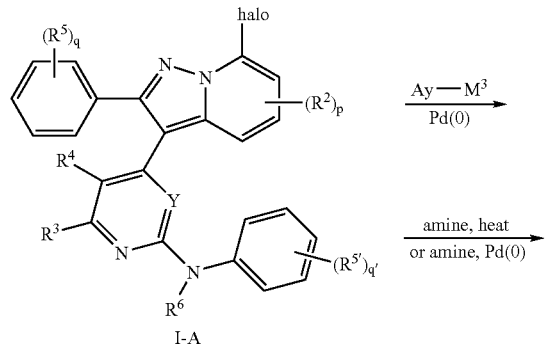

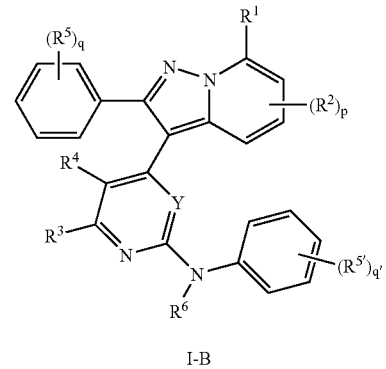

wherein $M^3$ is $B(OH)_2$, $B(ORa)_2$, $B(Ra)_2$, $Sn(Ra)3$, Zn-halide, Zn—Ra or Mg-halide, Ra is alkyl or cycloalkyl and halide is halo; and all other variables are as defined above in connection with any of the processes described above.

Such a method can be carried out using the reaction and conditions described above in connection with Scheme 1 and the conversion of compounds of formula (VIII-A) to compounds of formula (VIII-B). Thus, the present invention provides a process for converting compounds of formula (I-A) to compounds of formula (I-B) which comprises either: (1) replacing the C-7 halogen of the compound of formula (I-A) with an amine; or (2) coupling the compound of formula (I-A) with an aryl metal of the formula Ay-$M^3$ where $M^3$ is $B(OH)_2$, $B(ORa)_2$, $B(Ra)_2$, $Sn(Ra)_3$, Zn-halide, Zn—Ra or Mg-halide.

As a further example, compounds of formula (I-C) may be converted to compounds of formula (I-D) by reduction of a nitro group using conventional techniques known to those skilled in the art

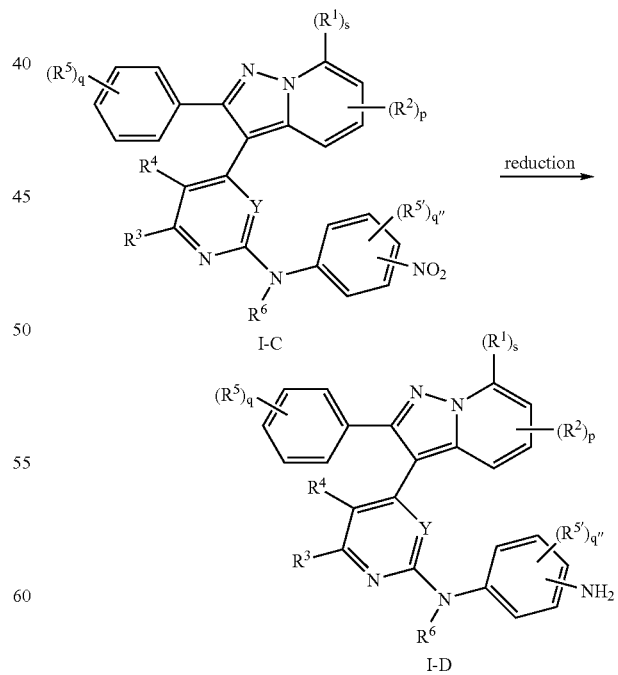

wherein q" is 0, 1, 2, 3 or 4; and all other variables are as defined above in connection with any of the processes described above.

The reduction can conveniently be carried out by using zinc, tin or iron and acid, by using tin(II)chloride, or by using palladium or platinum catalysts under hydrogen atmosphere in a suitable solvent as obvious to one skilled in the art of organic synthesis.

Compounds of formula (I-D) may be further converted to compounds of formula (I-E) by diazotization followed by a Sandmeyer reaction.

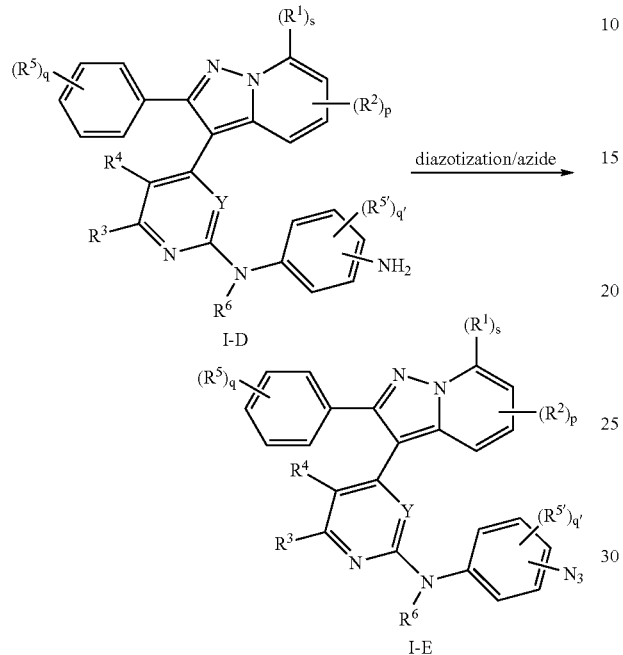

wherein q" is 0, 1, 2, 3 or 4; and all other variables are as defined above in connection with any of the processes described above.

The diazotization/Sandmeyer sequence can be typically carried out by treating a compound of formula (I-D) with a nitrite source followed by treatment with a nucleophile. Sources of nitrite include but are not limited to sodium nitrite and tert-butyl nitrite. A representative nucleophile is sodium azide. A typical solvent is aqueous acetic acid. Other Sandmeyer variations will be obvious to those skilled in the art.

As a further example of converting compounds of formula (I) into other compounds of formula (I), compounds of formula (I-F) (i.e., compounds of formula (I) wherein q is 1 or more and at least one $R^1$ is O-methyl) may be converted to compounds of formula (I-G) (i.e., compounds of formula (I) wherein q is 1 or more and at least one $R^5$ is —OH) using conventional demethylation techniques. Additionally, compounds of formula (I-G) may optionally be converted to compounds of formula (I-H) (i.e., compounds of formula (I) wherein q is 1 or more and at least one $R^5$ is —$OR^{10}$). For example, the foregoing conversions are represented schematically as follows:

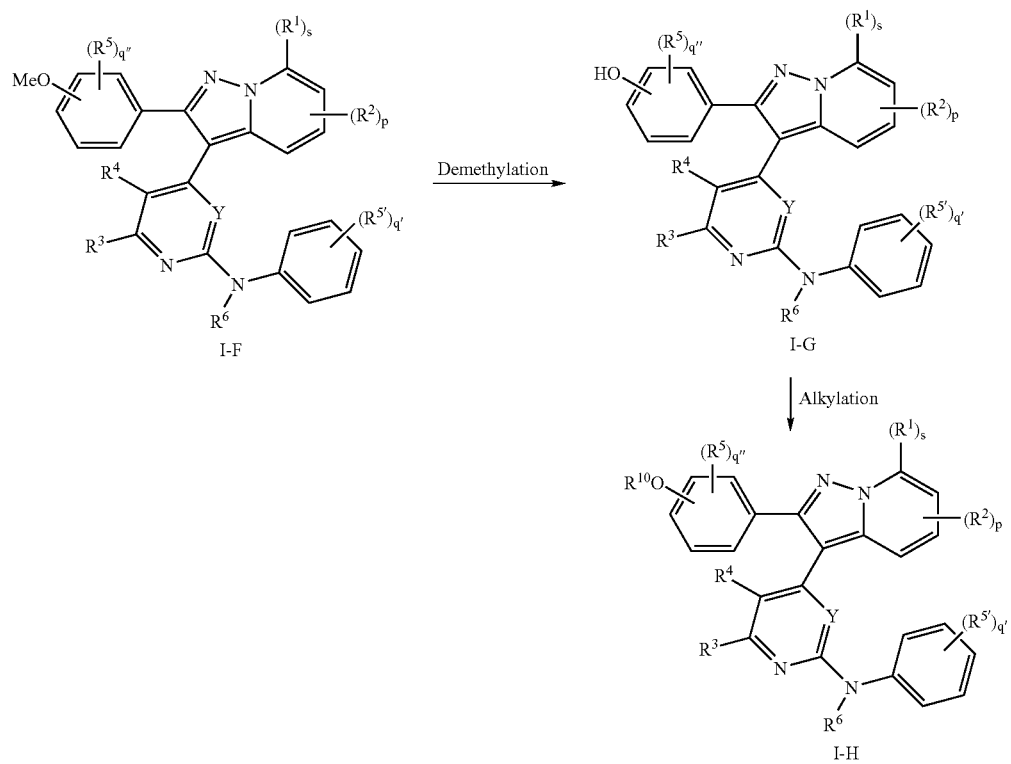

wherein q″ is 0, 1, 2, 3 or 4; and all other variables are as defined above in connection with any of the processes described above.

The demethylation reaction may be carried out by treating a compound of formula (I-F) in a suitable solvent with a Lewis acid at a temperature of −78° C. to room temperature, to produce a compound of formula (I-G). Typically the solvent is an inert solvent such as dichloromethane, chloroform, acetonitrile, toluene and the like. The Lewis acid may be boron tribromide, trimethylsilyl iodide and the like.

Optionally, the compounds of formula (I-G) may be further converted to compounds of formula (I-H) by an alkylation reaction. The alkylation reaction may be carried out by treating a compound of formula (I-G) in suitable solvent with an alkyl halide of formula $R^{10}$-Halo where $R^{10}$ is as defined above, to form another compound of formula (I-H). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

In yet another example, compounds of formula (I-I) (i.e., compounds of formula (I) wherein q is 1 or more and at least one $R^1$ is halo) or compound of formula (I-J) (i.e. compounds of formula (I) wherein q is 1 or more and at least one $R^5$ is nitro) can be converted to compounds of formula (I-K) (i.e., compounds of formula (I) wherein q is 1 or more and at least one $R^5$ is $NH_2$). Optionally, compounds of formula (I-K) may then be converted to compounds of formula (I-L) (i.e., compounds of formula (I) wherein q is 1 or more and at least one $R^5$ is —$NR^7R^8$ where $R^7$ and $R^8$ are not both H). For example, the foregoing conversions are represented schematically as follows:

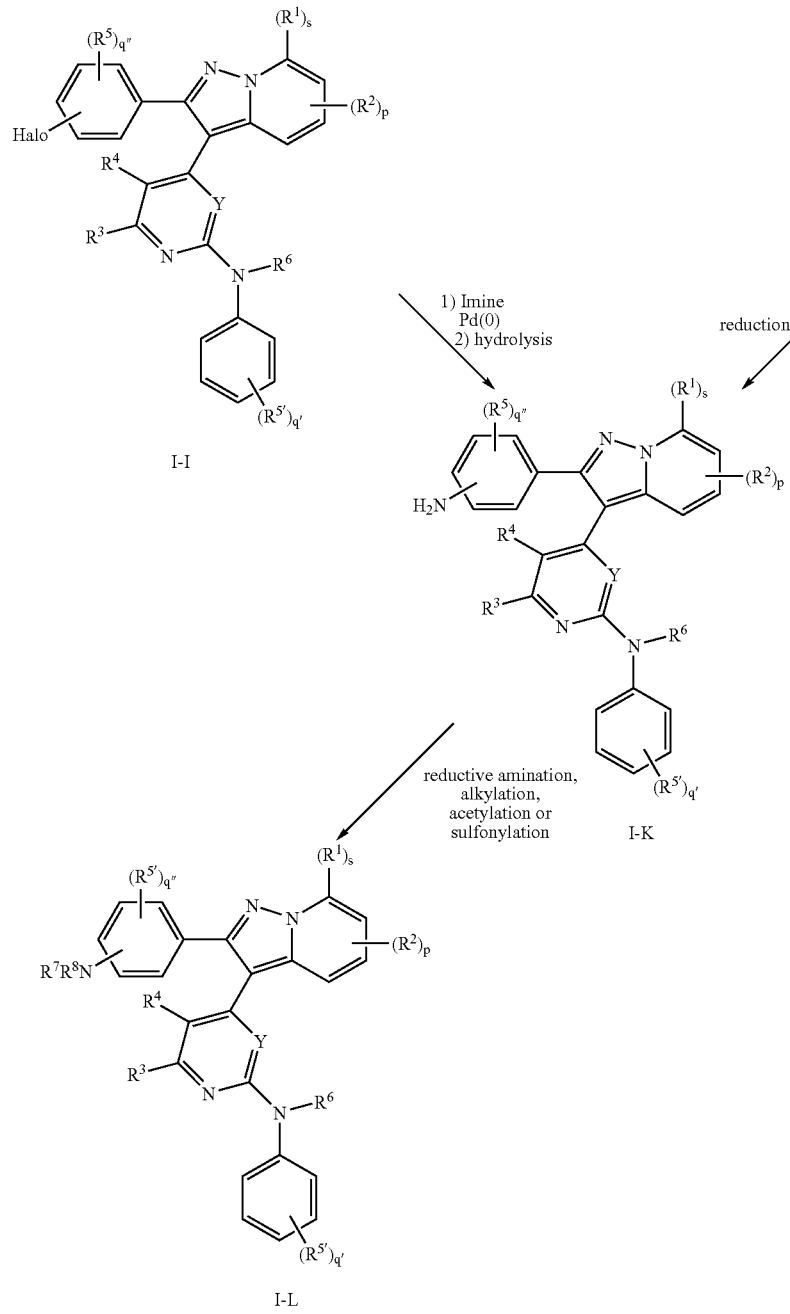
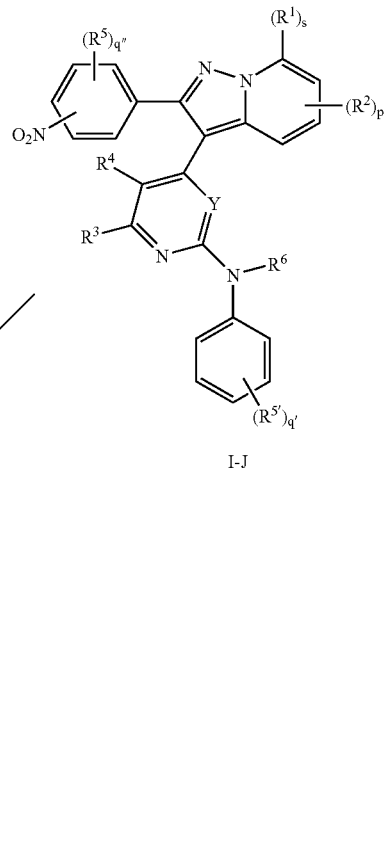

wherein q″ is 0, 1, 2, 3 or 4; and all other variables are as defined above in connection with any of the processes described above.

The process of converting compounds of formula (I-I) to compounds of formula (I-K) is carried out by reacting a compound of general formula (I-I) with an imine in the presence of a palladium (O) source, a base and a suitable ligand, followed by hydrolysis to give a compound of formula (I-K). See J. Wolfe, et al., *Tetrahedron Letters* 38:6367–6370 (1997). Typically the imine is benzophenoneimine, the palladium (O) source is tris(dibenzylideneacetone)dipalladium(O), the base is sodium tert-butoxide and the ligand is racemic-2,2′-bis(diphenylphosphino)-1,1′-binaphthyl. Suitable solvents include N,N-dimethylformamide and the like.

Compounds of formula (I-K) can also be obtained from compounds of formula (I-J) by reduction. The reduction can conveniently be carried out by using zinc, tin or iron and acid, by using tin(II)chloride, or by using palladium or platinum catalysts under hydrogen atmosphere in a suitable solvent as obvious to one skilled in the art of organic synthesis.

Reaction of a compound of formula (I-K) with compound of formula $R^7$-halogen in a suitable solvent in the presence of base, optionally with heating may be used to prepare compounds of formula (I-L). Typically the base is triethylamine or pyridine and the solvent is N,N-dimethylformamide and the like.

Additional compounds of formula (I-L) can be obtained by reductive amination of compounds of formula (I-K) with ketones or aldehydes. See, A. Abdel-Magid, et al., *J. Org. Chem.* 61:3849–3862 (1996). Typically a compound of formula (I-K) is treated with an aldehyde or a ketone in the presence of an acid, such as acetic acid, and a reducing agent, such as sodium triacetoxyborohydride and the like, in an inert solvent such as dichloroethane and the like.

Other transformations well known to those skilled in the art for use with anilines may be used to convert compounds of formula (I-K) to compounds of formula (I-L). In addition it will be obvious to those skilled in the art that the above mentioned conversions regarding $R^5$ substituents would be expected to be equally applicable to any substituted aromatic position in general formula (I) for use in the synthesis of additional compounds of formula (I).

In a further embodiment of the present invention, certain compounds of formula (I-M) may be converted to other compounds of formula (I) (i.e., compounds of formula (I-N) by a deprotonation/electrophile quench protocol. It will be apparent to one skilled in the art that compounds of the formula (I-M) wherein s is 0 can be prepared according to the methods described in Schemes 1 through 4. The compounds of formula (I-M can be converted to compounds of formula (I-N) by reaction of a compound of formula (I-M) with a base, such as n-butyllithium, followed by reacting with an electrophilic agent.

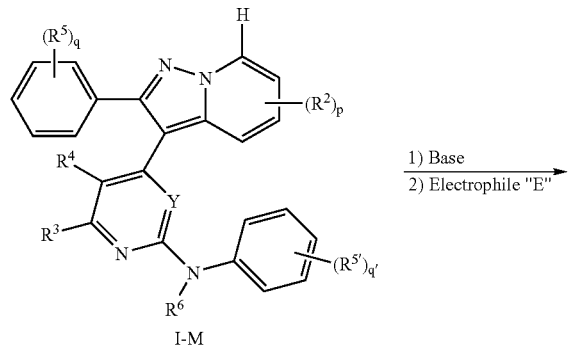

I-M

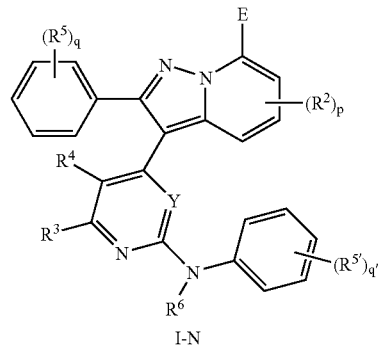

I-N wherein E is $R^1$ and all other variables are as defined above in connection with any of the processes described above.

Electrophiles which may be used in this process include, but are not limited to: alkyl halides (E=methyl, benzyl etc.); N-bromosuccinimide (E=bromine); N-chlorosuccinimide (E=chlorine); carbon tetrachloride (E=chlorine); N-iodosuccinimide (E=iodine); iodine (E=iodine); aldehydes (E=CH(OH)$R^{10}$); dimethylformamide (E=CHO); dimethyl disulfide (E=SMe); diethyl disulfide (E=SEt); carbon dioxide (E=CO$_2$H); dimethylcarbamoyl chloride (E=C(O)NMe$_2$) and the like.

Each of the foregoing processes may further comprise the step of converting the compounds of formula (I) to a salt, solvate, or physiologically functional derivative thereof, using techniques well known to those skilled in the art.

Based upon this disclosure and the examples contained herein one skilled in the art can readily convert compounds of formula (I) or a pharmaceutically acceptable salt, solvate or physiologically functional derivative thereof into other compounds of formula (I), or salts, solvates or physiologically functional derivatives thereof.

The present invention also provides radiolabeled compounds of formula (I). Radiolabeled compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated. The radiolabeled compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) to the target protein. More specifically, suitable assay methods will include competition binding assays. The radiolabeled compounds of formula (I) can be employed in assays according to the methods conventional in the art.

The following examples are illustrative embodiments of the invention, not limiting the scope of the invention in any way. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

3-(2-Anilino-4-pyrimidinyl)-N-cyclopentyl-2-(4-fluorophenyl)-pyrazolo[1,5-α]pyridin-7-amine

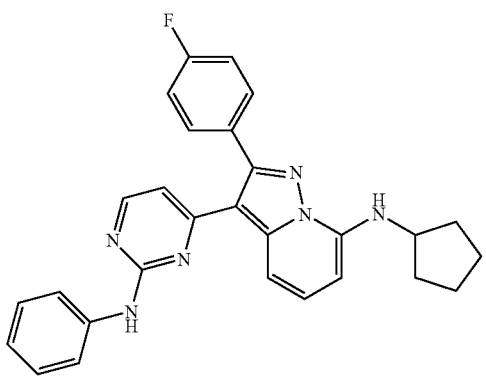

a) 2-(6—Chloro-2-pyridinyl)-1-(4-fluorophenyl)ethanone.

To a cold (0° C.) solution of 6-chloro-2-picoline (21.4 mL, 196.0 mmol) and ethyl 4-fluorobenzoate (57.5 mL, 391.2 mmol) in tetrahydrofuran (311 mL) was added lithium bis(trimethylsilyl)amide (391 mL, 1.0 M in tetrahydrofuran, 391.0 mmol) dropwise via a pressure equalizing funnel over 1 hour. Upon complete addition, the cold bath was removed and the resultant solution was heated to 45° C. for 15 hours. The mixture was cooled to room temperature and quenched by the addition of water. Ether was added and the organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone (32.2 g, 66%) as a tinted off-white solid existing as a keto-enol tautomeric mixture. $^1$H NMR (CDCl$_3$): for the keto tautomer δ 8.11 (m, 2 H), 7.66 (t, 1 H), 7.30–7.25 (m 2 H), 7.17 (t, 2 H), 4.48 (s 2 H), $^{19}$F NMR (CDCl$_3$) δ −104.72 (keto), −111.64 (enol); MS m/z 250 (M+1).

b) 2-(6-Chloro-2-pyridinyl)-1-(4-fluorophenyl)ethanone oxime.

To a solution of 2-(6-chloro-2-(4-fluorophenyl)ethanone (74.9 g, 299.8 mmol) in methanol (900 mL) was added hydroxylamine hydrochloride (104 g, 1.49 mol) followed by sodium hydroxide (600 mL, 10% aqueous, 1.5. mol). The resultant suspension was heated to reflux for 2 hours and then cooled to room temperature. The mixture was concentrated in vacuo and the residue taken up in ether and water. The organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone oxime (67.9 g, 86%) as a white solid. $^1$H NMR (CDCl$_3$): δ 8.69 (s, 1 H), 7.71 (dd, 2 H), 7.53 (t, 1 H), 7.18–7.16 (m, 2 H), 7.03 (t, 2 H), 4.37 (s, 2 H); $^{19}$F NMR (CDCl$_3$) δ −111.77; MS m/z 265 (M+1).

c) 7-Chloro-2-(4fluorophenyl)pyrazolo[1,5-α]pyridine.

To a solution of 2-(6-chloro-2-pyridinyl)-1-(4-fluorophenyl)ethanone oxime (109.2 g, 414 mmol) in 1,2-dimethoxyethane (500 mL) at 0° C. was added trifluoroacetic anhydride (59 mL, 414 mmol), keeping the temperature below 10° C. After the addition was complete, the reaction was warmed to 15° C. The solution was then cooled to 4° C. and a solution of triethylamine (116 mL, 828 mmol) in 1,2-dimethoxyethane (60 mL) was added over 0.5 hours. After warming to room temperature, the mixture was stirred for 1.5 hours. To this was added iron(II) chloride (0.52 g, 4.1 mmol) and the reaction was heated to reflux for 3 hours. The reaction was concentrated and the resulting solid was recrystallized from ethyl acetate-hexanes to give 7-chloro-2-(4-fluorophenyl)pyrazolo[1.5-α]pyridine (69.7 g. 68%) as off-white needles. $^1$H NMR (CDCl$_3$): δ 8.03 (m, 2 H), 7.54 (d, 1 H), 7.16 (m, 3 H), 6.93 (d, 1 H), 6.91 (s, 1 H); MS m/z 247 (M+1); mp 156–157° C.

d) 1-[7-Chloro-2-(4-fluorophenyl)pyrazolo[1,5-α]pyridin-3-yl]ethanone.

To a solution of 7-chloro-2-(4-fluorophenyl)pyrazolo[1, 5-α]pyridine (10.0 g, 40.5 mmol) in toluene (225 mL) at room temperature was added acetic anhydride (4.6 mL, 48.6 mmol). Boron trifluoride diethyletherate (5.6 mL, 44.6 mmol) was then added dropwise and the resultant solution was heated to reflux for 3.5 hours. The reaction mixture was cooled to room temperature and quenched by the dropwise addition of aqueous sodium bicarbonate. Ether was added and the organic layer was washed with brine. The aqueous layer was extracted with ether and the-combined organics were dried over magnesium sulfate, filtered and concentrated. The residue was purified by recrystallization from ethyl acetate-hexanes to give 1-[7-chloro-2-(4-fluorophenyl)pyrazolo[1,5-α]pyridin-3-yl]ethanone (9.0 g, 77%) as redish needles.$^1$H NMR (CDCl$_3$): δ 8.41 (d, 1 H), 7.59 (m, 2 H). 7.45 (dd,$_1$ H), 7.26–7.13 (m 3 H), 2.15 (s, 3 H); $^{19}$F NMR (CDCl$_3$) δ −112.06; MS m/z 289 (M+1).

e) 1-[7-(Cyclopentylamino)-2-(4-fluorophenyl)pyrazolo[1, 5-α]pyridin-3-yl]ethanone.

To a solution of 1-[7-chloro-2-(4-fluorophenyl)pyrazolo[1 5-α]pyridin-3-yl]ethanone (2.7 g, 9.5 mmol) in toluene (50 mL) was added successively racemic-BINAP (378 mg, 0.6 mmol), cesium carbonate (4.7 g, 14.3 mmol), cyclopentylamine (4.7 mL, 47.5 mmol), and palladium (II) acetate (86 mg, 0.4 mmol). The resultant mixture was heated to 95° C. for 2.5 hours at which time the reaction was judged complete by thin layer chromatography. The solution was cooled to room temperature and ether was added. The organic layer was washed with water and brine. The aqueous layer was extracted with ether and the combined organics dried over magnesium sulfate. Filtration and concentration followed by flash chromatography (4:1 hexanes-ethyl acetate) provided 1-[7-(cyclopentylamino)-2-(4-fluorophenyl)pyrazolo[1,5-α]pyridin-3-yl]ethanone (3.1 g, 95%) as a yellow solid. $^1$H NMR-(CDCl$_3$): δ 7.62 (d, 1 H), 7.55 (dd, 2 H), 7.40 (t, 1 H), 7.15 (t, 2 H), 6.10 (d, 1 H), 5.99 (d, 1 H), 3.94 (m, 1 H), 2.09 (s, 3 H), 2.12–2.04 (m, 2 H), 1.78–1.58 (m, 6 H); $^{13}$C NMR (CDCl$_3$) δ 192.63, 163.28 (d, J$_{CF}$=247.3 Hz), 154.89, 142.65, 142.38, 131.66 (d, J$_{CF}$=8.3 Hz) 131.09,130.03 (d, J$_{CF}$=3.8 Hz), 115.33 (d, J$_{CF}$=22.0 Hz), 111.32, 105.41, 91.97, 53.81,33.21, 30.10, 23.96; $^{19}$F NMR (CDCl$_3$) δ −112.70; MS m/z338 (M+1).

f) (2E)-1-[7-(Cyclopentylamino)-2-(4-fluorophenyl)pyrazolo[1,5-α]pyridin-3-yl]-3-(dimethylamino)-2-propen-1-one.

A solution of 1-[7-(cyclopentylamino)-2-(4-fluorophenyl) pyrazolo[1,5-α]pyridin-3-yl]ethanone (3.1 g, 9.2 mmol) in N,N-dimethylformamide dimethyl acetal (25 mL) was heated to reflux for 6 days. The mixture was cooled to room temperature, ethylacetate was added followed by water. The organic layer was washed with brine. The aqueous layer was extracted with ethyl acetate and the combined organics were dried over magnesium sulfate. Filtration and concentration followed by flash chromatography (ethyl acetate) provided (2E)-1-[7-(cyclopentylamino)-2-(4-fluorophenyl)pyrazolo [1,5-α]pyridin-3-yl]-3-(dimethylamino)-2-propen-1-one (3.6 g, 99%) as a tinted oil. $^1$H NMR (CDCl$_3$): δ 7.73–7.61 (m, 4 H), 7.32 (t, 1 H), 7.14 (t, 2 H), 6.03 (d, 1 H), 5.96 (d, 1 H), 5.05 (d, 1 H), 3.99 (m, 1 H), 5.15–2.42 (broad, 6 H), 2.19–2.08 (m, 2 H), 1.86–1.62 (m, 6 H); $^{19}$F NMR (CDCl$_3$) δ −113.75; MS m/ 393 (M+1).

g) N-Phenylguanidinium Nitrate.

To a room temperature solution of aniline (10.0 g, 107 mmol) in ethanol (100 mL) was added cyanamide (9.6 mL, 50 wt% in water, 123 mmol) followed by the dropwise addition of concentrated nitric acid (7.56 mL). The mixture was heated at reflux for 3.5 hours and allowed to cool to room temperature. The mixture was concentrated in vacuo and the residue was crystallized from methanol/ethyl acetate/dichloromethane to yield N-phenylguanidinium nitrate (6.7 g, 32%) as a white crystalline solid. $^1$H NMR (DMSO-d$_6$): δ 9.63 (s, 1 H), 7.44 (t, 2 H), 7.37 (broad s, 3 H), 7.29 (t, 1 H), 7.23 (d, 2 H); $^{13}$C NMR (DMSO-d$_6$): δ 156.36, 135.99, 130.40, 127.19, 125.18; MS m/z 136 (M+1 of free base).

h) 3-(2-Anilino-4pyrimidinyl)-N-cyclopentyl-2-(4-fluorophenyl)pyrazolo[1,5-α]pyridin-7-amine.

To a solution of (2E)-1-[7-(cyclopentylamino)-2-(4-fluorophenyl)pyrazolo[1,5-α]pyridin-3-yl]-3-(dimethylamino)-2-propen-1-one (100 mg, 0.25 mmol) in N,N-dimethylformamide (5 mL) was added N-phenylguanidinium nitrate (252 mg, 1.27 mmol) and potassium carbonate (175 mg, 1.27 mmol). The suspension was heated at 140 ° C. (bath temperature) for 21 hours. The mixture was cooled to room temperature, ether was added followed by water. The organic layer was washed with brine. The aqueous layer was extracted with ether and the combined organics were dried over magnesium sulfate. Filtration and concentration followed by flash chromatography (2:1 hexanes-ethyl acetate) provided 3-(2-anilino-4-pyrimidinyl)-N-cyclopentyl-2-(4-fluorophenyl)pyrazolo[1,5-α]pyridin-7-amine which was recrystallized from ether/hexanes (90 mg, 76%) to give a white crystalline solid. $^1$H NMR (CDCl$_3$): δ 8.15 (d, 1 H), 7.69–7.59 (m, 5 H), 7.32–7.27 (m, 3 H), 7.18–7.13 (m, 3H), 7.02 (t, 1 H), 6.49 (d, 1 H), 6.06–6.01 (m, 2 H), 4.01 (m, 1 H), 2.20–2.10 (m, 2 H), 1.86–1.64 (m, 6 H); $^{13}$C NMR (CDCl$_3$): δ 163.20 (d, J$_{CF}$=246.6 Hz), 161.55, 160.11, 156.76, 152.27, 142.72, 141.15, 139.74, 131.47 (d, J$_{CF}$=8.3 Hz), 129.72 (d, J$_{CF}$=3.4 Hz), 128.82, 128.66, 122.28, 119.52, 115.60 (d, J$_{CF}$=21.3 Hz), 110.83, 106.91, 105.15, 90.34, 53.86, 33.32, 24.05; MS m/z 465 (M+1).

EXAMPLE 2

N-Cyclopentyl-2-(4-fluorophenyl)-3-[2-(3,4,5-trimethoxyanilino)-4-pyrimidinyl]pyrazolo[1,5-α]pyridin-7-amine

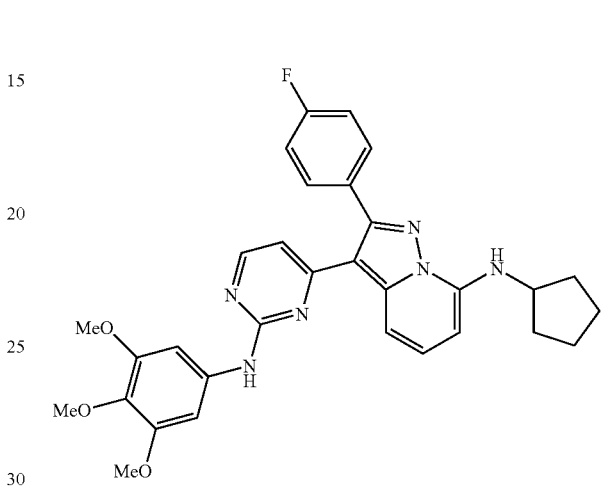

a) N-(3,4,5-Trimethoxyphenyl)guanidinium nitrate.

To a room temperature solution of 3,4,5-trimethoxyaniline (3.46 g,18.9 mmol) in ethanol (20 mL) was added cyanamide (1.68 mL, 50 wt % in water, 21.7 mmol) followed by the dropwise addition of concentrated nitric acid (1.33 mL). The mixture was heated at reflux for 13 hours and allowed to cool to room temperature. The mixture was concentrated in vacuo to approximately 70% of its original volume and ether was added. The resulting precipitate was isolated on a filter to yield N-(3,4,5-trimethoxyphenyl) guanidinium nitrate (2.5 g, 46%) as a grey powder. $^1$H NMR (DMSO-d$_6$): δ 9.47 (s, 1 H), 7.29 (s, 3 H), 6.57 (s, 2 H), 3.80 (s, 6 H), 3.68 (s, 3 H); $^C$ NMR (DMSO-d$_6$): δ 155.78, 153.33, 136.07, 130.58, 102.90, 59.99, 55.96; MS m/z226 (M+1 of free base).

b) N-Cyclopentyl-2-(4-fluorophenyl)-3-[2-[3,4,5-trimethoxyanilino]-4-pyrimidinyl]pyrazolo[1,5-α]pyridin-7-amine.

In a similar manner as described in Example 1 from (2E)-1-[7-(cyclopentylamino)-2-(4-fluorophenyl)pyrazolo [1,5-α]pyridin-3-yl]-3-(dimethylamino)-2-propen-1-one (50 mg, 0.13 mmol) and N-(3,4,5-trimethoxyphenyl)guanidinium nitrate (183 mg, 0.64 mmol) was formed N-cyclopentyl-2-(4-fluorophenyl)-3-[2-(3,4,5-trimethoxyanilino)-4-pyrimidinyl]pyrazolo[1,5-α]pyridin-7-amine (30 mg, 43%) as a yellow solid. $^1$H NMR (CDCl$_3$): δ 8.10 (d, 1 H), 7.73 (d, 1 H), 7.65 (dd, 2 H), 7.36 (s, 1 H), 7.26 (m, 1 H), 7.14 (t, 2 H), 6.98 (s, 2 H), 6.42 (d, 1 H). 6.05–6.01 (m, 2 H),. 4.00 (m, 1 H), 3.84 (s, 3 H), 3.80 (s, H), 2.13 (m, 2 H), 1.82 (m, 2 H), 1.68 (m, 4 H); $^{13}$C NMR (CDCl$_3$): δ 163.24 (d, J$_{CF}$=246.5 Hz), 161.65, 160.17, 156.62, 153.33, 152.24, 142.68, 141.12, 135.99, 133.41, 131.44 (d, J$_{CF}$=8.4 Hz), 129.68, 128.73, 115.66 (d, J$_{CF}$=21.2 Hz), 110.79, 106.91, 105.51, 97.52, 90.47, 61.02, 56.11, 53.88, 33.35, 24.05; MS mk 555 (M+1).

EXAMPLE 3

N-Cyclopentyl-2-(4fluorophenyl)-3-[2-(4methoxyanilino)-4-pyrimidinyl]pyrazolo[1,5-α]pyridin-7-amine

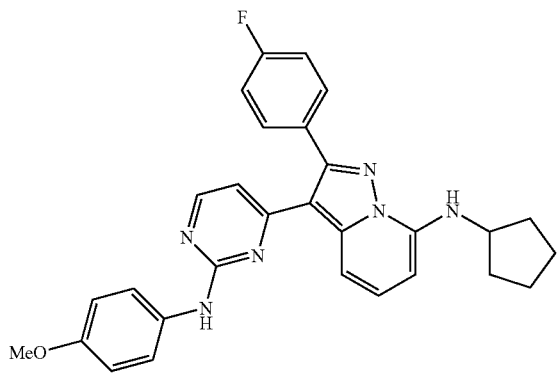

a) N-(4Methoxyphenyl)guanidinium Nitrate.

To a room temperature solution of 4-methoxyaniline (10.0 g, 81.19 mmol) in ethanol (100 mL) was added cyanamide (7.24 mL, 50 wt % in water, 93.37 mmol) followed by the dropwise addition of concentrated nitric acid (5.71 mL). The mixture was heated at reflux for 3 hours and allowed to cool to room temperature. The resulting crystals were isolated on a filter to yield N-(4Methoxyphenyl)guanidinium nitrate (7.1 g, 38%) as a violet crystals. $^1$H NMR (DMSO-d$_6$): δ 9.39 (s, 1 H), 7.22 (s, 3 H), 7.17 (d, 2 H), 6.99 (d, 2 H)<3.76 (s, 3 H); $^{13}$C NMR (DMSO-d$_6$) δ 158.17, 156.26, 127.48, 127.27, 114.90, 55.40; MS m/z 166 (M+1 of free base).

b) N-Cyclopentyl-2-(4-fluorophenyl)-3-[2-(4methoxyanilino)-4-pyrimidinyl]pyrazolo[1,5-α]pyridin-7-amine.

In a similar manner as described in Example 1 from (2E)-1-[7-(cyclopentylamino)-2-(4-fluorophenyl)pyrazolo[1,5-α]pyridin-3-yl]-3-(dimethylamino)-2-propen-1-one (58 mg, 0.15 mmol) and N-(4methoxyphenyl)guanidinium nitrate (168 mg, 0.74 mmol) was formed N-cyclopentyl-2-(4-fluorophenyl)-3-[2-(4-methoxyanilino)-4-pyrimidinyl]pyrazolo[1,5-a]pyridin-7-amine (44 mg, 61%) as a white solid. $^1$H NMR (CDCl$_3$): δ 8.15 (d, 1 H), 7.70–7.66 (m, 3 H), 7.52–7.49 (d. 2 H), 7.33–7.30 (m, 2 H), 7.19 (t, 2 H), 6.92–6.89 (m, 2 H), 6.48 (d, 1 H), 6.09–6.04 (m, 2 H), 4.03 (m, 1 H), 3.85 (s, 3 H), 2.17 (m, 2 H), 1.90–1.65 (m, 6 H); $^{19}$F NMR (CDCl$_3$): δ −113.17; MS m/z495 (M+1).

EXAMPLE 4

N-Cyclopentyl-3-[2-(4fluoroanilino)-4-pyrimidinyl]-2-(4-fluorophenyl)pyrazolo[1,5-α]pyridin-7-amine

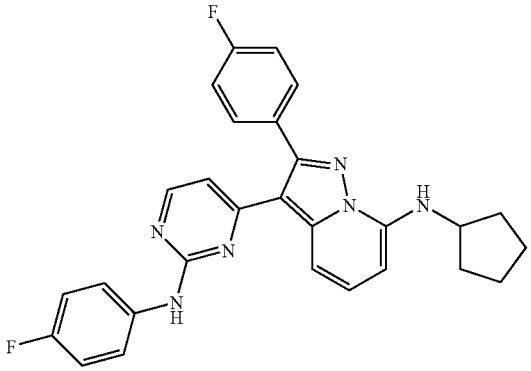

a) N-(4-Fluorophenyl)guanidinium Nitrate.

In a similar manner as described in Example 1 from 4fluoroaniline (10 g, 90 mmol) was obtained N-(4-fluorophenyl)guanidine nitrate (7.13 g, 37%) as a powder. $^1$H NMR (D$_2$O): δ 7.23–7.08 (m, 4 H); $^{19}$F NMR (D$_2$O) δ −114.38; $^{13}$C NMR (D$_2$O) δ 161.99 (d, $J_{CF}$=243.5 Hz), 156.83, 130.18 (d, $J_{CF}$=3.0 Hz),128.76 (d, $J_{CF}$=9.1 Hz), 116.87 (d, $J_{CF}$=22.8 Hz); MS m/z 154 (M+1 of free base).

b) N-Cyclopentyl-3-[2-(4-fluoroanilino)-4-pyrimidinyl]-2-(4-fluorophenyl)pyrazolo-[1,5-α]pyridin-7-amine.

In a similar manner as described in Example 1 from (2E)-1-[7-(cyclopentylamino)-2-(4-fluorophenyl)pyrazolo[1,5-α]pyridin-3-yl]-3-(dimethylamino)-2-propen-1-one (250 mg, 0.64 mmol) and N-(4-Fluorophenyl)guanidinium nitrate (685 mg, 3.15 mmol) was formed N-cyclopentyl-3-[2-(4fluoroanilino)-4-pyrimidinyl]-2-(4-fluorophenyl)pyrazolo[1,5-α]pyridin-7-amine (250 mg, 81%) as a white solid. $^1$H NMR (CDCl$_3$): δ 8.13 (d, 1 H), 7.65–7.59 (m, 3 H), 7.51 (m, 2 H), 7.28 (t, 1 H), 7.14 (t, 2 H), 6.89 (t, 2 H), 6.49 (d, 1 H), 6.05–6.01 (m, 2 H), 4.00 (m, 1 H), 2.18–2.10 (m, 2 H), 1.86–1.67 (m, 6 H); $^{13}$C NMR (CDCl$_3$): δ 163.21 (d, $J_{CF}$=246.6 Hz), 161.56, 160.16, 158.46 (d, $J_{CF}$=239.7 Hz), 156.84, 152.29, 142.75, 141.13, 135.71 (d, $J_{CF}$=3.1 Hz), 131.6 (d,$J_{CF}$=8.4 Hz), 129.73 (d, $J_{CF}$=3.8 Hz), 128.69, 121.50 (d, $J_{CF}$=8.3 Hz), 115.60 (d, $J_{CF}$=21.3 Hz), 115.33 (d, $J_{CF}$=22.0 Hz), 110.79, 106.84, 104.99, 90.35, 53.88, 33.32, 24.05; $^{19}$F NMR (CDCl$_3$): δ −113.09, −121.26; MS m/z483 (M+1).

EXAMPLE 5

[3-({[4–7-(Cyclopentylamino)-2-(4-methoxyphenyl)pyrazolo[1,5-α]pyridin-3-yl]-2-pyrimidinyl}amino)phenyl](phenyl)methanone

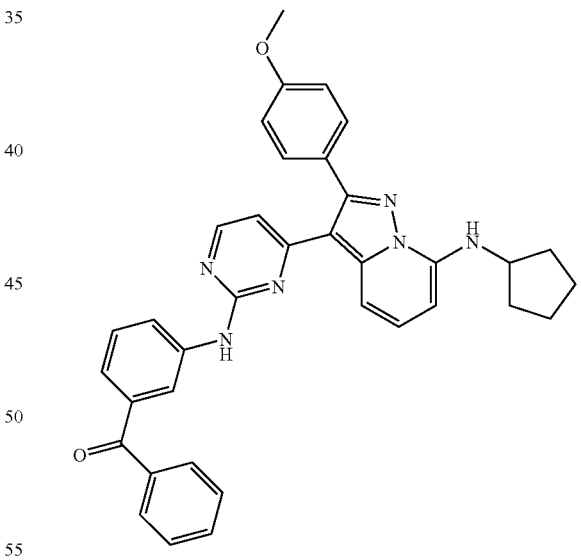

a) 2-(6-Chloro-2-pyridinyl)-1-(4-methoxyphenyl)ethanone.

To a cold (0° C.) solution of 6-chloro-2-picoline (18.3 mL 166.5 mmol) and ethyl 4-methoxybenzoate (30.0 g, 166.5 mmol) in tetrahydrofuran (300 mL) was added lithium bis(trimethylsilyl)amide (333 mL, 1.0 M in tetrahydrofuran, 332.7 mmol) dropwise via a pressure equalizing funnel over 1 hour. Upon complete addition, the cold bath was removed and the resulting solution was heated at 45 ° C. for 15 hours. The mixture was cooled to room temperature, and the solution was concentrated. Methanol was added to quench the reaction, resulting in the formation of a yellow precipitate. The precipitate was collected by filtration and dried to give 2-(6-chloro-2-pyridinyl)-1-(4-methoxyphenyl)ethanone (37.4 g, 86%) as a yellow solid. $^1$H NMR (CDCl$_3$): δ 7.99 (d, 2 H), 7.57 (t, 1 H), 7.22–7.19 (m, 2 H), 6.90 (d, 2H), 4.39 (s, 2H), 3.83 (s, 3 H); MS m/z 262 (M+1).

b) 2-(6-Chloro-2-pyridinyl)-1-(4-methoxyphenyl)ethanone Oxime.

To a solution of 2-(6-chloro-2-pyridinyl)-1-(4-methoxyphenyl)ethanone (37.4 g, 142.9 mmol) in methanol (500 mL) was added hydroxylamine hydrochloride (49.7 g, 714.5 mmol) followed by the addition of a sodium hydroxide solution (28.6 g, 714.5 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried to give 2-(6chloro-2-pyridinyl)-1-(4-methoxyphenyl)ethanone oxime (38.7 g, 97%) as a white solid. $^1$H NMR (CDCl$_3$): δ 8.23 (b, 1H), 7.63 (d, 2H), 7.48 (d,1 H), 7.12 (m, 2H), 6.83 (dd, 2H), 4.33 (s, 2H), 3,76 (s, 3 H); MS m/z 277 (M+1).

c) 7-Chloro-2-(4-methoxyphenyl)pyrazolo[1,5-α]pyridine.

To a solution of 2-(6-chloro-2-pyridinyl)-1-(methoxyphenyl)ethanone oxime (38.7 g, 140 mmol) in 1,2-dimethoxyethane (156 mL) at 0° C. was added trifluoroacetic anhydride (20 mL, 140 mmol), keeping the temperature below 10° C. during the addition. After the addition was complete, the reaction was warmed to 15° C. The solution was then cooled to 4° C. and a solution of triethylamine (39 mL, 280 mmol) in 1,2-dimethoxyethane (15 mL) was added over a period of 0.5 hours. The mixture was allowed to warm to room temperature and was stirred at room temperature for 1.5 hours. To this mixture was added iron(II) chloride (0.18 g, 1.4 mmol) and the reaction was heated at 75° C. for 15 hours. The reaction mixture was poured into water (300 mL). The resulting suspension was extracted with ethyl acetate. The organic phase was dried (magnesium sulfate), filtered and concentrated to a solid. This solid was recrystallized from methanol to give 7-chloro-2-(4-methoxyphenyl)pyrazolo[1,5-α]pyridine (18.7 g, 52%) as pale yellow needles. $^1$H NMR (CDCl$_3$): δ 7.91 (d, 2H), 7.43 (d, 1H), 7.01 (t,1H), 6.95 (d, 2H). 6.81 (d,$_1$ 1H), 6.80 (s, 1H), 3.83 (s, 3 H); MS m/z 259 (M+1).

d) 1-[7-(Chloro)-2-(4methoxyphenyl)pyrazolo[1,5-α]pyridin-3-yl]ethanone.

To a solution of 7-chloro-2-(4-methoxyphenyl)pyrazolo [1,5-α]pyridine (18.7 g, 72.4 mmol) in toluene (300 mL) at room temperature was added acetic anhydride (8.2 mL, 86.9 mmol). Boron trifluoride diethyletherate (10.1 mL, 79.6 mmol) was then added dropwise and the resulting solution was heated at reflux for 4 hours. The reaction mixture was cooled to room temperature and quenched by the dropwise addition of saturated aqueous sodium bicarbonate. The reaction was extracted with ethyl acetate, and the ethyl acetate phase washed with brine, dried (magnesium sulfate), filtered and concentrated. The residue was purified by recrystallization from ethyl acetate-hexanes to give 1-[7-(chloro)-2-(4-methoxyphenyl)pyrazolo[1,5-α]pyridin-3-yl]ethanone (14.2 g, 65%) as reddish needles.$^1$H NMR (CDCl$_3$): δ 8.37 (dd, 1H), 7.49 (dd, 2H), 7.39 (dd, 1H), 7.10 (dd, 1H), 6.98 (dd, 2H), 3.84 (s, 3H), 2.13 (s, 3H); MS m/z 301 (M+1).

e) 1-[7-(Cyclopentylamino)-2-(4-methoxyphenyl)pyrazolo[1,5-α]pyridin-3-yl]ethanone.

To a solution of 1-[7-(chloro)-2-(4-methoxyphenyl)pyrazolo[1,5-α]pyridin-3-yl]ethanone (5.0 g, 16.6 mmol) in toluene (100 mL) was added successively racemic-2,2'-bis (diphenylphosphino)-1,1'-binaphthyl (620 mg, 1.0 mmol), cesium carbonate (8.12 g, 24.9 mmol), cyclopentylamine (8.2 mL, 83.1 mmol), and palladium (II) acetate (150 mg, 0.66 mmol). The resulting mixture was stirred at 95° C. for 4 hours, at which time the reaction was judged complete by thin layer chromatography. The solution was cooled to room temperature and diethylether and water were added to the reaction mixture. The phases were separated, and the aqueous phase again extracted with diethyl ether. The combined organic phases were dried (magnesium sulfate), filtered and concentrated. The resulting residue was purified by flash chromatography (4:1 hexanes:ethyl acetate) to give 1-[7-(cyclopentylamino)-2-(4-methoxyphenyl)pyrazolo[1,5-α] pyridin-3-yl]ethanone (5.66 g, 97%) as a yellow foam. $^1$H NMR (CDCl$_3$): δ 7.65 (d, 1 H), 7.48 (d, 2 H), 7.39 (t, 1 H), 6.99 (d, 2 H) 6.09 (d, 1 H), 6.01 (d, 1H), 3.95 (m, 1 H), 3.84 (s, 3H), 2.09 (s, 3H), 2.09–2.00 (m, 2H) 1.76–1.22 (m, 6 H); MS m/z 350 (M+1).

f) (2E)-1-[7-(Cyclopentylamino)-2-(4-methoxyphenyl) pyrazolo1,5-α]pyridin-3-yl)-3-(dimethylamino)2-propen-1-one.

A solution of 1-[7-(Cyclopentylamino)-2-(4-methoxyphenyl)pyrazolo[1,5-α]pyridin-3-yl]ethanone (5.56 g, 15.9 mmol) in N,N-dimethylformamide dimethyl acetal (25 mL) was heated at reflux for 5 days. The mixture was allowed to cool to room temperature. Water was added and the resulting mixture was extracted with ethyl acetate. The organic phase was dried (magnesium sulfate), filtered and concentrated. The resulting residue was purified by flash chromatography (7:3 ethyl acetate:acetone) to give (2)-1-[7-(cyclopentylamino)-2-(4-methoxyphenyl)pyrazolo[1,5-α]pyridin-3-yl]-3-(dimethylamino)-2-propen-1-one (5.97 g, 93%) as a colored syrup: $^1$H NMR (CDCl$_3$): δ 7.96–7.59 (m, 3 H), 7.53 (d, 1 H), 7.23 (dd, 1 H), 6.93 (d, 2 H), 5.97–5.94 (m, 2 H), 5.07 (d, 1 H), 3.95 (m, 1 H), 3.81 (s, 3 H), 3.0–2.3 (m, 6 H), 2.07 (m, 2 H), 1.76–1.60 (m, 6 H); MS m/z405 (M+1).

g) N-(3-Benzoylphenyl)guanidinium nitrate

To a room temperature solution of 3-aminobenzophenone (4.0 g, 20.2 mmol) in ethanol (50 mL) was added cyanamide (1.8 mL 50 wt % in water, 23.3 mmol) followed by the dropwise addition of concentrated nitric acid (1.42 mL). The mixture was heated at reflux for 2 hours and then additional cyanamide (1.8 mL, 50 wt % in water, 23.3 mmol) and nitric acid (1.42 mL) were added. The mixture was heated for an additional 1 hour then allowed to cool to room temperature. Ether was added and the precipitate collected on a filter. This material was recrystallized fromethyl acetate/methanol/ ether to yield N-(3-benzoylphenyl)guanidinium nitrate (2.5 g, 41%) as a white crystalline solid. $^1$H NMR (DMSO-d$_6$): δ 9.75 (s, 1 H), 7.76 (d, 2 H), 7.69 (t, 1 H), 7.61 (d, 2 H), 7.58–7.49 (m, 9 H); $^{13}$C NMR (DMSO-d$_6$): δ 195.01, 155.76, 138.31, 136.65, 135.80, 132.99, 130.05, 129.71, 128.67, 128.44, 127.39, 125.34; MS m/z 240 (M+1 of free base).

h) [3-({4-[7-(Cyclopentylamino)-2-(4methoxyphenyl)pyrazolo[1,5-α]pyridin-3-yl]-2- pyrimidinyl}amino)phenyl] (phenyl)methanone.

To a solution of (2E)-1-[7-(cyclopentylamino)-2-(4-methoxyphenyl)pyrazolo[1,5-α]pyridin-3-yl]-3-(dimethylamino)-2-propen-1-one (100 mg, 0.25 mmol) in N,N-dimethylformamide (5 mL) was added N-(3-benzoylphenyl) guanidinium nitrate (223 mg, 0.74 mmol) and potassium carbonate (102 mg, 0.74 mmol). The suspension was heated at 140 ° C. (bath temperature) for 18 hours. The mixture was cooled to room temperature, ether was added followed by water. The organic layer was washed with brine. The aqueous layer was extracted with ether and the combined organics were dried over magnesium sulfate. Filtration and concentration followed by flash chromatography (4:1 to 2:1 hexanes-ethyl acetate) provided [3-({(4-[7-(Cyclopentylamino)-2-(4methoxyphenyl)pyrazolo[1,5-α]pyridin-3-yl]-2-pyrimidinyl}amino)phenyl](phenyl)methanone (90 mg, 76%) as a yellow solid. $^1$H NMR (CDCl$_3$): δ 8.10 (d, 1 H), 8.04 (s, 1 H), 7.95 (d, 1 H), 7.81 (d, 2 H), 7.64 (d 1 H), 7.57 (d, 2 H), 7.53–7.38 (m, 6 H), 7.22 (t, 1 H), 6.98 (d, 2 H), 6.53 (d, 1 H), 6.04–5.99 (m, 2 H); 4.00 (m, 1 H), 3.86 (s,3 H), 2.12 (m, 2 H), 1.81–1.67 (m, 6 H); MS m/z581 (M+1).

EXAMPLE 6

4-[5-Chloro-2-(4-fluorophenyl)pyrazolo[1,5-α]pyridin-3-yl]-N-phenyl-2-pyrimidinamine

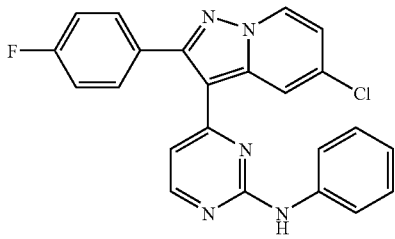

a) 2-(4Chloro-2-pyridinyl)-1-(4-fluorophenyl)ethanone.

To a cold (0 °C.) solution of 4-chloro-2-picoline (5.0 g,39 mmol) and ethyl 4-fluorobenzoate (6.6 g, 39 mmol) in tetrahydrofuran (100 mL) was added lithium bis(trimethylsilyl)amide (80 mL, 1.0 M in tetrahydrofuran, 80 mmol) dropwise via a pressure equalizing funnel over 30 minutes. Upon complete addition, the cold bath was removed and the resulting solution was stirred at room temperature for 15 hours. The reaction mixture was concentrated under reduced pressure and methanol was added to the reaction, resulting in the formation of a white precipitate. The precipitate was collected by filtration and dried to give 2-(4-chloro-2-pyridinyl)-1-(4-fluorophenyl)ethanone (9.6 g, 99%) as a white solid. $^1$H-NMR (DMSO-d$_6$): δ 7.90 (m, 3H), 7.11 (t, 2H), 6.56 (s,1 H), 5.67 (s, 1 H), 4.14 (m, 2H); $^{19}$F-NMR (DMSO-d$_6$): δ –115.67; MS m/z 250 (M+1).

b) 2-(4-Chloro-2-pyridinyl)-1-(4fluorophenyl)ethanone oxime.

To a solution of 2-(4-chloro-2-pyridinyl)-1-(4-fluorophenyl)ethanone (9.6 g, 38 mmol) in methanol (200 mL) was added hydroxylamine hydrochloride (13.5 g, 190 mmol) followed by the addition of a sodium hydroxide solution (7.8 g, 190 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried (magnesium sulfate) to give 2-(4chloro-2-pyridinyl)-1-(4-fluorophenyl)ethanone oxime (8.45 g, 84%) as a white solid. $^1$H-NMR (DMSO-d$_6$): δ 11.56 (s, 1H), 8.44 (d, 1H), 7.80 (m, 2H), 7.40 (m, 2H), 7.22 (m, 2H), 4.29 (s, 2 H); $^{19}$F-NMR (DMSO-d$_6$): δ –113.44; MS m/z 265 (M+1).

c) 5-Chloro-2-(4fluorophenyl)pyrazolo[1,5-α]pyridine.

To a solution of 2-(4-chloro-2-pyridinyl)-1-(4-fluorophenyl)ethanone oxime (8.0 g, 30 mmol) in 1,2-dimethoxyethane (50 mL) at 0° C. was added trifluoroacetic anhydride (6.3 g, 30 mmol), keeping the temperature below 10° C.

during the addition. After the addition was complete, the reaction was warmed to room temperature. The solution was then cooled to 4° C. and a solution of triethylamine (8.4 mL, 60 mmol) in 1,2-dimethoxyethane (20 mL) was added over a period of 0.5 hours. The mixture was allowed to warm to room temperature and was stirred for 1.5 hours. To this mixture was added iron(II) chloride (40 mg) and the reaction was heated at 75° C. for 15 hours. The reaction mixture was poured into water (300 mL). The resulting suspension was extracted with ethyl acetate. The combined organics were dried (magnesium sulfate), filtered and concentrated to a solid residue. This residue was purified by flash chromatography (1:1 ethyl acetate-hexane) to give 5-chloro-2-(4-fluorophenyl)pyrazolo[1,5-α]pyridine (4.2 g, 57 %) as a white solid. $^1$H-NMR (CDCl$_3$): δ 8.36 (d, 1H), 7.93 (q, 2H), 7.49 (d, 1H), 7.15 (t, 2H), 6.70 (dd, 1H), 6.69 (s, 1H); $^{19}$F-NMR (CDCl$_3$): δ –113.30; MS m/z 247 (M+1).

d) 5-Chloro-2-(4-fluorophenyl)pyrazolo[1,5-α]pyridine-3-carbaldehyde.

Phosphorous oxychloride (0.6 mL, 6.4 mmol) was added to N,N-dimethylformamide (10 mL) and the resulting mixture stirred at room temperature for 10 minutes. 5-Chloro-2-(4-fluorophenyl)pyrazolo[1,5-α]pyridine (1.0 g, 4.1 mmol) was added and the reaction mixture was stirred at room temperature for 12 hours. The reaction mixture was poured into ice-water and neutralized to pH 7 with aquous ammonium hydroxide. The resulting slurry was extracted with dichloromethane (3×40 mL). The combined organics were washed with brine, dried (magnesium sulfate), filtered and concentrated to give, after recrystallization from acetonitrile, 5-chloro-2-(4fluorophenyl)pyrazolo [1,5-α]pyridine-3-carbaldehyde (0.95 g, 85%) as a white solid. $^1$H-NMR (CDCl$_3$): δ10.07 (s, 1H),18.49 (d, 1H), 8.44 (d, 11H), 7.78 (q, 2H), 7.22 (t, 2H), 7.07 (dd, 1 H); MS m/z 275 (M+1).

e) 1-[5-Chloro-2-(4-fluorophenyl)pyrazolo[1,5-a]pyridin-3-yl]-2-butyn-1-one.

To a solution of 5-chloro-2-(4fluorophenyl)pyrazolo[1,5-α]pyridine-3-carbaldehyde (0.93 g, 3.4 mmol) in tetrahydrofuran (20 mL) at –78° C. was added ethynylmagnesium bromide (16 mL, 0.5 M in tetrahydrofuran, 8.0 mmol). The mixture was allowed to warm to room temperature and stirred for 1 hour. Water was added to the reaction and the resulting mixture was extracted with ethyl acetate. The ethyl acetate phase was dried (magnesium sulfate), filtered and concentrated to a solid residue. This residue was dissolved in dichloromethane (50 mL) and manganese dioxide (5 g) was added. This slurry was stirred at room temperature for 2 hours. The manganese dioxide was removed by filtration and the filtrate was concentrated to a solid. This solid was purified by flash chromatography (dichloromethane) to give 1-[5-chloro-2-(4-fluorophenyl)pyrazolo[1,5-α]pyridin-3-yl]-2-butyn-1-one (0.63 g, 62% for two steps) as a white solid. $^1$H-NMR (CDCl$_3$): δ 8.52 (d, 1H), 8.47 (d, 1H), 7.69 (q, 2H), 7.18 (t, 2H), 7.07 (dd, 1H), 3.00 (s, 1H); $^{19}$F-NMR (CDCl$_3$): δ –111.69; MS m/z 299 (M+1).

f) 4-[5-Chloro-2-(4-fluorophenyl)pyrazolo[1,5-α]pyridin-3-yl]- N-phenyl-2-pyrimidinamine.

To a solution of 1-[5-chloro-2-(4-fluorophenyl)pyrazolo [1,5-α]pyridin-3-yl]-2-butyn-1-one (1.0 g, 3.36 mmol) in 1-methyl-2-pyrrolidinone (4 mL) was added N-phenylguanidine nitrate (1.0 g, 5.0 mmol) and anhydrous potassium carbonate (0.7 g, 5.0 mmol). The resulting mixture was heated at 150° C. for 12 hours and concentrated in vacuo to a syrup. Ethyl acetate and water were added and the phases separated. The organic phase was dried (magnesium sulfate), filtered and concentrated to a solid. This solid was crystallized from acetonitrile to give 500 mg (36%) of 4-[5-chloro-2-(4-fluorophenyl)pyrazolo[1,5-α]pyridin-3-yl]-N-phenyl-2-pyrimidinamine as a yellow solid. $^1$H-NMR (CDCl$_3$): δ 8.48 (d, 1H), 8.45 (d, 1H), 8.23 (d,1H), 7.64 (m, 4H), 7.42 (t, 2H), 7.1–7.25 (m, 4H), 6.93 (dd, 1H), 6.52 (d, 1H); $^{19}$F-NMR (CDCl$_3$): δ–112.29; MS m/z 416 (M+1).

EXAMPLE 7

N-[3-(2-Anilino-4-pyrimidinyl)-2-(4fluorophenyl) pyrazolo[1,5-α]pyridin-5-yl]-N-cyclopentylamine

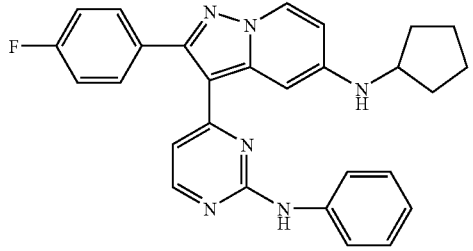

To a solution of 4-[5-chloro-2-(4-fluorophenyl)pyrazolo [1,5-a]pyridin-3-yl]-N-phenyl-2-pyrimidinamine (100 mg, 0.24 mmol) in cyclopentylamine (5 mL) was added successively racemic-2,2'-bis(diphenylphosphino)-1,1'-binaphthyl (72 mg), cesium carbonate (200 mg), and palladium (II) acetate (16 mg). The resulting mixture was stirred at 100° C. for 24 hours, then additional racemic-2,2'-bis(diphenylphosphino)-1,1'-binaphthyl (72 mg) and palladium (II) acetate (16 mg) were added and the reaction stirred at 100° C. for additional 24 hours, at which time the reaction was judged complete by thin layer chromatography. The solution was cooled to room temperature and ethyl acetate and water were added to the reaction mixture. The phases were separated, and the aqueous phase again extracted with ethyl acetate. The combined organic phases were dried (magnesium sulfate), filtered and concentrated. The resulting residue was purified by flash chromatography (1:1 hexanes:ethyl acetate) to give N-[3-(2-anilino-4-pyrimidinyl)-2-(4-fluorophenyl) pyrazolo[1,5-α]pyridin-5-yl]-N-cyclopentylamine (40 mg, 36%) as a solid. $^1$H NMR (CDCl$_3$): δ 8.21 (d, 1H), 8.13 (d, 1H), 7.65 (m, 4H), 7.4–7.24 (m, 4H), 7.18 (t, 21H), 7.06 (t, 1H), 6.44 (d 1H), 6.30 (dd, 1H), 4.16 (d, 1H), 3.68 (m, 1H), 1.4–2.2 (m, 8H); $^{19}$F-NMR (CDCl$_3$): δ–113.32; MS m/z 466 (M+1).

EXAMPLE 8

3-(2-Anilino-4-pyrimidinyl)-5-chloro-N-cyclopentyl-2-(4-fluorophenyl)pyrazolo[1,5-α]pyridin-7-amine

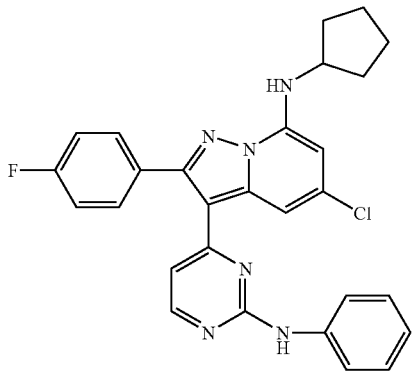

To a solution of 4-[5-chloro-2-(4-fluorophenyl)pyrazolo [1,5-α]pyridin-3-yl]-N-phenyl-2-pyrimidinamine (100 mg, 0.24 mmol) in anhydrous tetrahydrofuran (5 mL) was added n-butyllithium (0.53 mL of 1.6M solution in hexane, 0.84 mmol) at –78° C. The resulting dark solution was stirred for 10 minutes, then quenched by the addition of carbon tetrachloride (1 mL). The reaction mixture was allowed to warm to room temperature and water and ethyl acetate were added to the mixture. The phases were separated and the ethyl acetate phase dried (magnesium sulfate), filtered and concentrated to give 4-[5,7-dichloro-2-(4-fluorophenyl)pyrazolo[1,5-α]pyridin-3-yl]-N-phenyl-2-pyrimidinamine as a dark foam. This foam was dissolved in cyclopentylamine (5 mL) and the resulting solution was heated to 100° C. for 8 hours. The excess cyclopentylamine was removed under reduced pressure and the resulting syrup was-dissolved in ethyl acetate. The ethyl acetate phase was washed with water, dried (magnesium sulfate), filtered and concentrated. The resulting residue was purified by flash chromatography (1:1 hexanes:ethyl acetate) to give 3-(2-anilino-4-pyrimidinyl)-5-chloro-N-cyclopentyl-2-(4-fluorophenyl) pyrazolo[1, 5-α]pyridin-7-amine (15 mg, 13% for 3 steps) as a foam. $^1$H NMR (CDCl$_3$): δ 8.19 (d, 1H), 7.78 (d, 1H), 7.65 (4H), 7.39 (t, 2H), 7.2 (m, 2H), 7.10 (t. 1 H), 6.48 (d, 1H). 6.12 (d, 1 H), 6.06 (d, 1 H), 4.00 (m, 1H), 2.1–2.0 (m, 2H), 2.0–1.6 (m, 6H); $^9$F-NMR (CDCl$_3$): δ –112.65; MS m/z 499 (M+1).

EXAMPLE 9

N-{4-[5-Chloro-7-(ethylsulfanyl)-2-(4-fluorophenyl) pyrazolo[1,5-α]pyridin-3-yl]-2-pyrimidinyl }-N-phenylamine

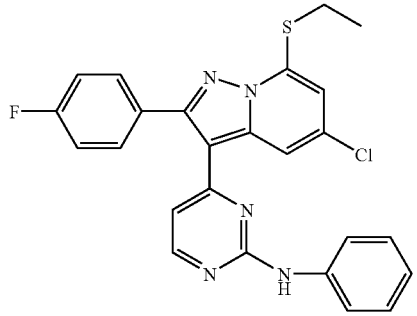

To a solution of 4-[5-chloro-2-(4-fluorophenyl)pyrazolo [1,5-α]pyridin-3-yl]-N-phenyl-2-pyrimidinamine (80 mg, 0.19 mmol) in tetrahydrofuran (5 mL) was added n-butyllithium (0.43 mL of 1.6M solution in hexane, 0.67 mmol) at –78° C. The resulting dark solution was stirred for 10 minutes, then quenched by the addition of ethyl disulfide (0.08 mL 6.5 mmol). The reaction mixture was allowed to warm to room temperature, then water and ethyl acetate were added. The phases were separated and the ethyl acetate phase was washed with water, dried (magnesium sulfate), filtered and concentrated. The resulting residue was crystallized from acetonitrile to give N-{4-[5-chloro-7-(ethylsulfanyl)-2-(4fluorophenyl)pyrazolo[1,5-α]pyridin-3-yl]-2-pyrimidinyl}-N-phenylamine (20 mg, 22%) as a solid. $^1$H NMR (CDCl$_3$): δ 8.30 (d, 1H), 8.22 (d, 1H), 7.66 (m, 3H), 7.40 (t, 2H), 7.1–7.24 (m, 4H), 6.75 (d, 1H), 6.52 (d, 1 H), 3.20 (q, 2H), 1.54 (t, 3H); $^{19}$F-NMR (CDCl$_3$): δ –112.55; MS m/z 476 (M+1).

EXAMPLE 10

N-Cyclopentyl-2-(4-methoxyphenyl)-3-[2-(3-nitroanilino)-4-pyrimidinyl]pyrazolo[1,5-α]pyridin-7-amine

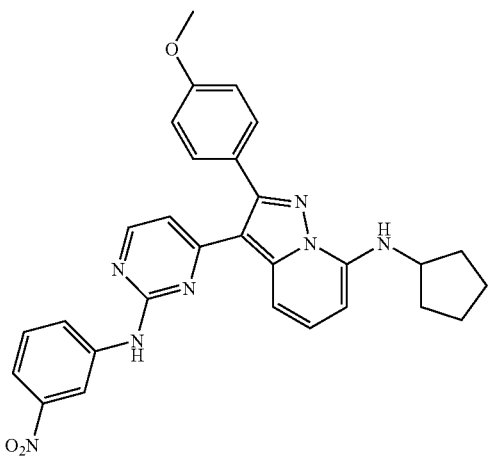

a) N-(3-Nitrophenyl)guanidinium nitrate.

In a similar manner as described in Example 1 from 3-nitroaniline (10 g, 72.4 mmol) was obtained N-(3-nitrophenyl)guanidinium nitrate (5.36 g, 310%) as a white crystalline solid. $^1$H NMR (DMSO-d$_6$): δ 9.94 (s, 1 H), 8.13–8.08 (m, 2 H), 7.74–7.66 (m, 5 H); $^{13}$C NMR (DMSO-d$_6$) δ 155.66, 148.34, 137.05, 131.05, 130.62, 120.72, 118.99; MS m/z 181 (M+1 of free base).

b) N-Cyclopentyl-2-(4methoxyphenyl)-3-[2-(3-nitroanilino)-4-pyrimidinyl]pyrazolo[1,5-α]pyridin-7-amine.

In a similar manner as described in Example 1 from (2E3–1-[7-(cyclopentylamino)-2-(4-methoxyphenyl)pyrazolo[1,5-α]pyridin-3-yl]-3-(dimethylamino)-2-propen-1-one (200 mg, 0.50 mmol) and N-(3-nitrophenyl)guanidinium nitrate (360 mg, 1.48 mmol) was formed N-cyclopentyl-2-(4-methoxyphenyl)-3-[2-(3-nitroanilino)-4-pyrimidinyl]pyrazolo[1,5-α]pyridin-7-amine (50 mg, 19%) as a yellow solid. $^1$H NMR (CDCl$_3$): δ 8.68 (s, 1 H), 8.18 (d, 1 H), 7.90 (s, 1 H), 7.81–7.78 (m, 2 H), 7.66 (d, 1 H), 7.56 (d, 2 H), 7.36 (t, 1 H), 7.28 (m, 1 H), 6.97 (d, 2 H), 6.63 (d, 1 H), 6.04–6.02 (m, 2 H), 3.99 (m, 1 H), 3.86 (s, 3 H), 2.13 (m, 2 H), 1.83–1.64 (m, 6 H); MS m/z 522 (M+1).

EXAMPLE 11

[3-({4-[7-(Cyclopentylamino)-2-(4-methoxyphenyl)pyrazolo[1,5-α]pyridin-3-yl]-2-pyrimidinyl}amino)phenyl]methanol

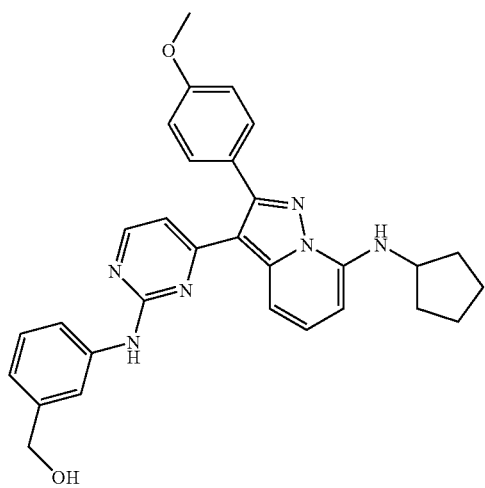

a) N-[3-(hydroxymethyl)phenyl]guanidinium nitrate.

In a similar manner as described in Example 1 from 3-(hydroxymethyl)aniline (10 g, 81.3 mmol) was obtained N-[3-(hydroxymethyl)phenyl]guanidinium nitrate (6.0 g, 32%) as a white solid. $^1$H NMR (DMSO-d$_6$): δ 9.62 (s, 1 H), 7.41–7.32 (m, 4 H), 7.22 (d, 1 H), 7.17 (s, 1 H), 7.09 (d, 1 H), 4.52 (s, 2 H); MS m/z 166 (M+1 of free base).

b) [3-({4-[7-(Cyclopentylamino)-2-(4-methoxyphenyl)pyrazolo[1,5-α]pyridin-3-yl]-2-pyrimidinyl}amino)phenyl]methanol.

In a similar manner as described in Example 1 from (2E)-1-[7-(cyclopentylamino)-2-(4-methoxyphenyl)pyrazolo[1,5-α]pyridin-3-yl]-3-(dimethylamino)-2-propen-1-one (111 mg, 0.27 mmol) and N-[3-(hydroxymethyl)phenyl]guanidinium nitrate (313 mg, 1.37 mmol) was formed [3-({4-[7-(Cyclopentylamino)-2-(4-methoxyphenyl)-pyrazolo[1,5-α]pyridin-3-yl]-2-pyrimidinyl}amino)phenyl]methanol (101 mg, 71%) as a yellow solid. $^1$H NMR (CDCl$_3$): δ 8.10 (d, 1 H), 7.71–7.69 (m, 2 H), 7.57 (d, 2 H), 7.47–7.45 (m, 2 H), 7.28–7.22 (m, 3 H), 6.50 (d, 1 H), 6.04–5.99 (m, 2 H), 4.63 (s, 2 H), 3.98 (m, 1 H), 3.85 (s, 3 H), 2.40 (broad, 1 H), 2.12 (m, 2 H), 1.85–1.65 (m, 6 H); MS m/z 507 (M+1).

EXAMPLE 12

N'-{4-[7-(Cyclopentylamino)-2-(4methoxyphenyl)pyrazolo[1,5-α]pyridin-3-yl]-2-pyrimidinyl}-1,3-benzenediamine

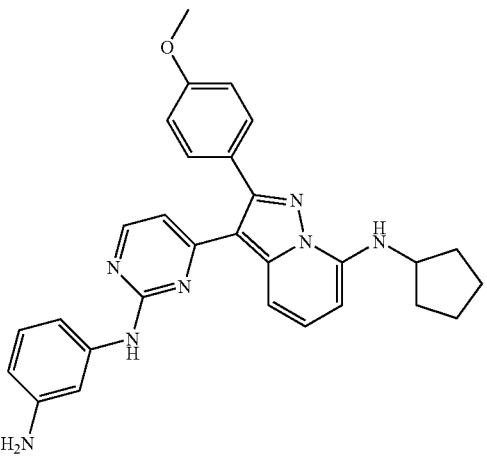

To a solution of N-cyclopentyl-2-(4-methoxyphenyl)-3-[2-(3-nitroanilino)-4-pyrimidinyl]pyrazolo[1,5-6]pyridin-7-amine (167 mg, 0.32 mmol) in ethanol (10 mL) was added tin(II)chloride dihydrate (304 mg, 1.60 mmol). The mixture was heated to 75° C. for 8 hours and then cooled to room temperature. Saturated aqueous sodium bicarbonate was added followed by ether. The organic layer was washed with brine. The aqueous layer was extracted with ethyl acetate and the combined organics were dried over magnesium sulfate. Filtration and concentration gave a solid residue which was purified by flash chromatography (1:1 hexanesethyl acetate to 100% ethyl acetate) to provide N'-{4-[7-(cyclopentylamino)-2-(4-methoxyphenyl)pyrazolo[1,5-α]pyridin-3-yl]-2-pyrimidinyl}-1,3-benzenediamine (40 mg, 25%) as a yellow solid. $^1$H NMR (CDCl$_3$): δ 8.15 (d, 1 H), 7.82 (d, 1 H). 7.64 (d, 2 H), 7.43 (s, 1 H), 7.34 (t, 1 H), 7.15–7.10 (m, 2 H), 7.03 (d, 2 H), 6.86 (d, 1 H), 6.55 (d, 1 H), 6.40 (d, 1 H), 6.11–6.06 (m, 2 H), 4.05 (m, 1 H), 3.91 (s, 3 H)<3.69 (broad, 2 H), 2.18 (m, 2 H), 1.90–1.66 (m, 6 H); MS m/z 492 (M+1).

EXAMPLE 13

3-[2-(3-Azidoanilino)-4-pyrimidinyl]-N-cyclopentyl-2-(4-methoxyphenyl)pyrazolo[-α]pyridin-7-amine

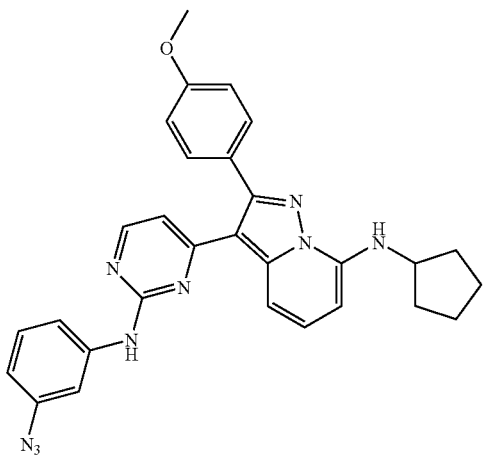

The following transformation was performed in the dark. To a cold (0° C.) solution of N'-{4-[7-(cyclopentylamino)-2-(4-methoxyphenyl)pyrazolo[1,5-α]pyridin-3-yl]-2-pyrimidinyl}-1,3-benzenediamine (16.5 mg, 0.03 mmol) in acetic acid/water (80/20, 1 mL) was added aqueous sodium nitrite (0.32 mL of a stock solution prepared by dissolving 200 mg of sodium nitrite in 25 mL water, 0.04 mmol). The resultant dark solution was stirred at 0° C. for 15 minutes. Aqueous sodium azide (0.11 mL of a stock solution prepared by dissolving 200 mg of sodium azide in 10 mL of water, 0.04 mmol) was added and the resultant solution was stirred for 1.5 hours over which time it was allowed to warm to room temperature. Ether was added and the solution made basic by dropwise addition of saturated aqueous sodium bicarbonate. The organic layer was washed with brine. The aqueous layer was extracted with ethyl acetate and the combined organics were dried over magnesium sulfate. Filtration and concentration gave a solid residue which was purified by flash chromatography (4:1 to 2:1 hexanes-ethyl acetate) to provide 3-[2-(3-azidoanilino)-4-pyrimidinyl]-N-cyclopentyl-2-(4-methoxyphenyl)pyrazolo[1,5-α]pyridin-7-amine (4 mg, 23%) as a tinted solid. $^1$H NMR (CDCl$_3$): δ 8.12 (d, 1 H), 7.71 (d, 1 H), 7.60–7.56 (m, 3 H), 7.33–7.25 (m, 3 H), 6.98 (d, 2 H), 6.70 (d, 1 H), 6.54 (d, 1 H), 6.05–6.04 (m, 2 H), 4.00 (m, 1 H), 3.87 (s, 3 H), 2.13 (m, 2 H), 1.85–1.58 (m, 6 H); MS m/z 518 (M+1).

EXAMPLE 14

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25× APE, and 5 ng of the digoxigenin-labeled detection probe). APE is 1.5 M NH$_4$-acetate, 0.15 M ammonium phosphate monobasic, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | IC$_{50}$ (µM) |
|---|---|
| 1 | 0.5 |
| 2 | 0.4 |
| 3 | 1.25 |
| 4 | 0.6 |
| 5 | 2.8 |
| 6 | 14 |
| 7 | 3.3 |
| 8 | 0.16 |
| 9 | 2 |
| 10 | 1 |
| 11 | 0.7 |
| 12 | 0.7 |
| 13 | 0.8 |

The results demonstrate that the compounds of the present invention are useful for the treatment and prophylaxis of herpes viral infections.

The invention claimed is:

1. A compound of formula (I):

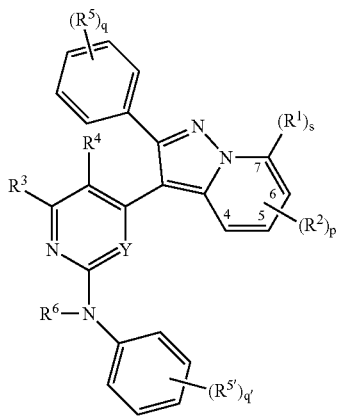

wherein:

s is 0 or 1;

p is 0, 1, 2 or 3;

$R^1$ and $R^2$ are the same or different and are each independently selected from the group consisting of halo, alkyl, alkenyl, alkynyl, cycloalkyl, cycloalkenyl, —R$^{10}$cycloalkyl, —NR$^7$R$^8$, Ay, —NHR$^{10}$Ay, —NR$^7$Ay, Het, —NHHet, —NHR$^{10}$Het, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent $R^2$ groups together with the atoms to which they are bonded form a 5- or 6-membered cycloalkyl or heterocyclic group containing 1 or 2 heteroatoms; or $R^1$ is in the C-6 position and $R^1$ and $R^2$ together with the atoms to which they are bonded form a 5- or 6-membered cycloalkyl or heterocyclic group containing 1 or 2 heteroatoms;

wherein when s is 0, p is 1, 2 or 3 and at least one $R^2$ is selected from the group consisting of —NR$^7$R$^8$, —NHR$^{10}$Ay, —NR$^7$Ay, —NHHet, and —NHR$^{10}$Het;

each $R^7$ and $R^8$ are the same or different and are each independently selected from the group consisting of H, alkyl, cycloalkyl, alkenyl, cycloalkenyl, —R$^{10}$cycloalkyl, —R$^{10}$OR$^9$, —NR$^9$R$^{11}$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{11}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

each $R^9$ and $R^{11}$ are the same or different and are each independently selected from the group consisting of H, alkyl, cycloalkyl, —R$^{10}$cycloalkyl, —R$^{10}$OH, —R$^{10}$OR$^{10}$, and —R$^{10}$NR$^{10}$R$^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N;

$R^3$ and $R^4$ are the same or different and are each independently selected from the group consisting of H, halo, alkyl, cycloalkyl, alkenyl, —OR$^7$, —R$^{10}$OR$^7$, —R$^{10}$OAy, —NR$^7$R$^8$, —R$^{10}$NR$^7$R$^8$, —C(O)R$^7$, C(O)Ay, —CO$_2$R$^7$, —CO$_2$Ay, —SO$_2$NHR$^9$, Ay, —OAy, —NR$^7$Ay, —R$^{10}$NR$^7$Ay, Het, —NHHet, and —NHR$^{10}$Het;

$R^6$ is selected from the group consisting of H, alkyl, cycloalkyl, alkenyl, cycloalkenyl, —R$^{10}$cycloalkyl, —R$^{10}$OR$^9$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, and —R$^{10}$SO$_2$NHCOR$^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —R$^{10}$cycloalkyl, —NR$^7$R$^8$, Ay, —NHR$^{10}$Ay, —NR$^7$Ay, Het, —NHHet, —NHR$^{10}$Het, —OR$^7$, —OAy, —OHet, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms or heteroaryl group containing 1 or 2 heteroatoms;

or a pharmaceutically acceptable salt or solvate thereof.

2. The compound according to claim 1 wherein s is 1.

3. The compound according to claim 1 wherein p is 0 or 1.

4. The compound according to claim 1 wherein $R^1$ is selected from the group consisting of halo, alkyl, cycloalkyl, —$R^{10}$cycloalkyl, —$NR^7R^8$, Ay, —$NHR^{10}$Ay, —$NR^7$Ay, Het, —NHHet, —$NHR^{10}$Het, —$OR^7$, —OAy, —OHet, —$R^{10}OR^9$, —$R^{10}NR^7R^8$, —$C(O)R^9$, —$CO_2R^9$, —$C(O)NR^7R^8$, —$S(O)_2NR^7R^8$, —$S(O)_nR^9$, cyano, azido and nitro.

5. The compound according to claim 1 wherein $R^1$ is selected from the group consisting of halo, alkyl, —$NR^7R^8$, —$NR^7$Ay, Het, —NHHet, —$NHR^{10}$Het, —$OR^7$, —$C(O)NR^7R^8$ and —$S(O)_nR^9$.

6. The compound according to claim 1 wherein each $R^2$ is the same or different and is independently selected from the group consisting of halo, alkyl, —$OR^7$, —$R^{10}OR^9$, —$NR^7R^8$, C(O)Het, —$CO_2R^9$, —$C(O)NR^7R^8$, Ay, —OAy, —$NR^7$Ay, —$NHR^{10}$Ay, —$C(O)NR^7$Ay, Het, —$C(O)NHR^{10}$Het, —NHHet, —$NHR^{10}$Het, —$S(O)_nR^9$, cyano, azido and nitro.

7. The compound according to claim 1, wherein each $R^2$ is the same or different and is independently selected from the group consisting of halo, alkyl, —$NR^7R^8$, —$NR^7$Ay, —NHHet and —$C(O)NR^7R^8$.

8. The compound according to claim 1 wherein $R^3$ and $R^4$ are the same or different and are each independently selected from the group consisting of H, halo, alkyl, —$OR^7$, —$R^{10}OR^7$, —$NR^7R^8$, —$R^{10}NR^7R^8$, —$CO_2R^7$ and Ay.

9. The compound according to claim 1 wherein $R^3$ and $R^4$ are each H.

10. The compound according to claim 1 wherein q is selected from the group consisting of 0, 1 and 2.

11. The compound according to claim 1 wherein q' is selected from the group consisting of 0, 1, 2 and 3.

12. The compound according to claim 1 wherein q is 1.

13. The compound according to claim 1 wherein each $R^5$ and $R^{5'}$ are the same or different and are each independently selected from the group consisting of halo, alkyl, alkenyl, —$OR^7$, —$CO_2R^9$, —$NR^7R^8$, —$C(O)NR^7R^8$, Ay, —OAy, —$NR^7$Ay, —$NHR^{10}$Ay, —$C(O)NR^7$Ay, Het, —$S(O)_2NR^7R^8$, cyano, nitro and azido.

14. The compound according to claim 1, wherein each $R^5$ and $R^{5'}$ are the same or different and are each independently selected from the group consisting of halo, alkyl, —$OR^7$, —$NR^7R^8$, cyano, nitro and azido.

15. The compound according to claim 1, wherein $R^6$ is selected from the group consisting of H, alkyl, cycloalkyl, —$R^{10}$cycloalkyl, —$C(O)R^9$, —$CO_2R^9$, —$C(O)NR^9R^{11}$, —$C(NH)NR^9R^{11}$, —$SO_2NR^9R^{11}$, —$R^{10}SO_2NR^9R^{11}$, —$SO_2R^{10}$ and —$R^{10}SO_2NHCOR^9$.

16. The compound according to claim 1, wherein $R^6$ is H.

17. A compound selected from the group consisting of:
3-(2-Anilino-4-pyrimidinyl)-N-cyclopentyl-2-(4-fluorophenyl)-pyrazolo[1,5-α]pyridin-7-amine;

N-Cyclopentyl-2-(4-fluorophenyl)-3-[2-(3,4,5-trimethoxyanilino)-4-pyrimidinyl]pyrazolo[1,5-α]pyridin-7-amine;

N-Cyclopentyl-2-(4-fluorophenyl)-3-[2-(4-methoxyanilino)-4-pyrimidinyl]pyrazolo[1,5-α]pyridin-7-amine;

N-Cyclopentyl-3-[2-(4-fluoroanilino)-4-pyrimidinyl]-2-(4-fluorophenyl)pyrazolo[1,5-α]pyridin-7-amine;

[3-({4-[7-(Cyclopentylamino)-2-(4-methoxyphenyl)pyrazolo[1,5-α]pyridin-3-yl]-2-pyrimidinyl}amino)phenyl](phenyl)methanone;

N-[3-(2-Anilino-4-pyrimidinyl)-2-(4-fluorophenyl)pyrazolo[1,5-α]pyridin-5-yl]-N-cyclopentylamine;

3-(2-Anilino-4-pyrimidinyl)-5-chloro-N-cyclopentyl-2-(4-fluorophenyl)pyrazolo[1,5-α]pyridin-7-amine;

N-{4-[5-Chloro-7-(ethylsulfanyl)-2-(4-fluorophenyl)pyrazolo[1,5-α]pyridin-3-yl]-2-pyrimidinyl}-N-phenylamine;

N-Cyclopentyl-2-(4-methoxyphenyl)-3-[2-(3-nitroanilino)-4-pyrimidinyl]pyrazolo[1,5-α]pyridin-7-amine;

[3-({4-[7-(Cyclopentylamino)-2-(4-methoxyphenyl)pyrazolo[1,5-α]pyridin-3-yl]-2-pyrimidinyl}amino)phenyl]methanol;

N'-{4-[7-(Cyclopentylamino)-2-(4-methoxyphenyl)pyrazolo[1,5-α]pyridin-3-yl]-2-pyrimidinyl}-1,3-benzenediamine; and 3-[2-(3-Azidoanilino)-4-pyrimidinyl]-*cyclopentyl-2-(4-methoxyphenyl)pyrazolo[1,5-α]pyridin-7-amine;

and pharmaceutically acceptable salts and solvates thereof.

18. A process for preparing the compound according to claim 1, wherein Y is N, $R^3$ is H and $R^4$ is H, said process comprising reacting the compound of formula (IX):

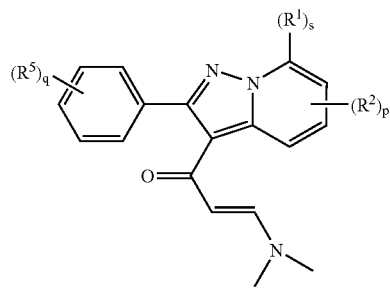

with a compound of formula (X):

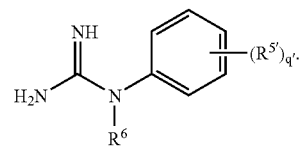

19. A process for preparing the compound according to claim 1 wherein Y is N; $R^3$ is selected from the group consisting of H, alkyl, cycloalkyl, alkenyl, —$R^{10}OR^7$, —$NR^7R^8$ where $R^7$ and $R^8$ are not H, —$R^{10}NR^7R^8$, —C(O)

$R^7$, —$CO_2R^7$, —$SO_2NHR^9$, Ay, and Het and $R^4$ is H, said process comprising reacting a compound of formula (XV):

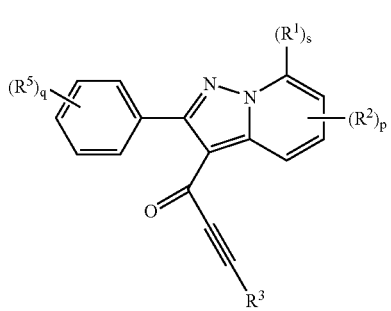
XV with a compound of formula (X):

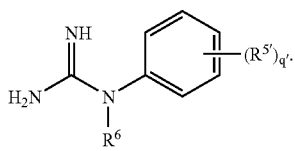
X

20. A process for preparing the compound according to claim 1, wherein Y is N, said process comprising reacting a compound of formula (XVIII):

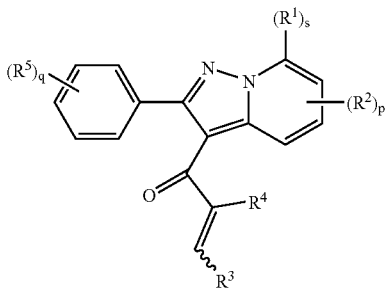
XVIII with a compound of formula (X):

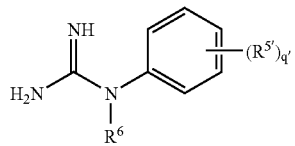
X followed by oxidative aromatization.

21. The process according to claim 18 further comprising the step of converting a compound of formula (I) to a pharmaceutically acceptable salt or solvate thereof.

22. The process according to claim 18 further comprising the step of converting a compound of formula (I) or a pharmaceutically acceptable salt or solvate thereof to another compound of formula (I) or a pharmaceutically acceptable salt or solvate thereof.

23. A pharmaceutical composition comprising a compound according to claim 1.

24. A pharmaceutical composition according to claim 23 further comprising a pharmaceutically acceptable carrier or diluent.

25. A pharmaceutical composition according to claim 23 further comprising an antiviral agent selected from the group consisting of aciclovir and valaciclovir.

26. A method for the treatment of a herpes simplex virus 1 or herpes simplex virus 2 infection in an animal, said method comprising administering to the animal a therapeutically effective amount of a compound of formula (I):

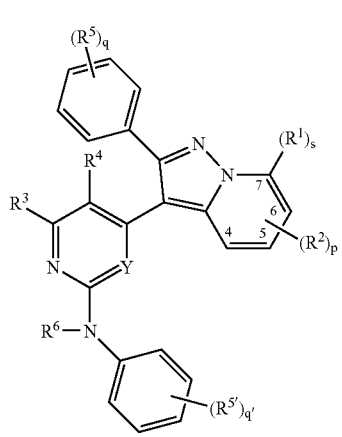
I wherein:
s is 0 or 1;
p is 0, 1, 2 or 3;
$R^1$ and $R^2$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}$Ay, —$NR^7$Ay, Het, —NHHet, —$NHR^{10}$Het, —$R^{10}$Ay, —$R^{10}$Het, —$OR^7_1$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —$C(O)NR^7R^8$, —C(O)$NR^7$Ay, —$C(O)NHR^{10}$Het, —$R^{10}C(O)NR^9R^{11}$, —$C(S)NR^9R^{11}$, —$R^{10}C(S)NR^9R^{11}$, —$R^{10}$NHC(NH)$NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^2$ groups together with the atoms to which they are bonded form a 5- or 6-membered cycloalkyl or heterocyclic group containing 1 or 2 heteroatoms; or $R^2$ is in the C-6 position and $R^1$ and $R^2$ together with the atoms to which they are bonded form a 5- or 6-membered cycloalkyl or heterocyclic group containing 1 or 2 heteroatoms;

each $R^7$ and $R^8$ are the same or different and are each independently selected from the group consisting of H, alkyl, cycloalkyl, alkenyl, cycloalkenyl, —$R^{10}$cycloalkyl, —$R^{10}OR^9$, —$NR^9R^{11}$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}$NHC(NH)$NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

each R⁹ and R¹¹ are the same or different and are each independently selected from the group consisting of H, alkyl, cycloalkyl, —R¹⁰cycloalkyl, —R¹⁰OH, —R¹⁰OR¹⁰, and —R¹⁰NR¹⁰R¹⁰;

each R¹⁰ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N;

R³ and R⁴ are the same or different and are each independently selected from the group consisting of H, halo, alkyl, cycloalkyl, alkenyl, —OR⁷, —R¹⁰R⁷, —R¹⁰OAy, —NR⁷R⁸, —R¹⁰NR⁷R⁸, —C(O)R⁷, C(O) Ay, —CO₂R⁷, —CO₂Ay, —SO₂NHR⁹, Ay, —OAy, —NR⁷Ay, —R¹⁰NR⁷Ay, Het, —NHHet, and —NHR¹⁰Het;

R⁶ is selected from the group consisting of H, alkyl, cycloalkyl, alkenyl, cycloalkenyl, —R¹⁰cycloalkyl, —R¹⁰OR⁹, —R¹⁰NR⁹R¹¹, —R¹⁰C(O)R⁹, —C(O)R⁹, —CO₂R⁹, —R¹⁰CO₂R⁹, —C(O)NR⁹R¹¹, —R¹⁰C(O)NR⁹R¹¹, —C(S)NR⁹R¹¹, —R¹⁰C(S)NR⁹R¹¹, —R¹⁰NHC(NH)NR⁹R¹¹, —R¹⁰C(NH)NR⁹R¹¹, —C(NH)NR⁹R¹¹, —SO₂NR⁹R¹¹, —R¹⁰SO₂NR⁹R¹¹, —R¹⁰NHSO₂R⁹, —SO₂R¹⁰, —R¹⁰SO₂R¹⁰, —R¹⁰NHCOR⁹, and —R¹⁰SO₂NHCOR⁹;

q and q' are the same or different and are each independently selected from the group consisting of 0, 1, 2, 3, 4 and 5;

each R⁵ and R⁵' are the same or different and are each independently selected from the group consisting of halo, alkyl, alkenyl, alkynyl, cycloalkyl, cycloalkenyl, —R¹⁰cycloalkyl, —NR⁷R⁸, Ay, —NHR¹⁰Ay, —NR⁷Ay, Het, —NHHet, —NHR¹⁰Het, —OR⁷, —OAy, —OHet, —R¹⁰OR⁹, —R¹⁰NR⁷R⁸, —R¹⁰NR⁷Ay, —R¹⁰C(O)R⁹, —C(O)R⁹, —C(O)Ay, —C(O)Het, —CO₂R⁹, —R¹⁰CO₂R⁹, —C(O)NR⁷R¹¹, —C(O)NR⁷Ay, —C(O)NHR¹⁰Het, —R¹⁰C(O)NR⁹R¹¹, —C(S)NR⁹R¹¹, —R¹⁰C(S)NR⁹R¹¹, —R¹⁰NHC(NH)NR⁹R¹¹, —C(NH)NR⁷R⁸, —C(NH)NR⁷Ay, —R¹⁰C(NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —S(O)ₙR⁹, cyano, azido and nitro; or two adjacent R⁵ or R⁵' groups together with the atoms to which they are bonded form a 5- or 6-membered cycloalkyl, aryl, heterocyclic group containing 1 or 2 heteroatoms or heteroaryl group containing 1 or 2 heteroatoms;

or a pharmaceutically acceptable salt or solvate thereof.

27. A method for the treatment of a condition or disease associated with a herpes viral infection selected from herpes simplex virus 1 and herpes simple virus 2 in an animal, comprising administering to the animal a therapeutically effective amount of a compound of formula (I):

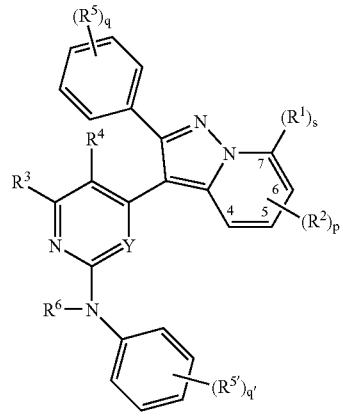

I wherein:
s is 0 or 1;
p is 0, 1, 2 or 3;
R¹ and R² are the same or different and are each independently selected from the group consisting of halo, alkyl, alkenyl, alkynyl, cycloalkyl, cycloalkenyl, —R¹⁰cycloalkyl, —NR⁷R⁸, Ay, —NHR¹⁰Ay, —NR⁷Ay, Het, —NHHet, —NHR¹⁰Het, —R¹⁰Ay, —R¹⁰Het, —OR⁷, —OAy, —OHet, —OR¹⁰Ay, —OR¹⁰Het, —R¹⁰OR⁹, —R¹⁰NR⁷R⁸, —R¹⁰NR⁷Ay, —R¹⁰C(O)R⁹, —C(O)R⁹, —C(O)Ay, —C(O)Het, —CO₂R⁹, —R¹⁰CO₂R⁹, —C(O)NR⁷R⁸, —C(O) NR⁷Ay, —C(O)NHR¹⁰Het, —R¹⁰C(O)NR⁹R¹¹, —C(S)NR⁹R¹¹, —R¹⁰C(S)NR⁹R¹¹, —R¹⁰NHC(NH) NR⁹R¹¹, —C(NH)NR⁷R⁸, —C(NH)NR⁷Ay, —R¹⁰C (NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —S(O)ₙR⁹, cyano, azido and nitro; or two adjacent R² groups together with the atoms to which they are bonded form a 5- or 6-membered cycloalkyl or heterocyclic group containing 1 or 2 heteroatoms; or R² is in the C-6 position and R¹ and R² together with the atoms to which they are bonded form a 5- or 6-membered cycloalkyl or heterocyclic group containing 1 or 2 heteroatoms;

each R⁷ and R⁸ are the same or different and are each independently selected from the group consisting of H, alkyl, cycloalkyl, alkenyl, cycloalkenyl, —R¹⁰cycloalkyl, —R¹⁰OR⁹, —NR⁹R¹¹, —R¹⁰NR⁹R¹¹, —R¹⁰C(O)R⁹, —C(O)R⁹, —CO₂R⁹, —R¹⁰CO₂R⁹, —C(O)NR⁹R¹¹, —R¹⁰C(O)NR⁹R¹¹, —C(S)NR⁹R¹¹, —R¹⁰C(S)NR⁹R¹¹, —R¹⁰NHC (NH)NR⁹R¹¹, —R¹⁰C(NH)NR⁹R¹¹, —C(NH) NR⁹R¹¹, —SO₂NR⁹R¹¹, —R¹⁰SO₂NR⁹R¹¹, —R¹⁰NHSO₂R⁹, —SO₂R¹⁰, —R¹⁰SO₂R¹⁰, —R¹⁰NHCOR⁹, and —R¹⁰SO₂NHCOR⁹;

each R⁹ and R¹¹ are the same or different and are each independently selected from the group consisting of H, alkyl, cycloalkyl, —R¹⁰cycloalkyl, —R¹⁰OH, —R¹⁰OR¹⁰, and —R¹⁰NR¹⁰R¹⁰;

each R¹⁰ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N;

$R^3$ and $R^4$ are the same or different and are each independently selected from the group consisting of H, halo, alkyl, cycloalkyl, alkenyl, —$OR^7$, —$R^{10}OR^7$, —$R^{10}OAy$, —$NR^7R^8$, —$R^{10}NR^7R^8$, —$C(O)R^7$, $C(O)Ay$, —$CO_2R^7$, —$CO_2Ay$, —$SO_2NHR^9$, Ay, —$OAy$, —$NR^7Ay$, —$R^{10}NR^7Ay$, Het, —NHHet, and —$NHR^{10}$Het;

$R^6$ is selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, and —$R^{10}SO_2NHCOR^9$;

q and q' are the same or different and are each independently selected from the group consisting of 0, 1, 2, 3, 4 and 5;

each $R^5$ and $R^{5'}$ are the same or different and are each independently selected from the group consisting of halo, alkyl, alkenyl, alkynyl, cycloalkyl, cycloalkenyl, —$R^{10}$cycloalkyl, —$NR^7R^8$, Ay, —$NHR^{10}Ay$, —$NR^7Ay$, Het, —NHHet, —$NHR^{10}$Het, —$OR^7$, —$OAy$, —OHet, —$R^{10}OR^9$, —$R^{10}NR^7R^8$, —$R^{10}NR^7Ay$, —$R^{10}C(O)R^9$, —$C(O)R^9$, —$C(O)Ay$, —$C(O)$Het, —$CO_2R^9$, —$R^{10}CO_2R^9$, —$C(O)NR^7R^8$, —$C(O)NR^7Ay$, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ or $R^{5'}$ groups together with the atoms to which they are bonded form a 5- or 6-membered cycloalkyl, aryl, heterocyclic group containing 1 or 2 heteroatoms or heteroaryl group containing 1 or 2 heteroatoms; or a pharmaceutically acceptable salt or solvate thereof.

\* \* \* \* \*

UNITED STATES PATENT AND TRADEMARK OFFICE
CERTIFICATE OF CORRECTION

PATENT NO. : 7,087,618 B2
APPLICATION NO. : 11/082466
DATED : August 8, 2006
INVENTOR(S) : Chamberlain et al.

It is certified that error appears in the above-identified patent and that said Letters Patent is hereby corrected as shown below:

On the title page item (74) should read:
Attorney, Agent, or Firm-Lorie Ann Morgan Column 67, line 60
Should read:
-- -$R^{10}C(O)R^9$, -$C(O)R^9$, -$C(O)Ay$, -$C(O)Het$,--

Column 68, line 21
Should read:
-- -$R^{10}NHSO_2R^9$, -$SO_2R^{10}$, -$R^{10}SO_2R^{10}$,--

Column 70, line 27
Should read:
-- N-{4-[7-(Cyclopentylamino)-2-(4-methoxyphenyl)pyra- --

Column 70, line 30
Should read:
-- 3-[2-(3-Azidoanilino)-4-pyrimidinyl]-N-cyclopentyl-2-(4- --

Column 73, line 48
Should read:
-- -$C(O)Het$, -$CO_2R^9$, -$R^{10}CO_2R^9$, -$C(O)NR^7R^8$, --

Column 74, line 39
Should read:
-- -$S(O)_nR^9$, cyano, azido and nitro; or --

UNITED STATES PATENT AND TRADEMARK OFFICE
CERTIFICATE OF CORRECTION

PATENT NO. : 7,087,618 B2
APPLICATION NO. : 11/082466
DATED : August 8, 2006
INVENTOR(S) : Chamberlain et al.

It is certified that error appears in the above-identified patent and that said Letters Patent is hereby corrected as shown below:

Column 75, line 16
Should read:
-- $-CO_2R^9$, $-R^{10}CO_2R^9$ $-C(O)NR^9R^{11}$, $-R^{10}C(O)$ --

Signed and Sealed this

Third Day of April, 2007

JON W. DUDAS
*Director of the United States Patent and Trademark Office*